United States Patent
Bashirullah et al.

(10) Patent No.: US 11,672,972 B2
(45) Date of Patent: Jun. 13, 2023

(54) NERVE STIMULATION DEVICE FOR UNIDIRECTIONAL STIMULATION AND CURRENT STEERING

(71) Applicants: Galvani Bioelectronics Limited, Brentford (GB); UCL Business PLC, London (GB)

(72) Inventors: Rizwan Bashirullah, Brentford (GB); Gerald Edwin Hunsberger, Brentford (GB); Matteo Donega, Brentford (GB); Daniel Chew, Brentford (GB); David Holder, London (GB); Kirill Aristovich, London (GB)

(73) Assignees: Galvani Bioelectronics Limited, Brentford (GB); UCL Business PLC, London (GB)

( * ) Notice: Subject to any disclaimer, the term of this patent is extended or adjusted under 35 U.S.C. 154(b) by 46 days.

(21) Appl. No.: 15/733,276

(22) PCT Filed: Dec. 11, 2018

(86) PCT No.: PCT/GB2018/053602
§ 371 (c)(1),
(2) Date: Jun. 19, 2020

(87) PCT Pub. No.: WO2019/122819
PCT Pub. Date: Jun. 27, 2019

(65) Prior Publication Data
US 2020/0316372 A1  Oct. 8, 2020

Related U.S. Application Data

(60) Provisional application No. 62/609,227, filed on Dec. 21, 2017.

(51) Int. Cl.
*A61N 1/05* (2006.01)
*A61N 1/36* (2006.01)

(52) U.S. Cl.
CPC ....... *A61N 1/0556* (2013.01); *A61N 1/36053* (2013.01); *A61N 1/36182* (2013.01)

(58) Field of Classification Search
CPC .............. A61N 1/0556; A61N 1/36053; A61N 1/36182; A61N 1/3605; A61N 1/36135;
(Continued)

(56) References Cited

U.S. PATENT DOCUMENTS

| 5,400,784 A | 3/1995 | Durand et al. |
| 5,919,220 A | 7/1999 | Stieglitz et al. |

(Continued)

FOREIGN PATENT DOCUMENTS

| DE | 4433111 A1 | 3/1996 |
| DE | 102014014927 A1 | 4/2016 |

(Continued)

OTHER PUBLICATIONS

Honert C V D., et al., "Generation of Unidirectionally Propagated Action Potentials in a Peripheral Nerve by Brief Stimuli," Science, vol. 206, No. 4424, Dec. 14, 1979, pp. 1311-1312.
(Continued)

*Primary Examiner* — Carl H Layno
*Assistant Examiner* — Anh-Khoa N Dinh
(74) *Attorney, Agent, or Firm* — Merchant & Gould P.C.

(57) ABSTRACT

A nerve interface device including at least one cuff portion having an assembled position in which the cuff portion forms at least part of a passageway for receiving a nerve along a longitudinal axis passing through the passageway; and first and second rings of electrodes mounted on the at least one cuff portion, each ring of electrodes including a plurality of electrodes. Each electrode in the first ring has a corresponding longitudinally-aligned electrode in the second ring so as to form a plurality of pairs of electrodes spaced apart from each other along the longitudinal axis.
(Continued)

The plurality of pairs of electrodes includes at least a first pair of electrodes, the first pair of electrodes mounted on the at least one cuff portion. The at least one cuff portion includes an asymmetric configuration about a central axis perpendicular to the longitudinal cuff axis.

22 Claims, 56 Drawing Sheets

(58) Field of Classification Search
CPC ........ A61N 1/025; A61N 1/0551; A61N 1/20; A61N 1/36062; A61N 1/36067; A61N 1/36071; A61N 1/36064; A61N 1/36057; A61N 1/3606; A61N 1/36114; A61N 1/00; A61N 1/02; A61N 1/10; A61N 1/18; A61N 1/16; A61N 1/40; A61N 1/44; A61N 1/403; A61N 1/445; A61B 5/24

See application file for complete search history.

(56) References Cited

U.S. PATENT DOCUMENTS

| | | | |
|---|---|---|---|
| 6,480,743 | B1 | 11/2002 | Kirkpatrick et al. |
| 9,314,637 | B2 | 4/2016 | Libbus |
| 2003/0045909 | A1 | 3/2003 | Gross et al. |
| 2003/0050677 | A1 | 3/2003 | Gross et al. |
| 2004/0015204 | A1 | 1/2004 | Whitehurst et al. |
| 2006/0136024 | A1 | 6/2006 | Cohen et al. |
| 2007/0129780 | A1 | 6/2007 | Whitehurst et al. |
| 2008/0132983 | A1 | 6/2008 | Cohen et al. |
| 2008/0243196 | A1 | 10/2008 | Libbus et al. |
| 2011/0160795 | A1 | 6/2011 | Osorio |
| 2013/0005169 | A1 | 1/2013 | Soltis et al. |
| 2013/0172774 | A1 | 7/2013 | Crowder et al. |
| 2014/0046407 | A1 | 2/2014 | Ben-Ezra et al. |
| 2014/0214135 | A1 | 7/2014 | Ben-David et al. |
| 2014/0228905 | A1 | 8/2014 | Bolea |
| 2015/0134031 | A1 | 5/2015 | Moffitt et al. |
| 2015/0202433 | A1* | 7/2015 | Franke ................. A61N 1/0556 607/72 |
| 2015/0321000 | A1 | 11/2015 | Rosenbluth et al. |
| 2016/0199651 | A1 | 7/2016 | Meadows et al. |
| 2016/0310741 | A1 | 10/2016 | Baru et al. |
| 2016/0331975 | A1 | 11/2016 | Henry et al. |
| 2017/0202467 | A1 | 7/2017 | Zitnik et al. |
| 2018/0161570 | A1 | 6/2018 | Renaux |
| 2020/0384265 | A1 | 12/2020 | Donega et al. |
| 2021/0093867 | A1 | 4/2021 | Donega et al. |
| 2021/0093868 | A1 | 4/2021 | Hunsberger |
| 2021/0138238 | A1 | 5/2021 | Holder et al. |

FOREIGN PATENT DOCUMENTS

| | | |
|---|---|---|
| GB | 2528070 A | 1/2016 |
| KR | 20120077585 A | 7/2012 |
| WO | WO-2008007065 A2 | 1/2008 |
| WO | WO-2008142027 A1 | 11/2008 |

OTHER PUBLICATIONS

Honert V. D.C., et al., "A Technique for Collision Block of Peripheral Nerve:Frequency Dependence,", IEEE Transactions on Biomedical Engineering, May 1981, vol. BME-28, No. 5, 4 pages.

International Preliminary Report on Patentability for Application No. PCT/GB2018/051749, dated Dec. 24, 2019, 9 pages.

International Preliminary Report on Patentability for Application No. PCT/GB2018/053597, dated Jun. 25, 2020, 9 pages.

International Preliminary Report on Patentability for Application No. PCT/GB2018/053600, dated Jun. 23, 2020, 8 pages.

International Preliminary Reporton Patentability for Application No. PCT/GB2018/053601, dated Jun. 23, 2020, 7 pages.

International Preliminary Report on Patentability for Application No. PCT/GB2018/053602, dated Jun. 23, 2020, 11 pages.

International Search Report and Written Opinion for Application No. PCT/GB2018/051749, dated Oct. 11, 2018, 13 pages.

International Search Report and Written Opinion for Application No. PCT/GB2018/053600, dated Mar. 22, 2019, 12 pages.

International Search Report and Written Opinion for Application No. PCT/GB2018/053601, dated Feb. 12, 2019, 10 pages.

International Search Report and Written Opinion for Application No. PCT/GB2018/053602, dated Feb. 13, 2019, 15 pages.

International Search Report and Written Opinion, International Application No. PCT/GB2018/053597, dated Jul. 17, 2019, 12 pages.

Sweeney J D., et al., "An Asymmetric Two Electrode Cuff for Generation of Unidirectional Propagated Action Potentials," IEEE Transactions on Biomedical Engineering, Jun. 1986, vol. 33, No. 6, pp. 541-549.

* cited by examiner

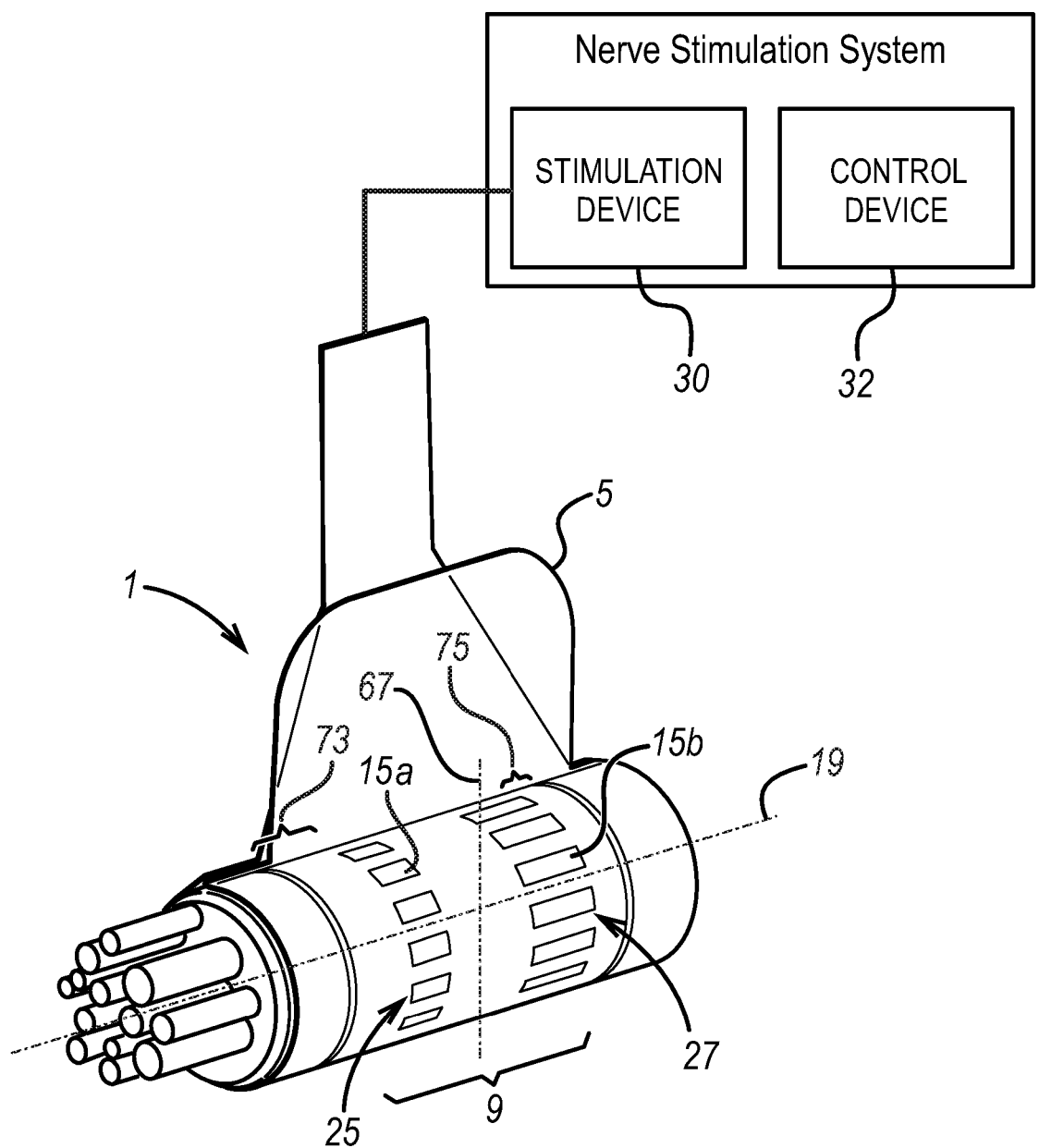

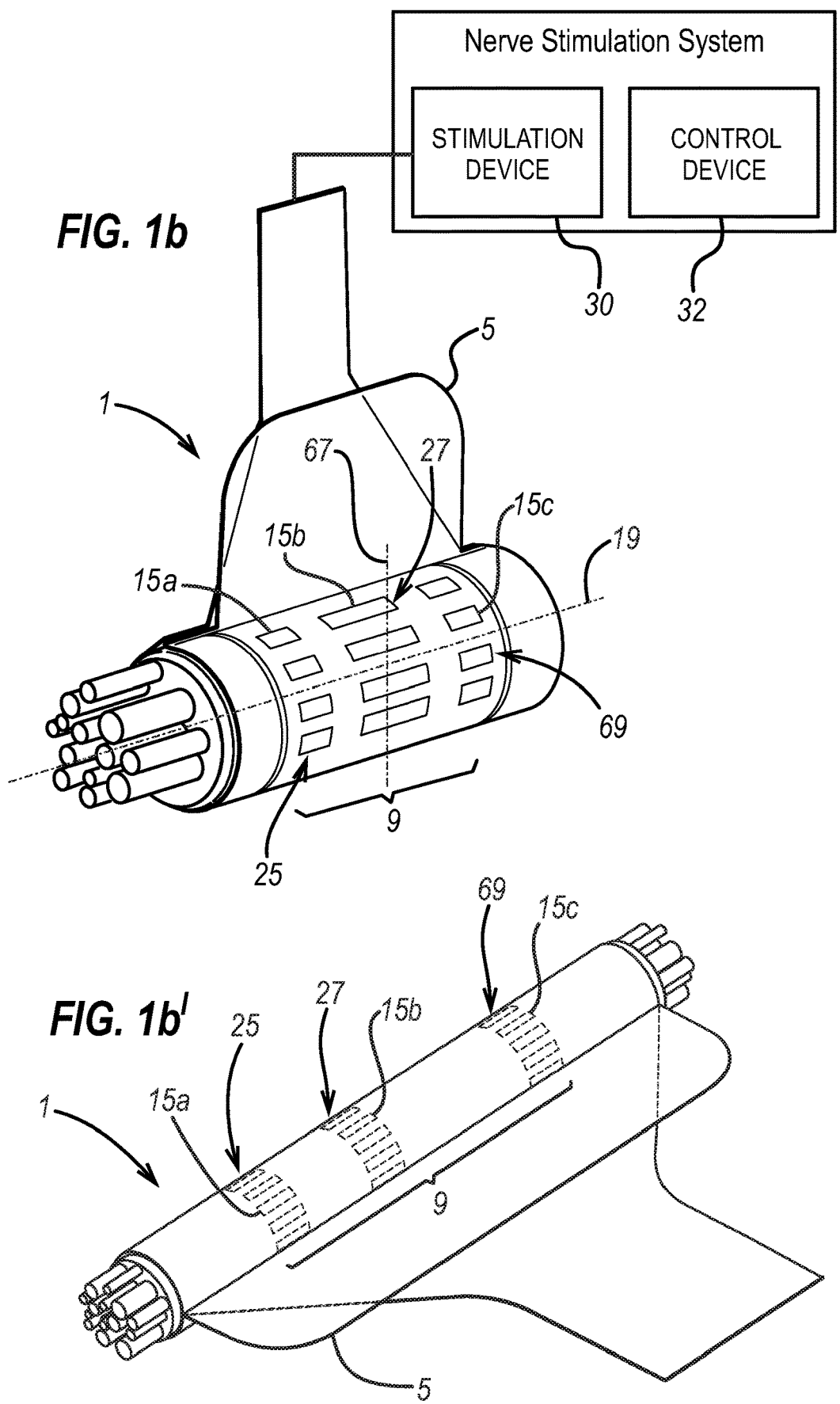

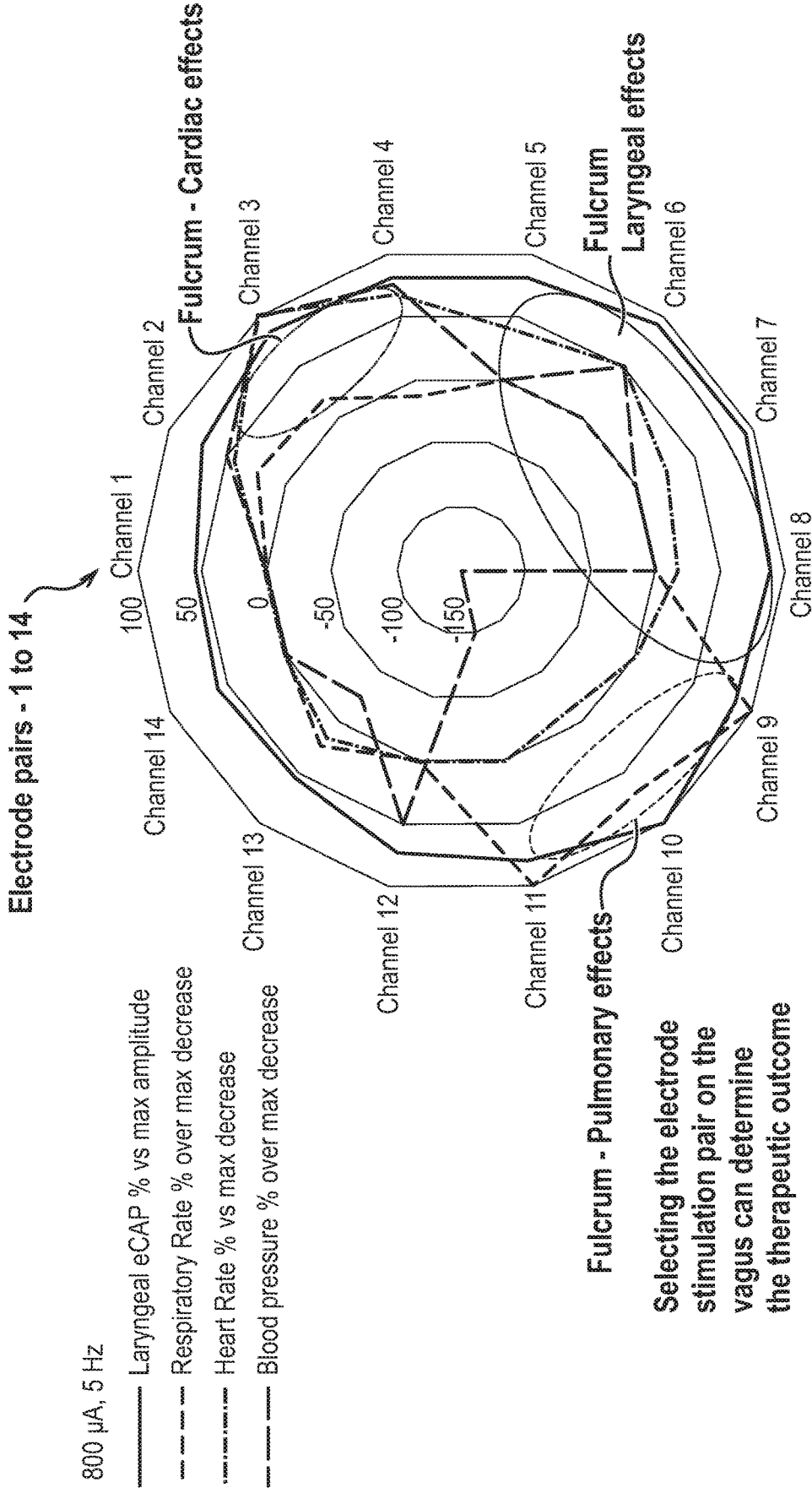

FIG. 3b
1mm array
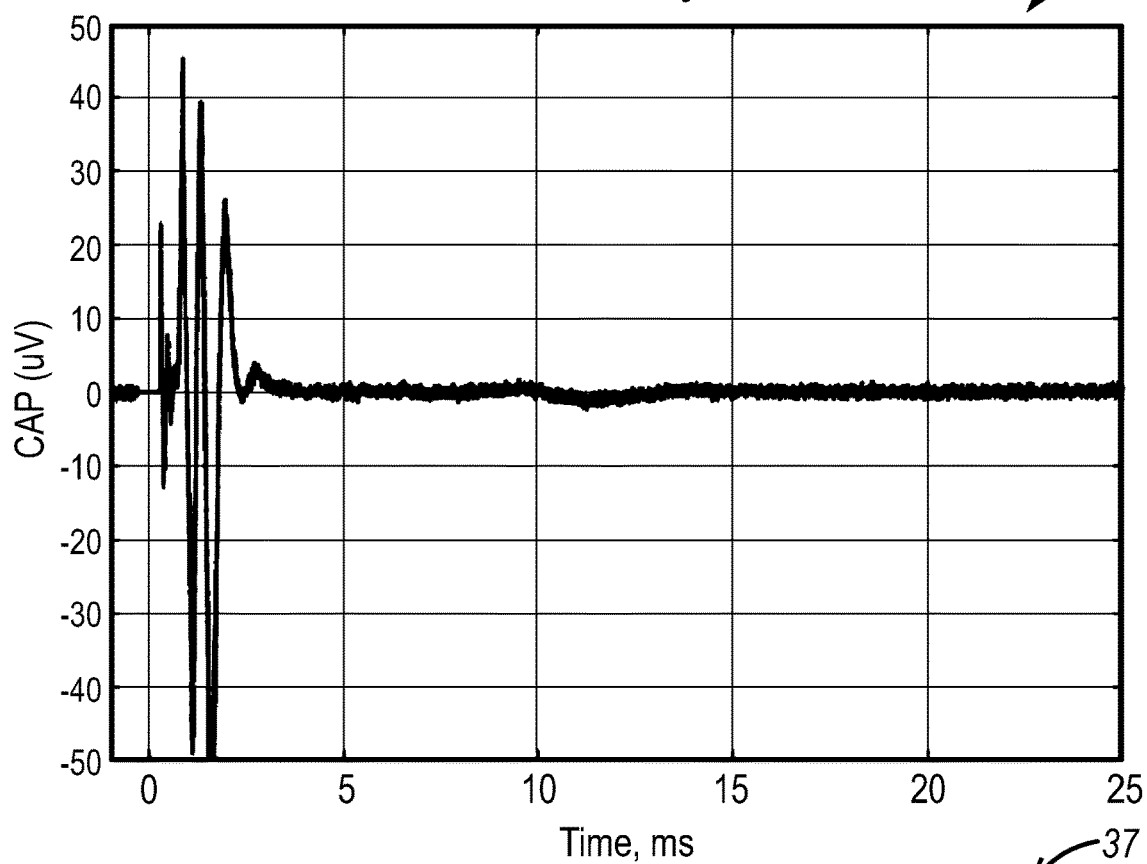
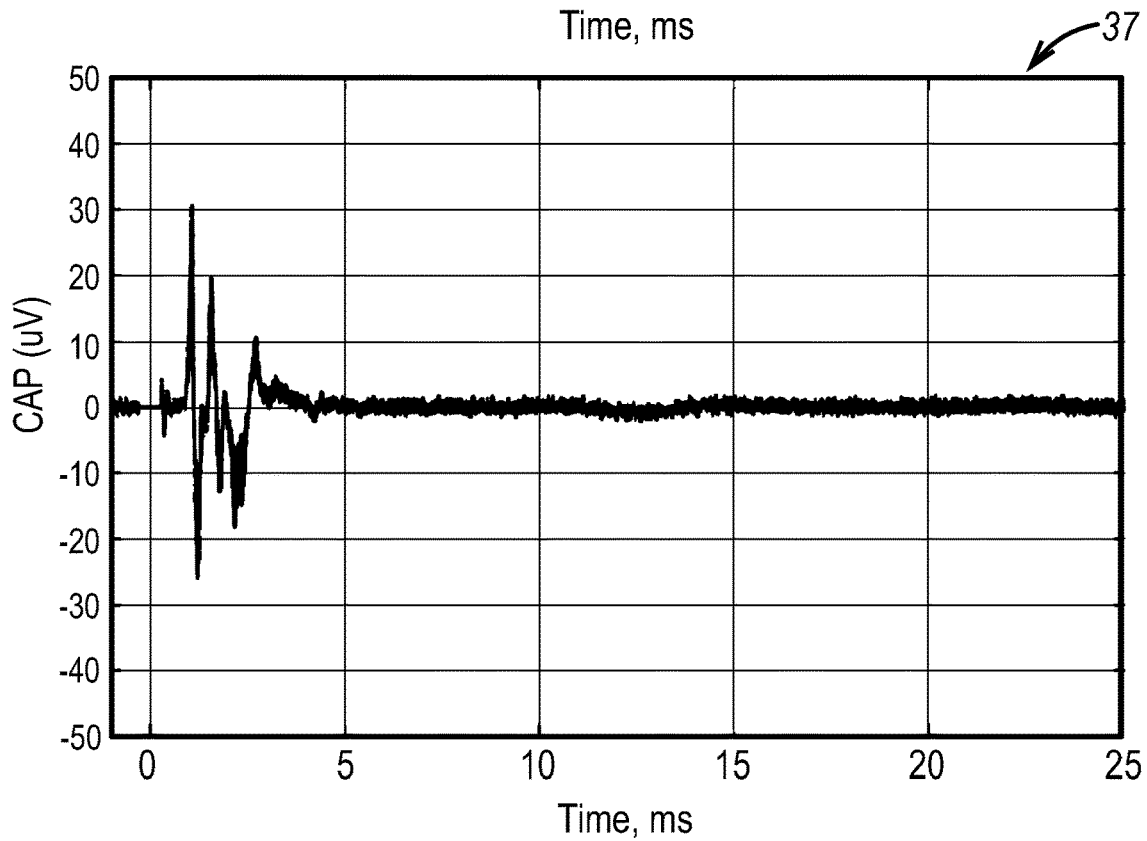

FIG. 3b(contd.)
3mm array
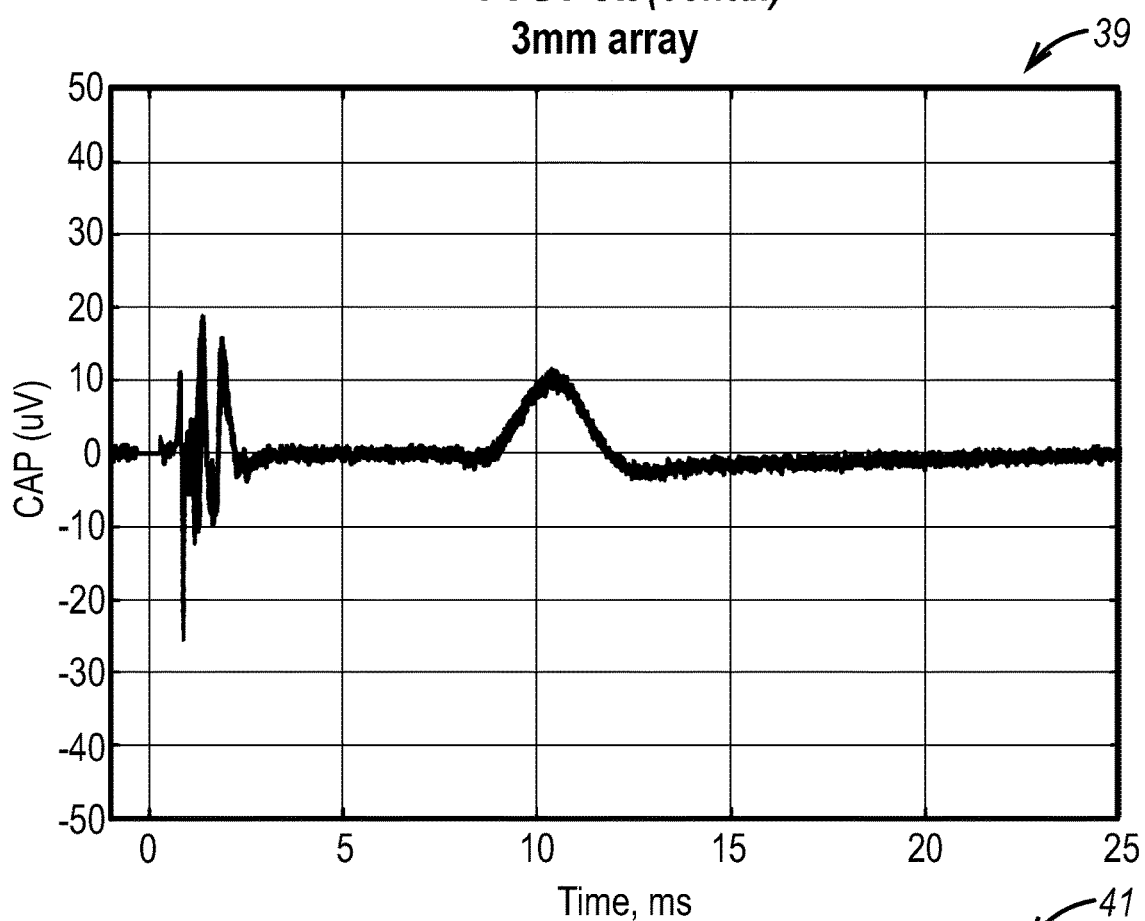
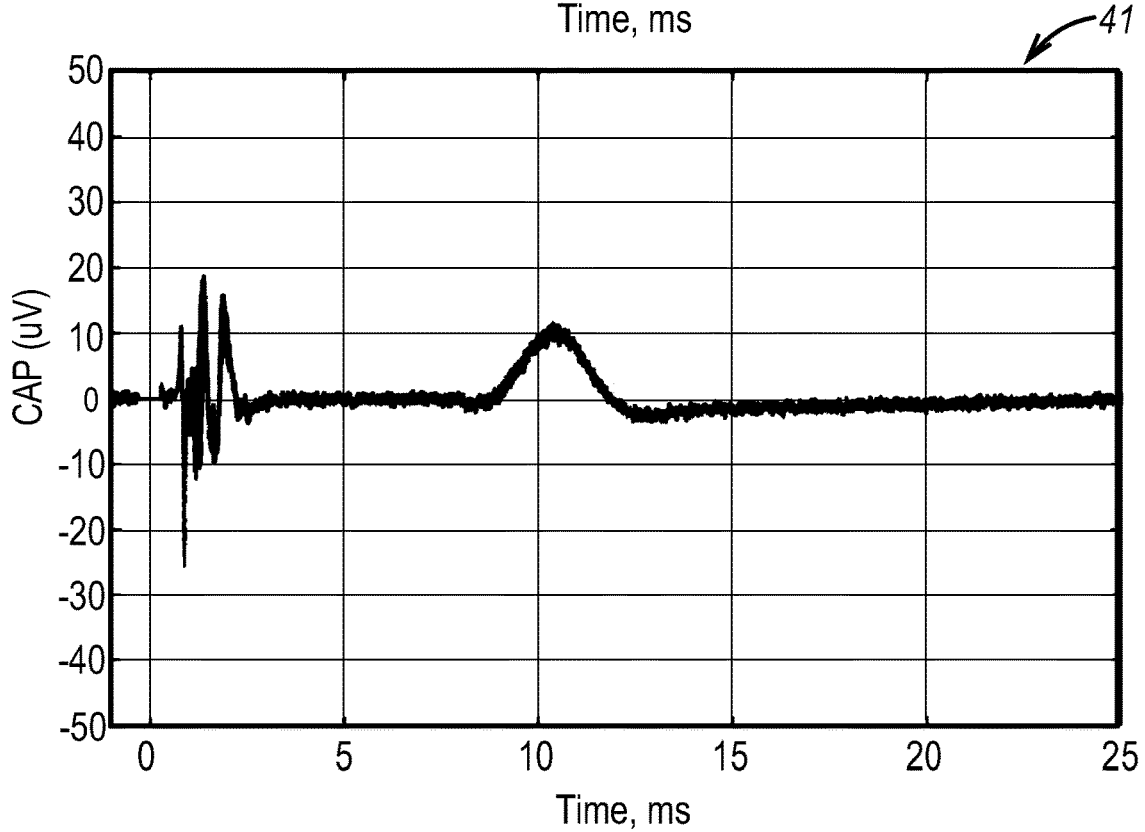

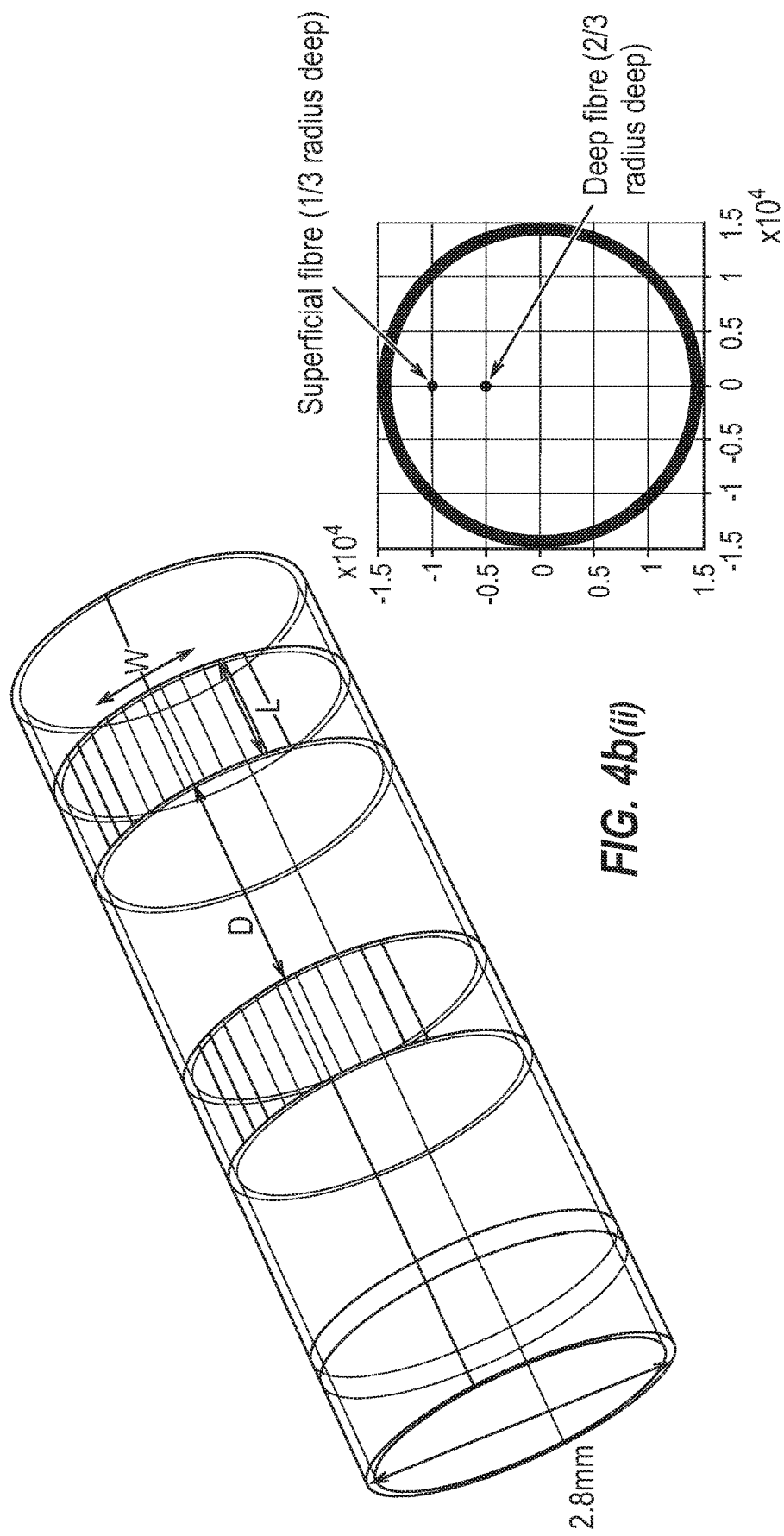
FIG. 4b(ii)

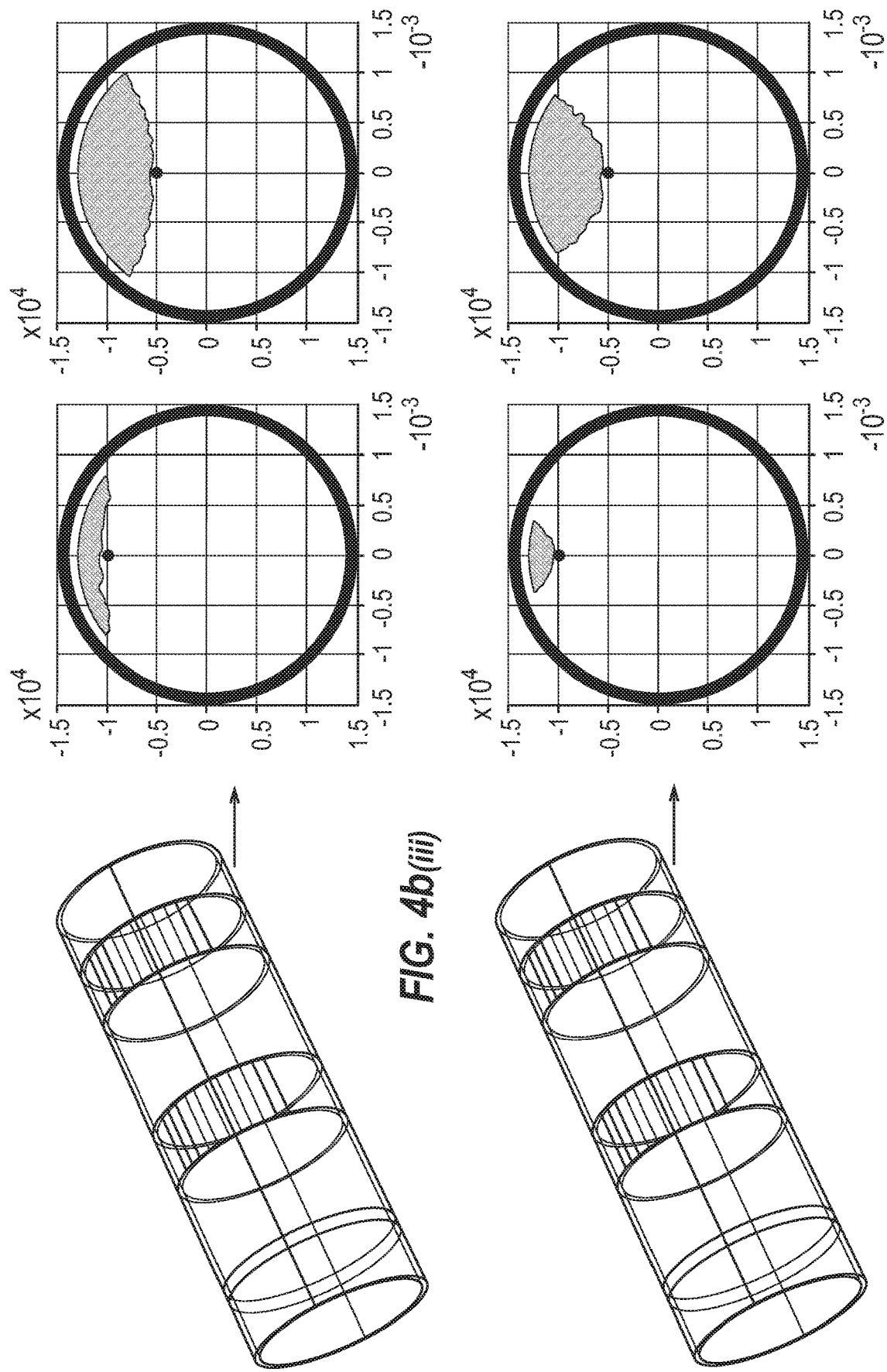
FIG. 4b(iii)

FIG. 4b(iv)
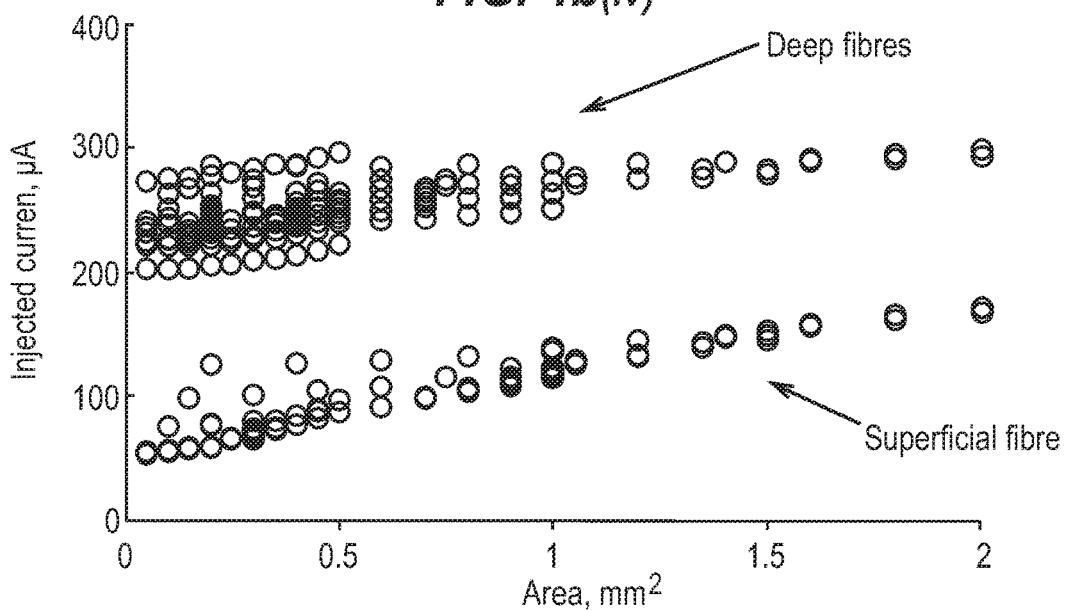
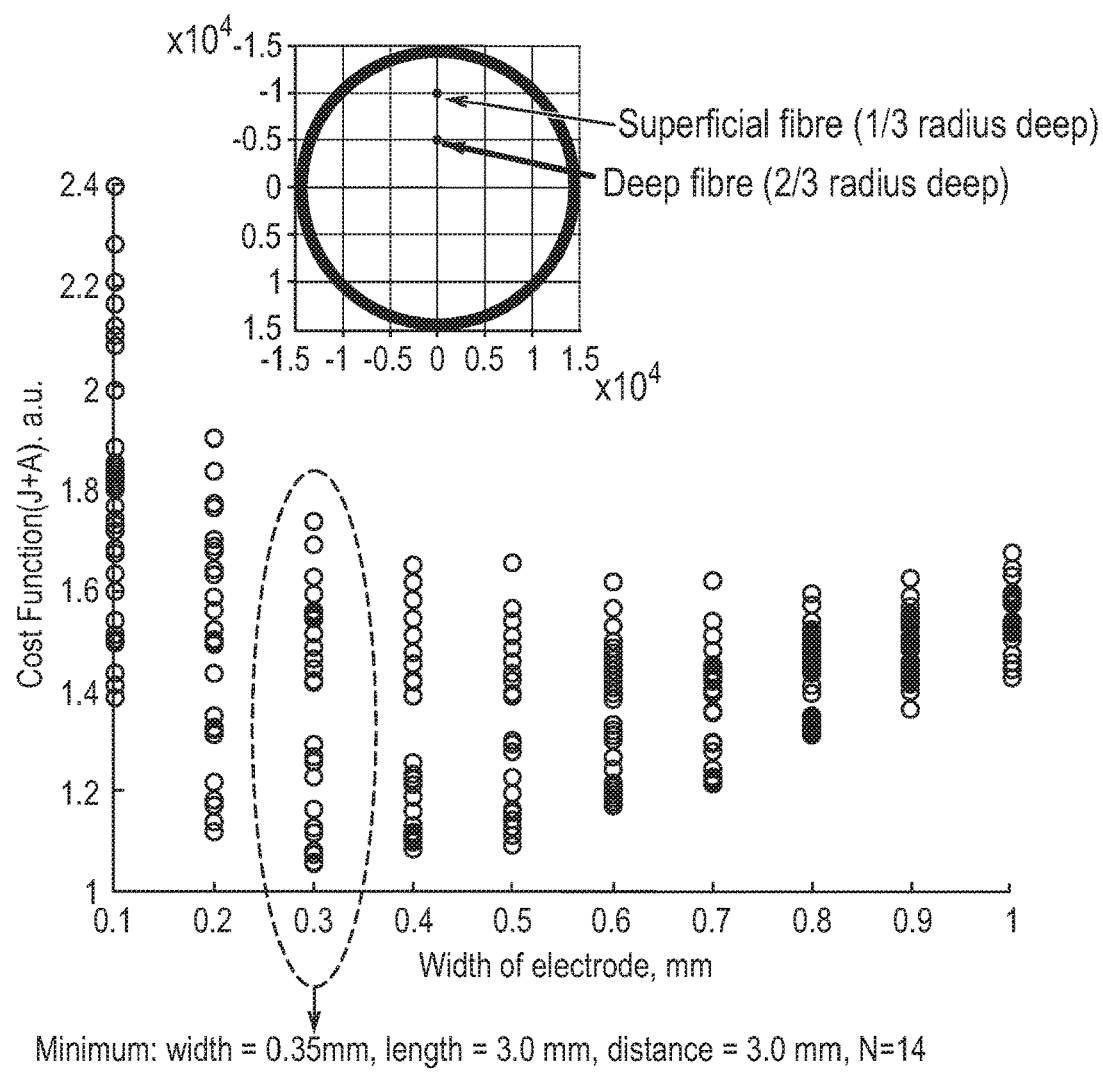

FIG. 5
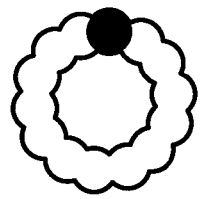 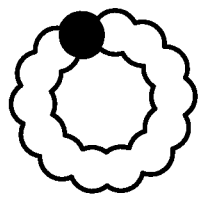 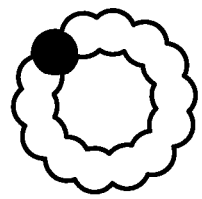 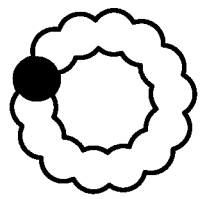
Pair = 1-1    Pair = 2-2    Pair = 3-3    Pair = 4-4
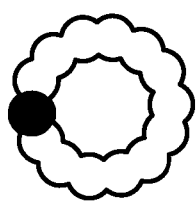 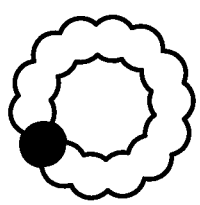 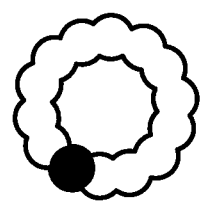 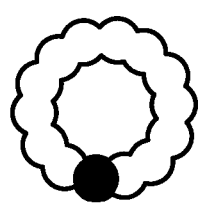
Pair = 5-5    Pair = 6-6    Pair = 7-7    Pair = 8-8
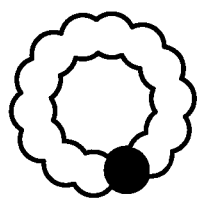 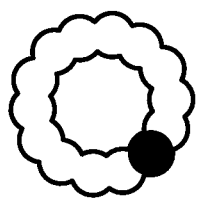 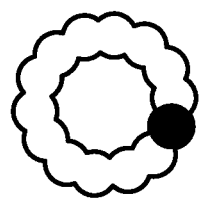 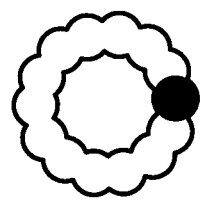
Pair = 9-9    Pair = 10-10    Pair = 11-11    Pair = 12-12
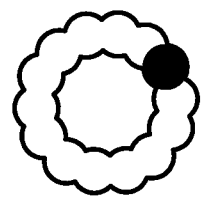 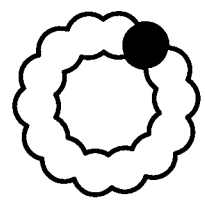
Pair = 13-13    Pair = 14-14

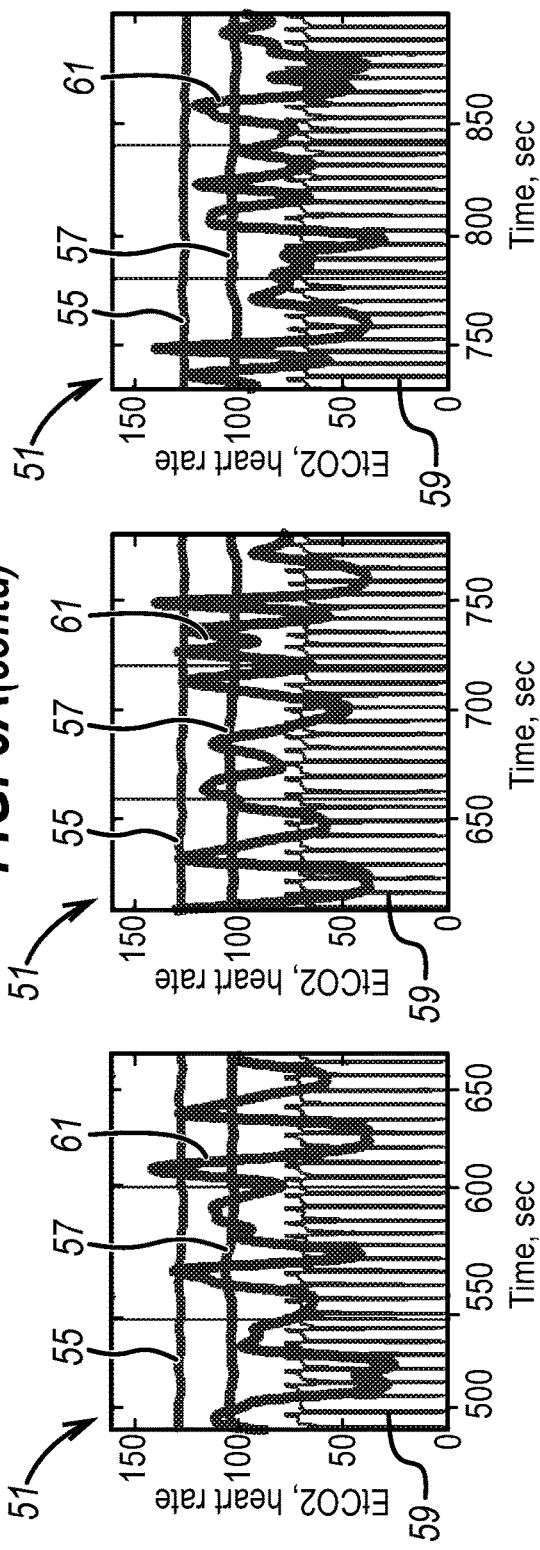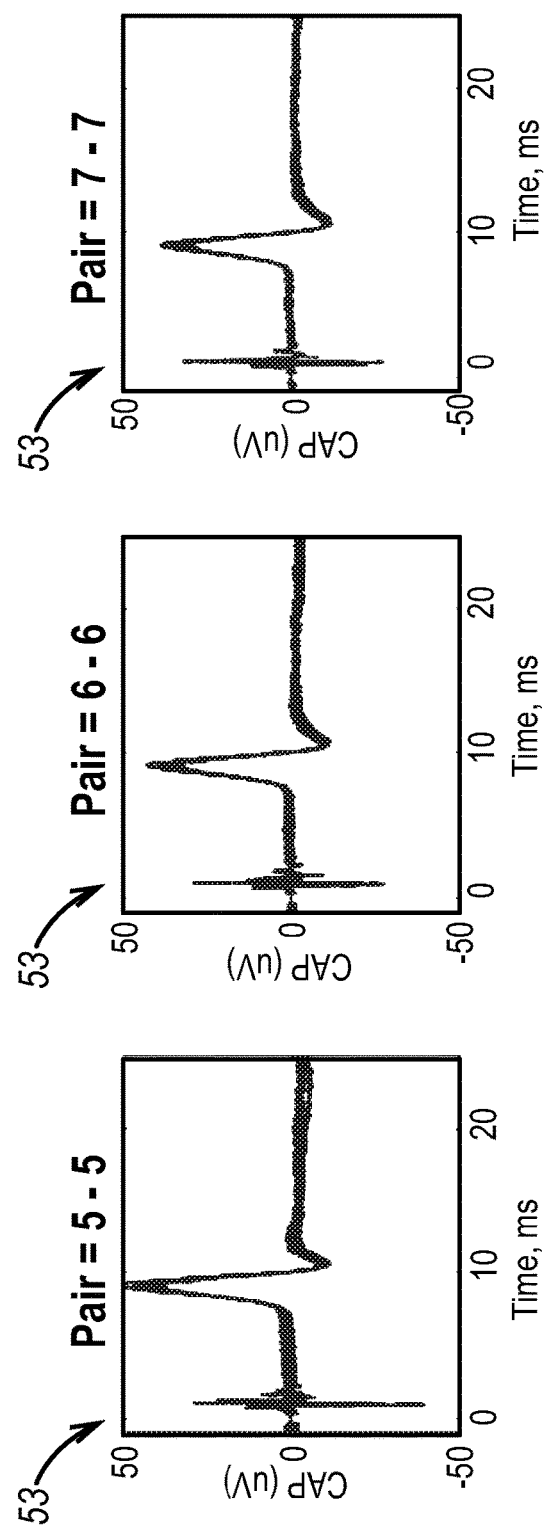
FIG. 6A(contd)

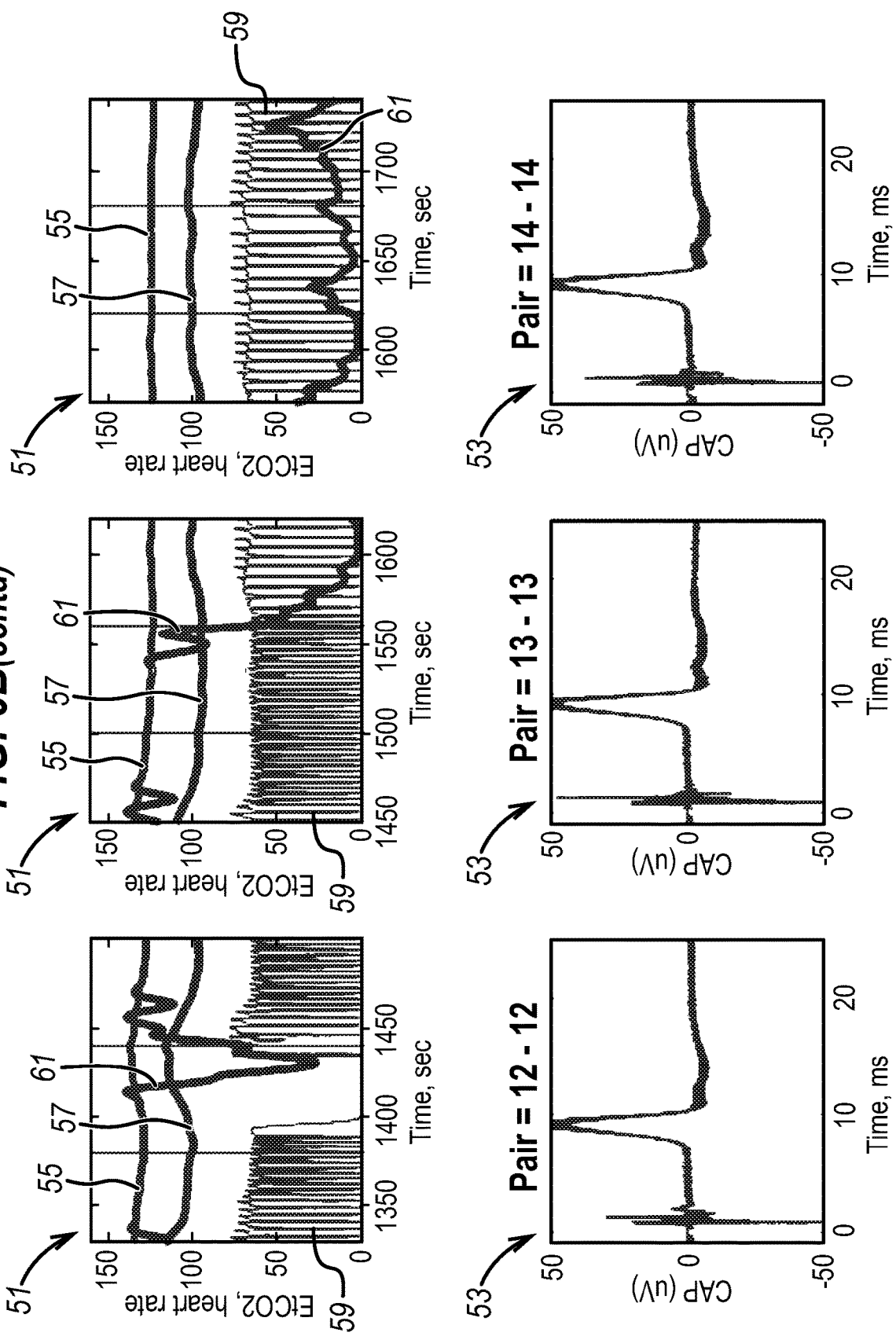

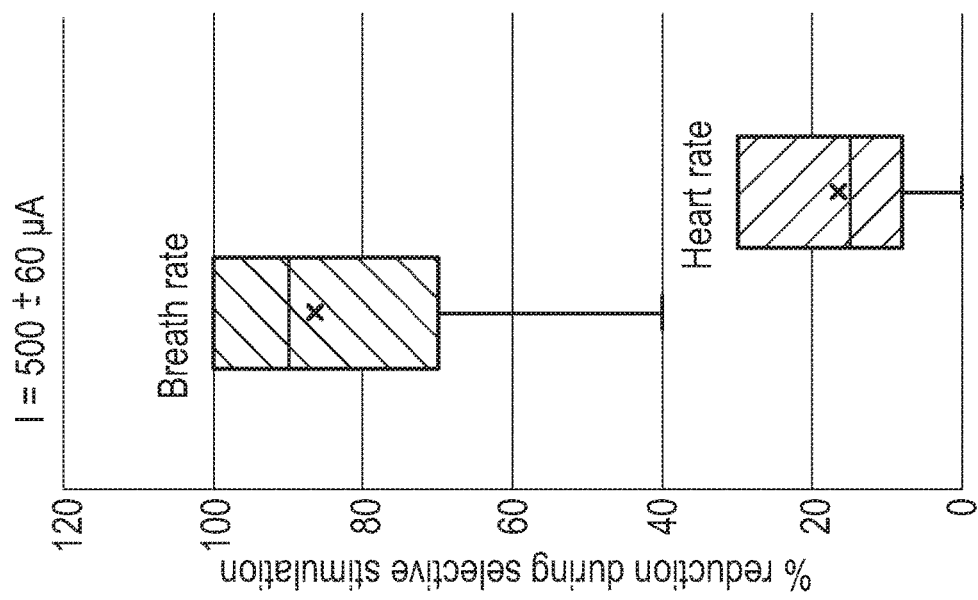
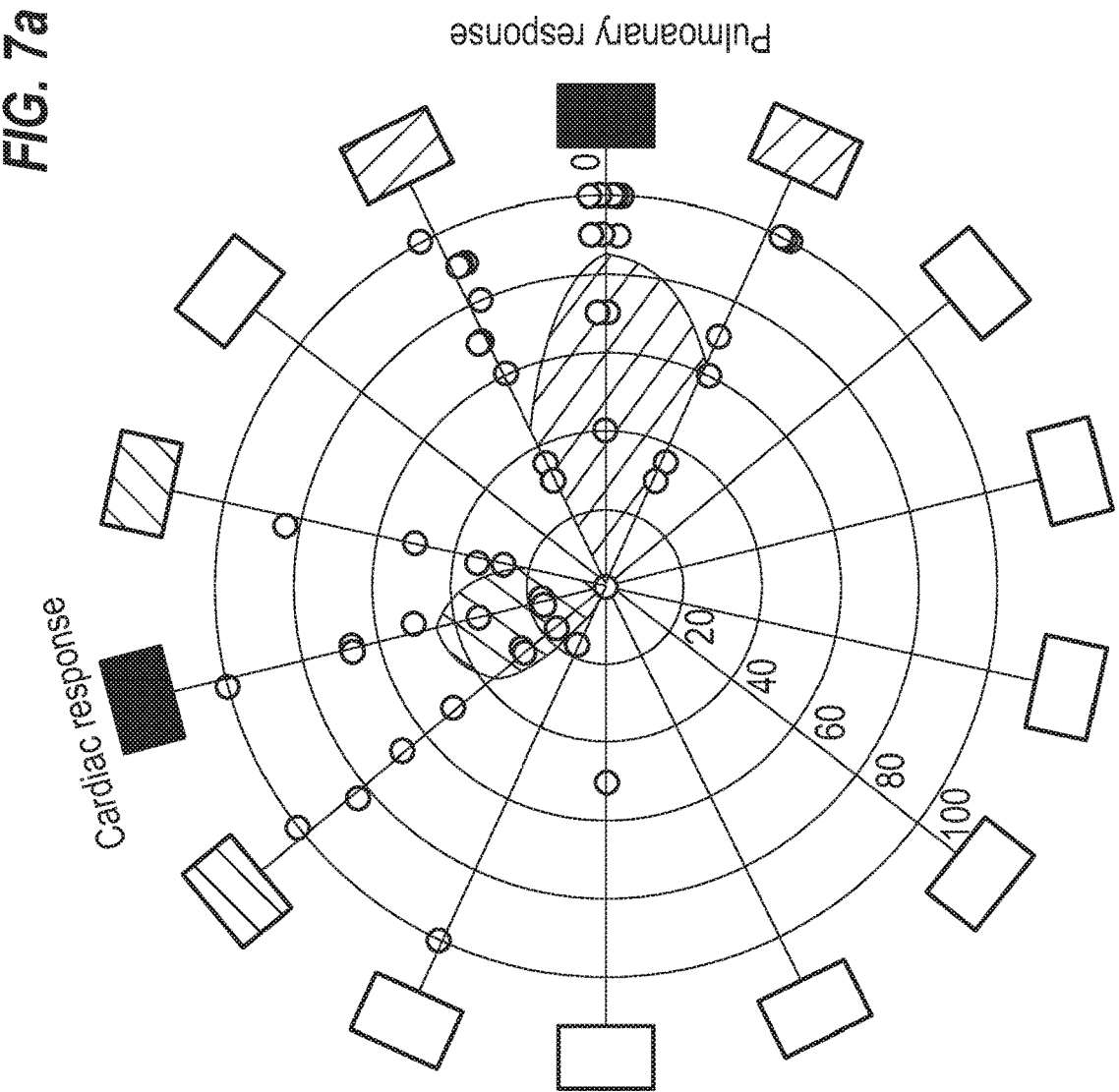
FIG. 7a

V ("votlatge vs spatial length")

Vxx ("activation function")

Line Graph Gradient of Vy, y component (mV/cm²)

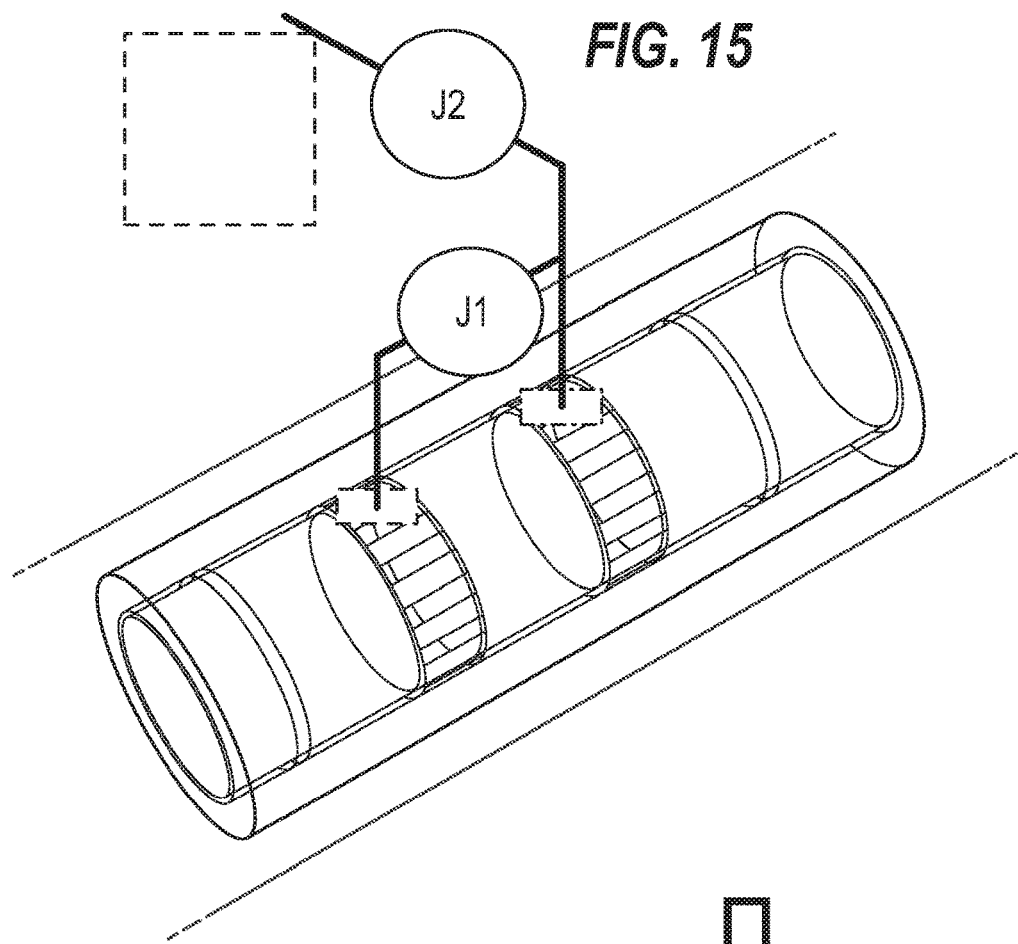
FIG. 15
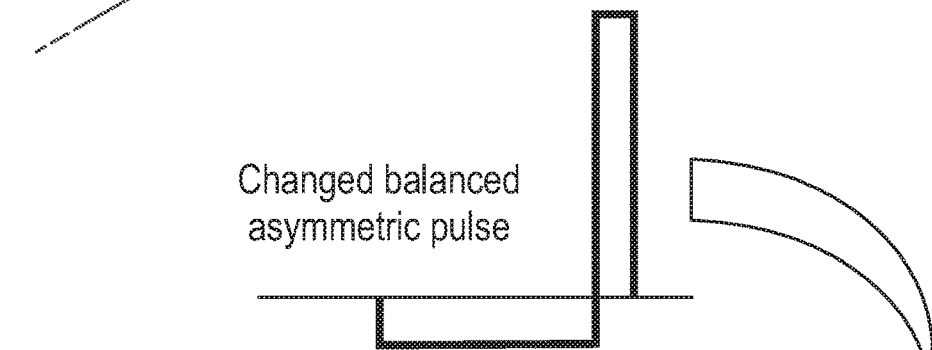
Changed balanced asymmetric pulse
FIG. 16
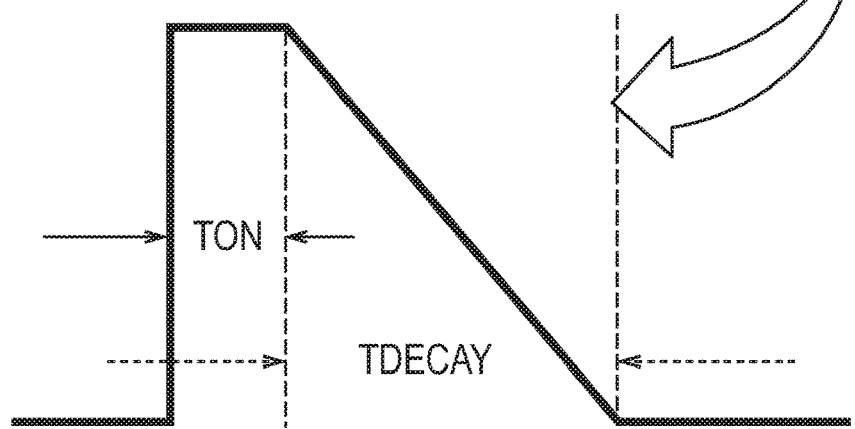
TON
TDECAY

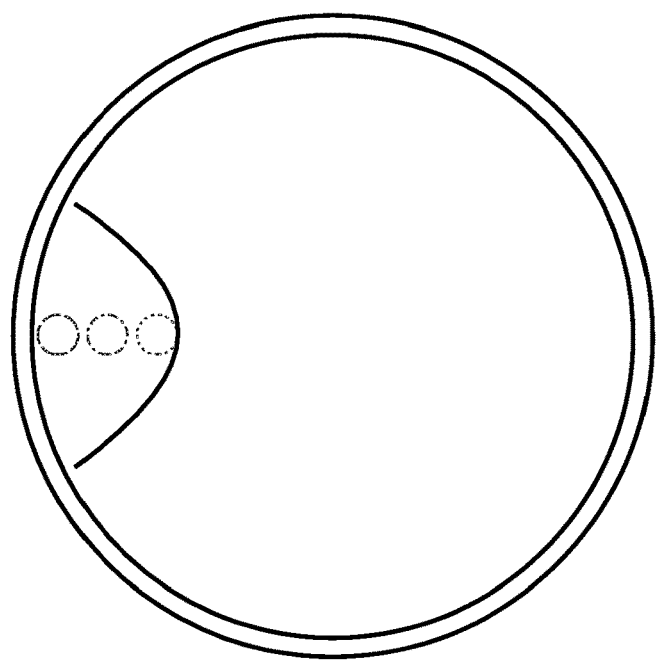
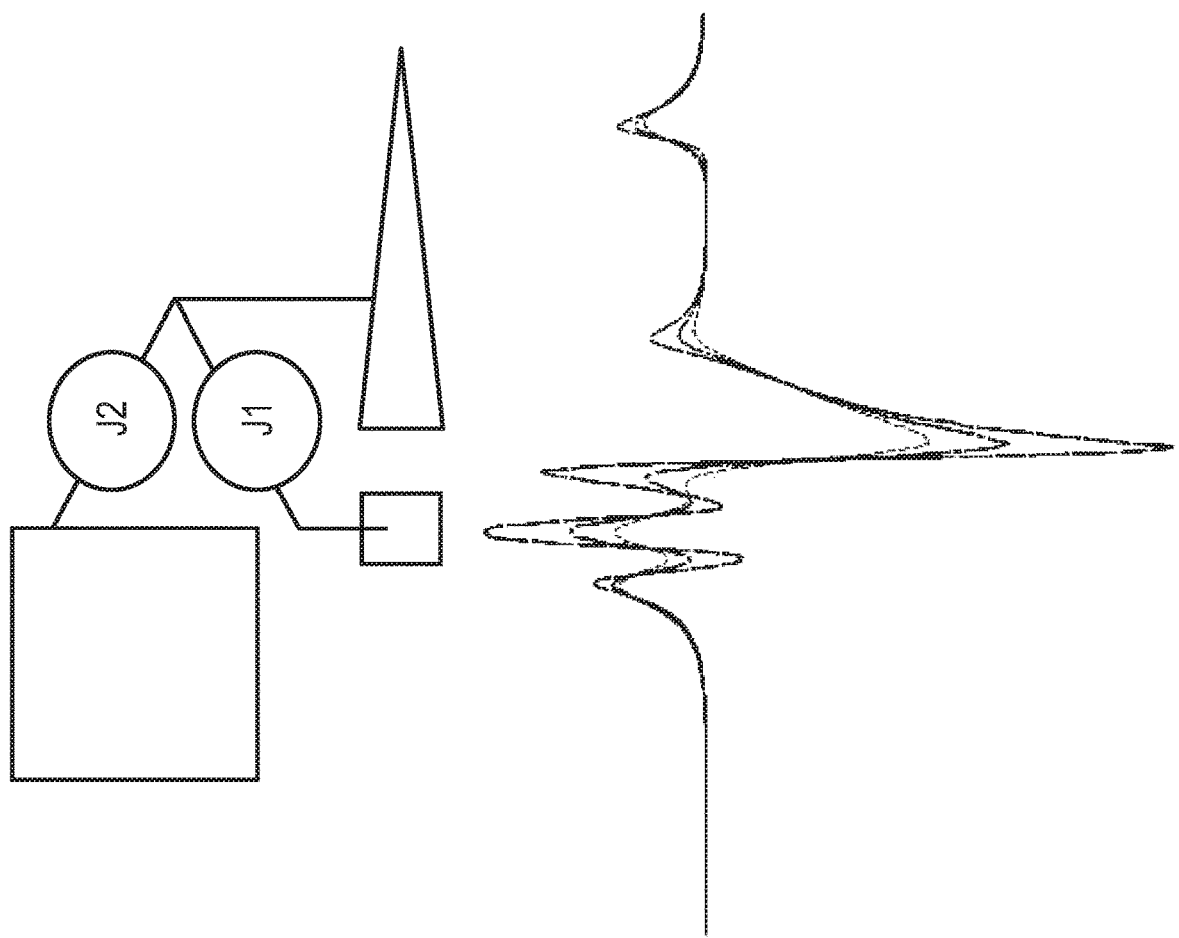
*FIG. 18*

Biphasic $I_1 = 800\ \mu A$, $I_2 = 0\ \mu A$
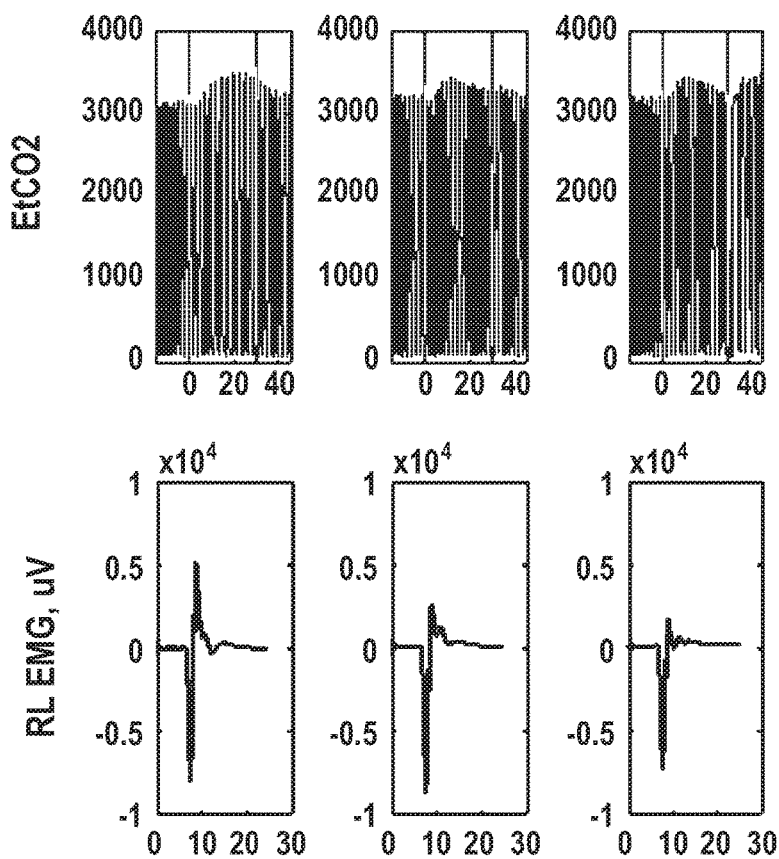
FIG. 19(i)
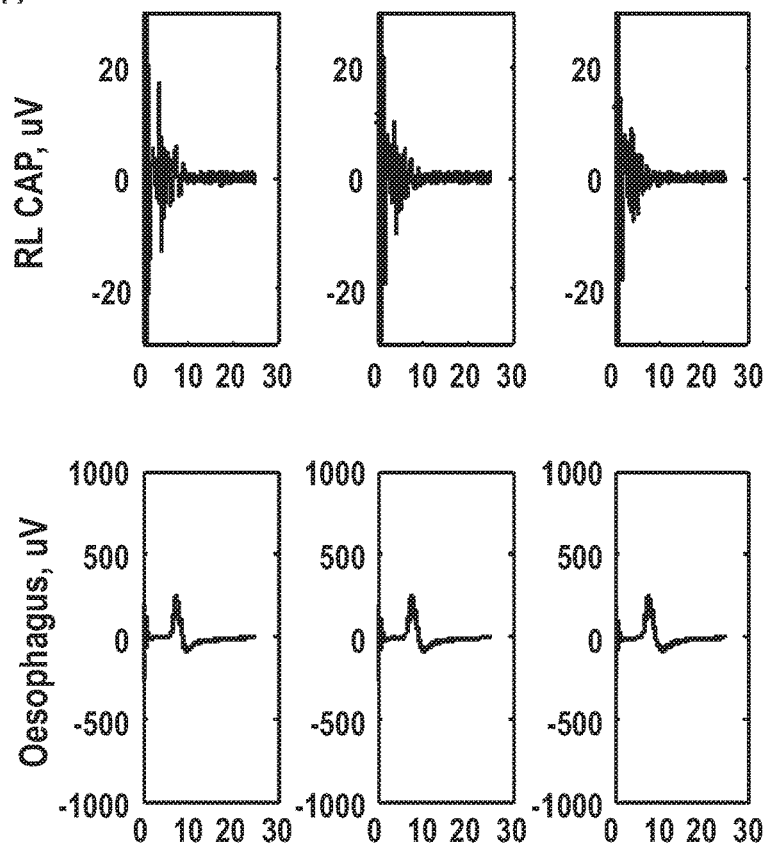

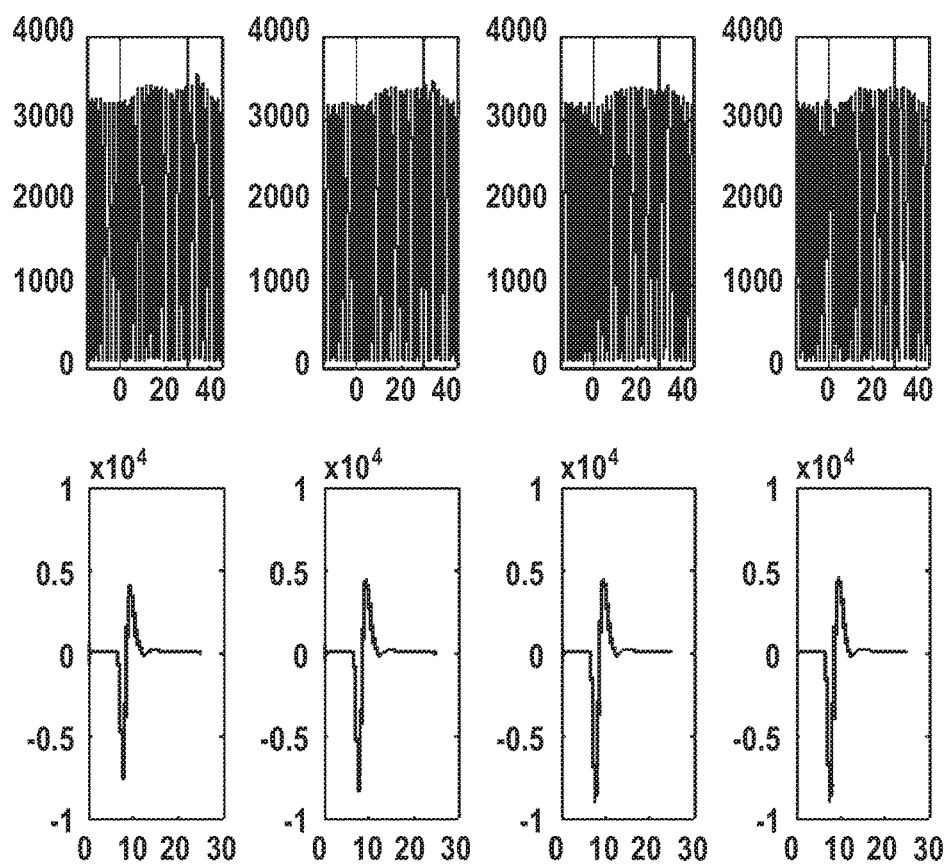
FIG. 19(iii)
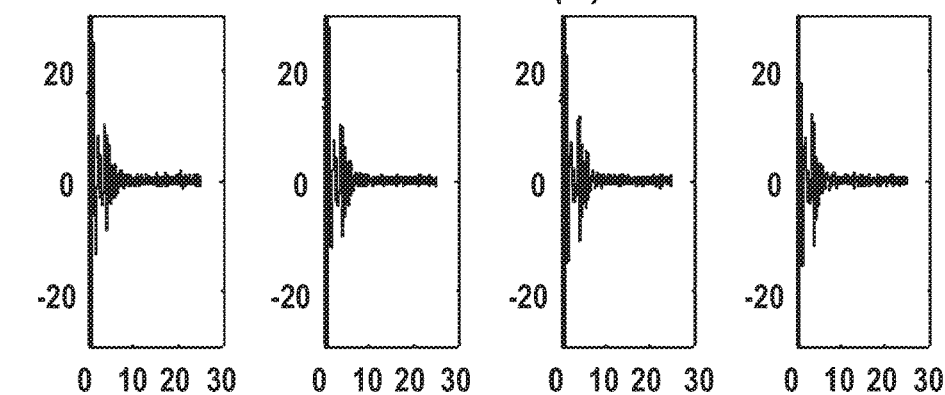
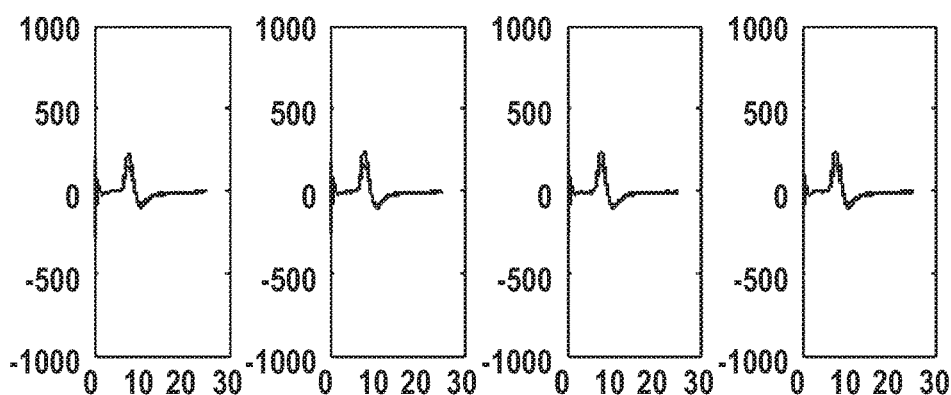

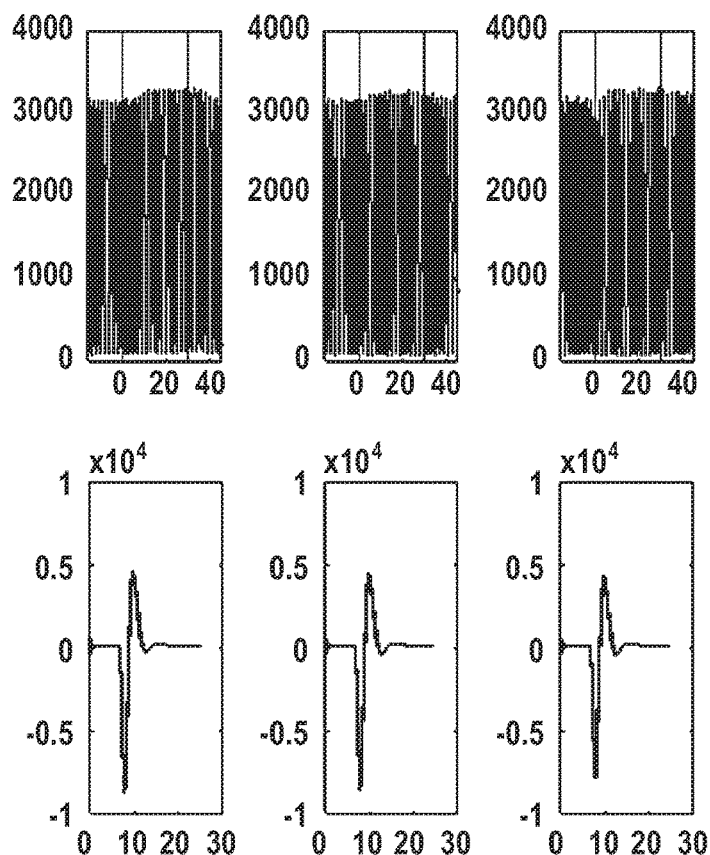
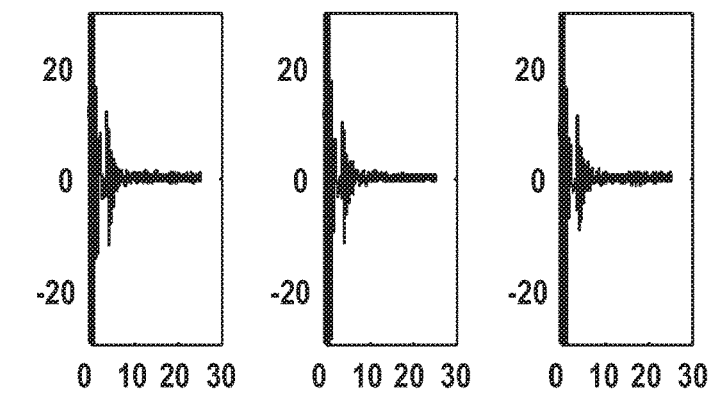
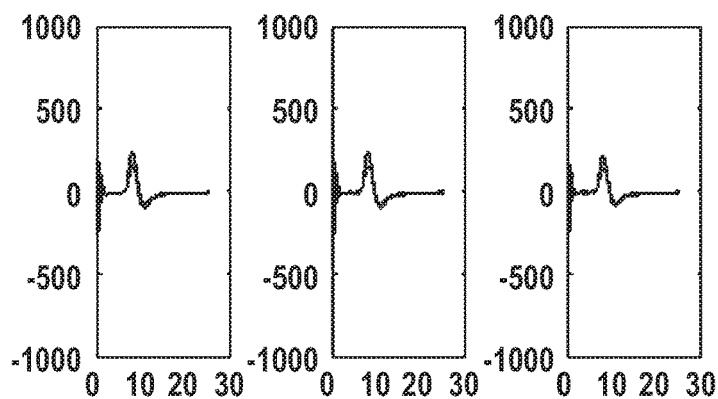
FIG. 19(iv)

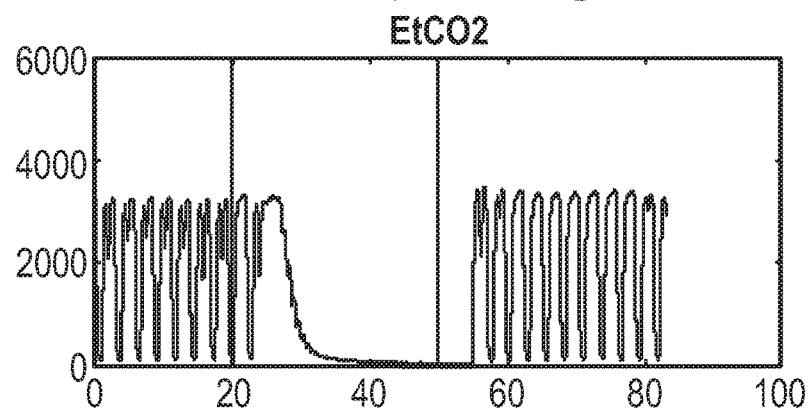
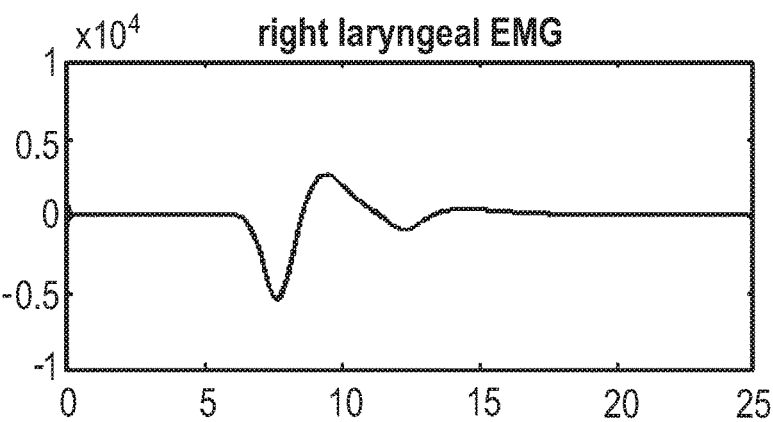
FIG. 20(ii)
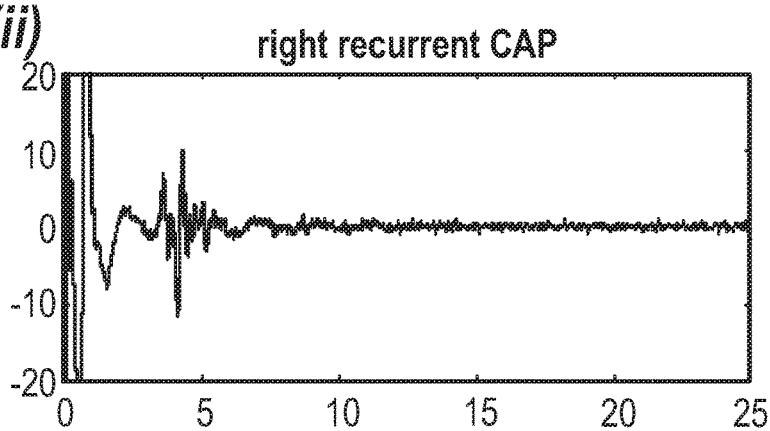
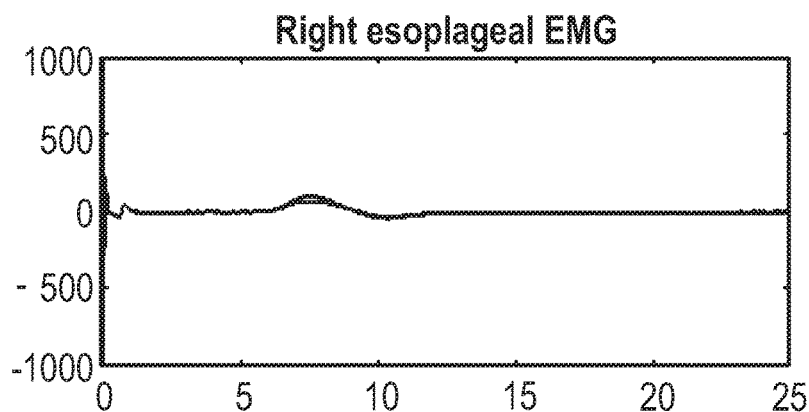

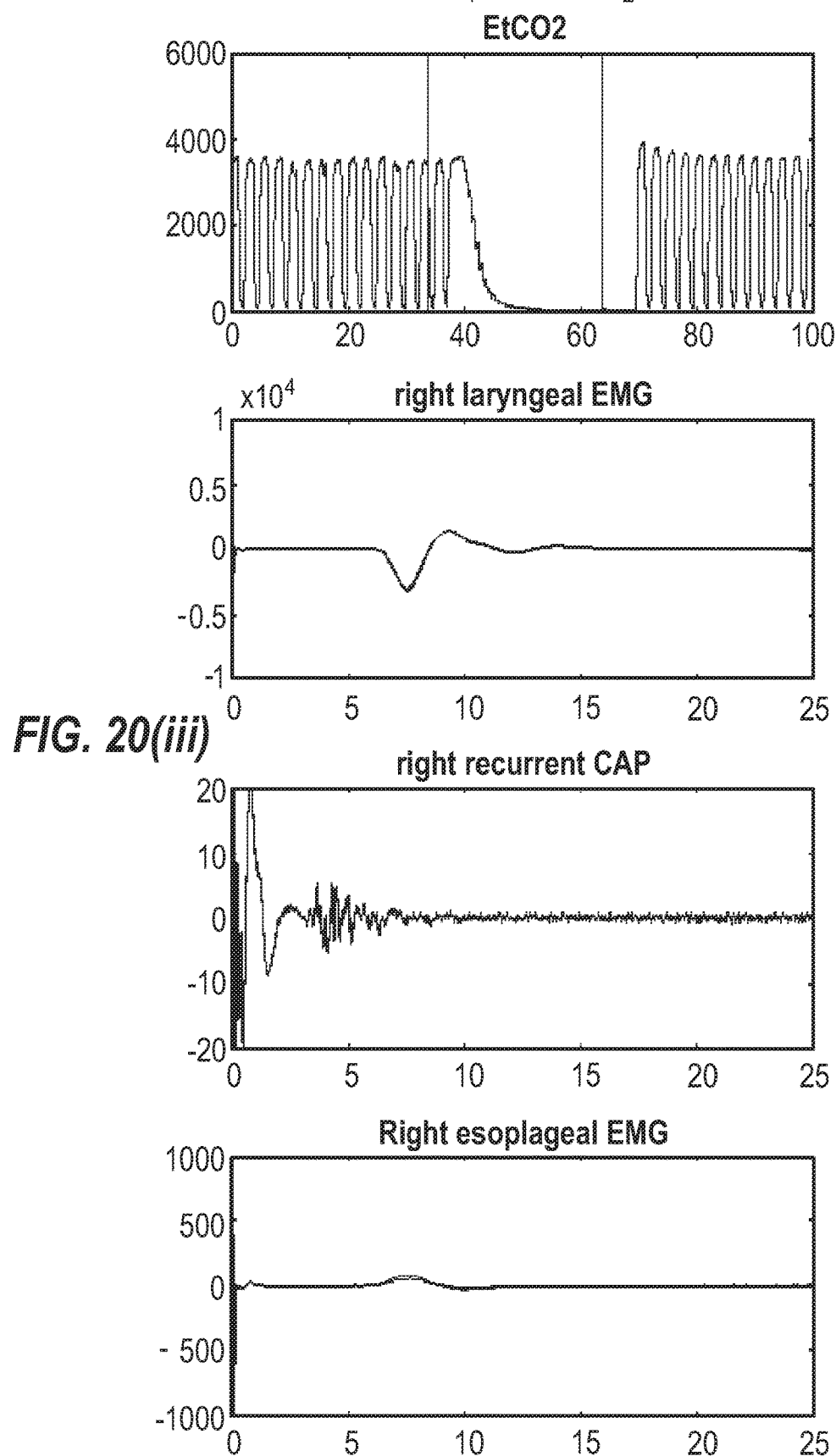
FIG. 20(iii)

Charged balanced asymmetric (CBA) pulse

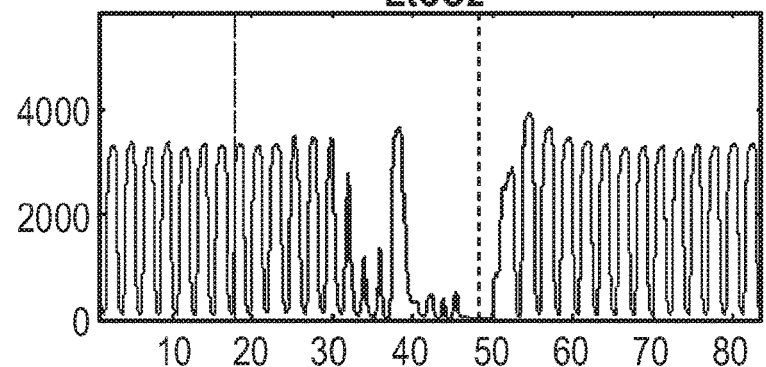
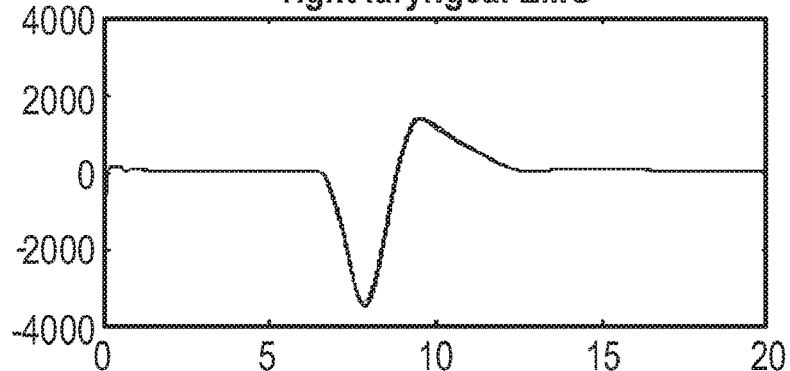
FIG. 21(ii)
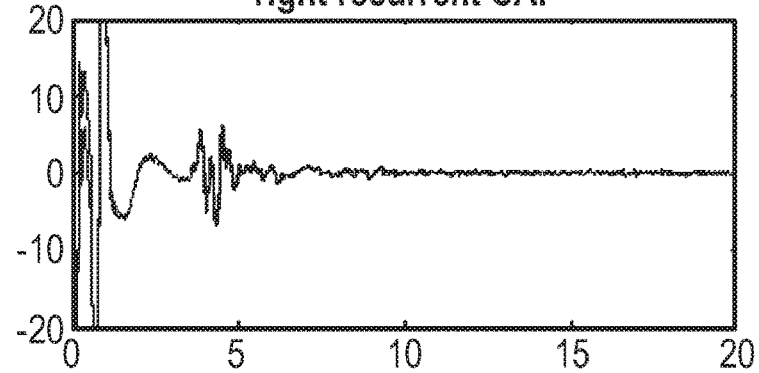
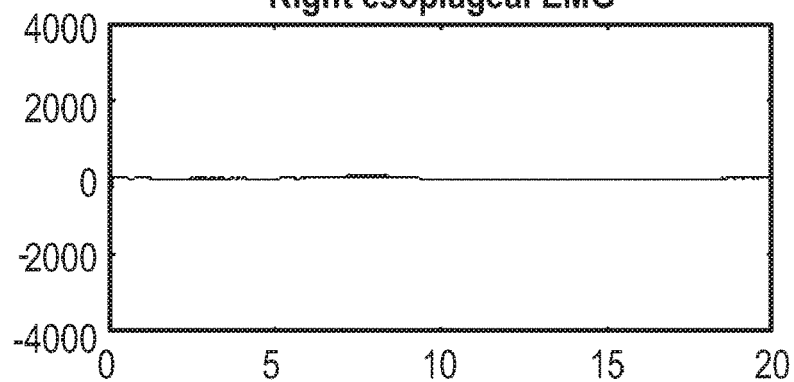

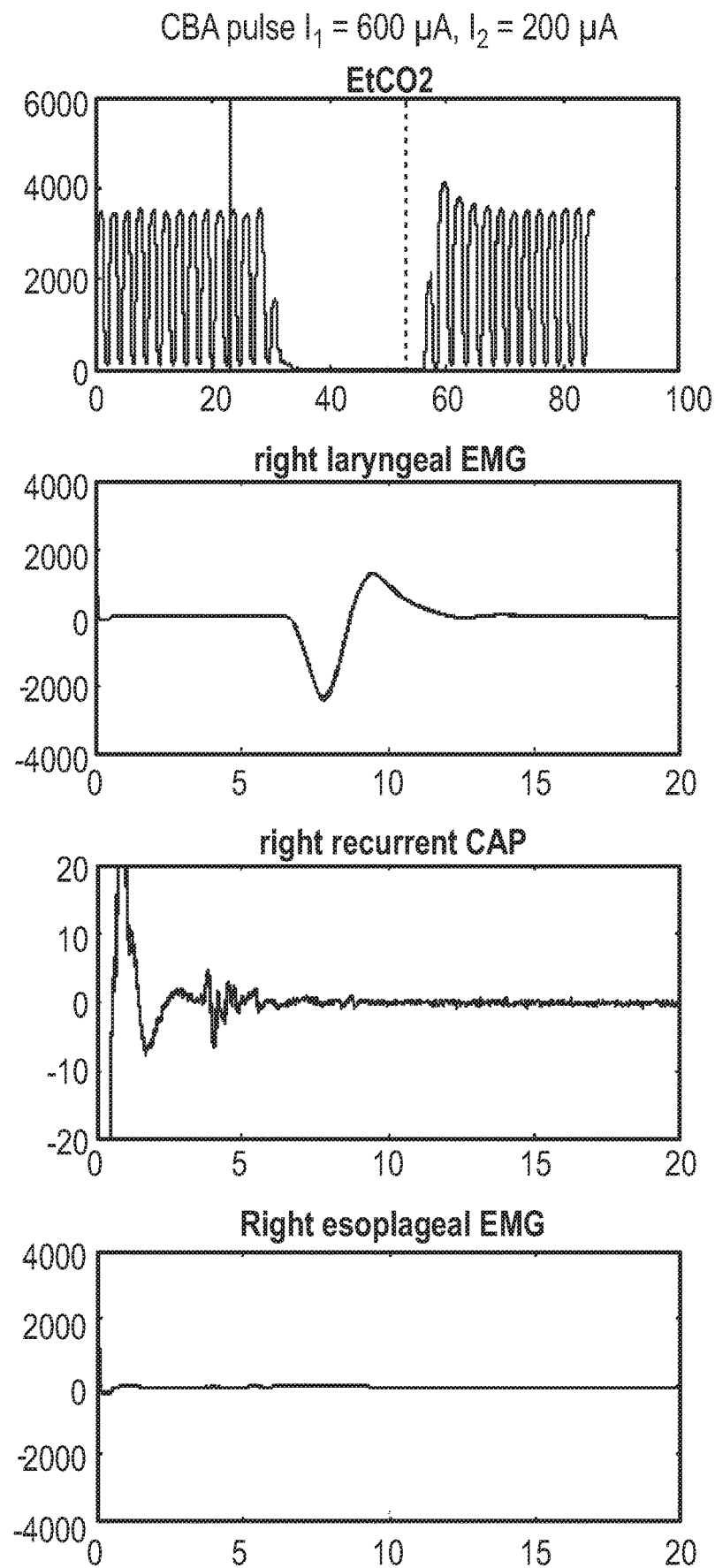
FIG. 21(iii)

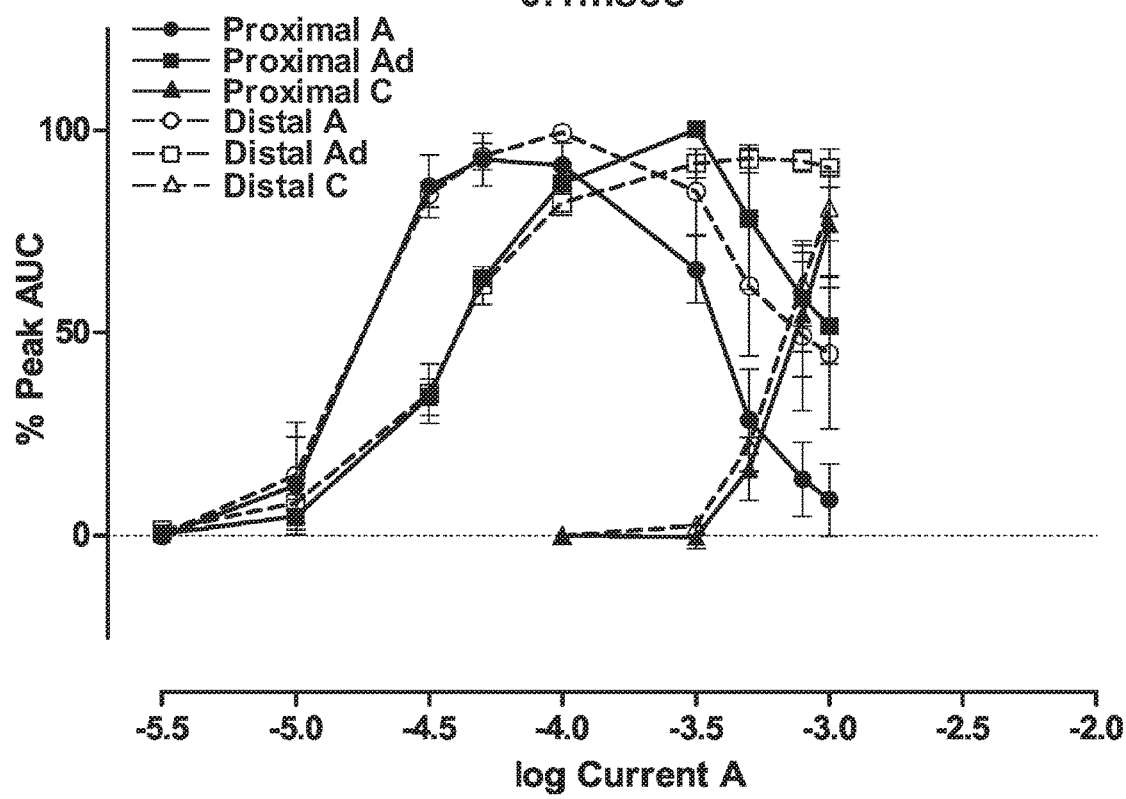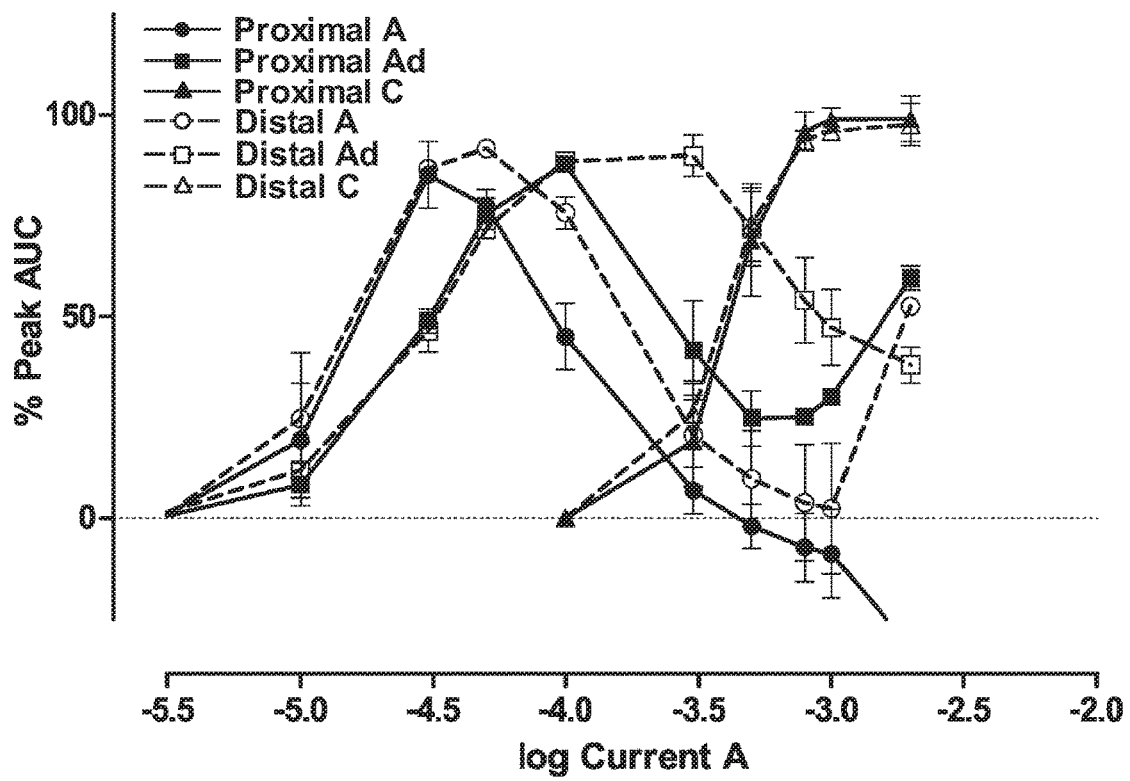

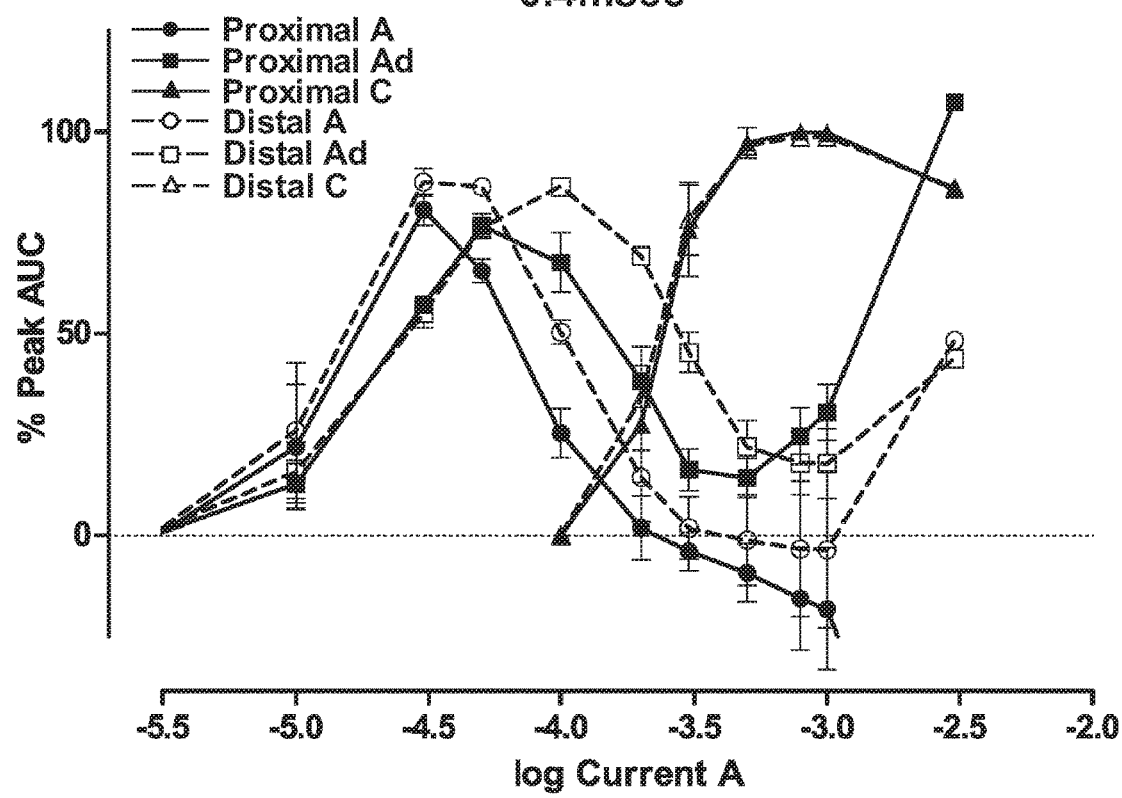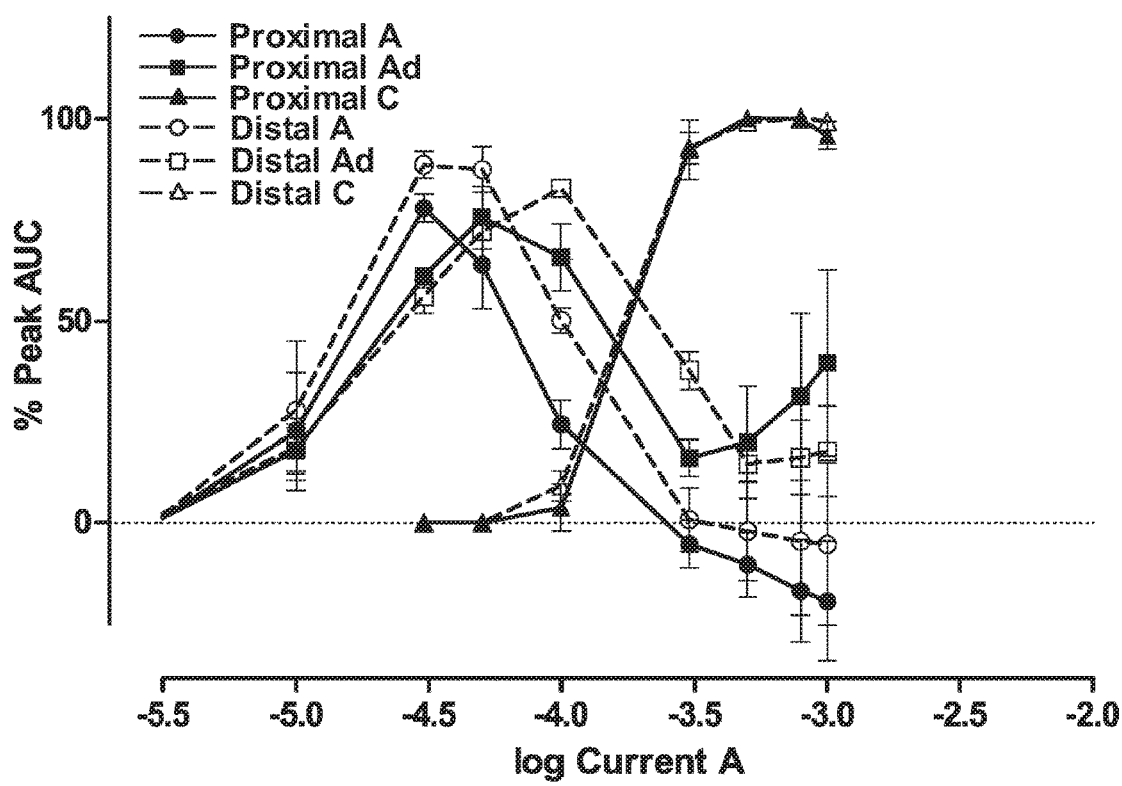

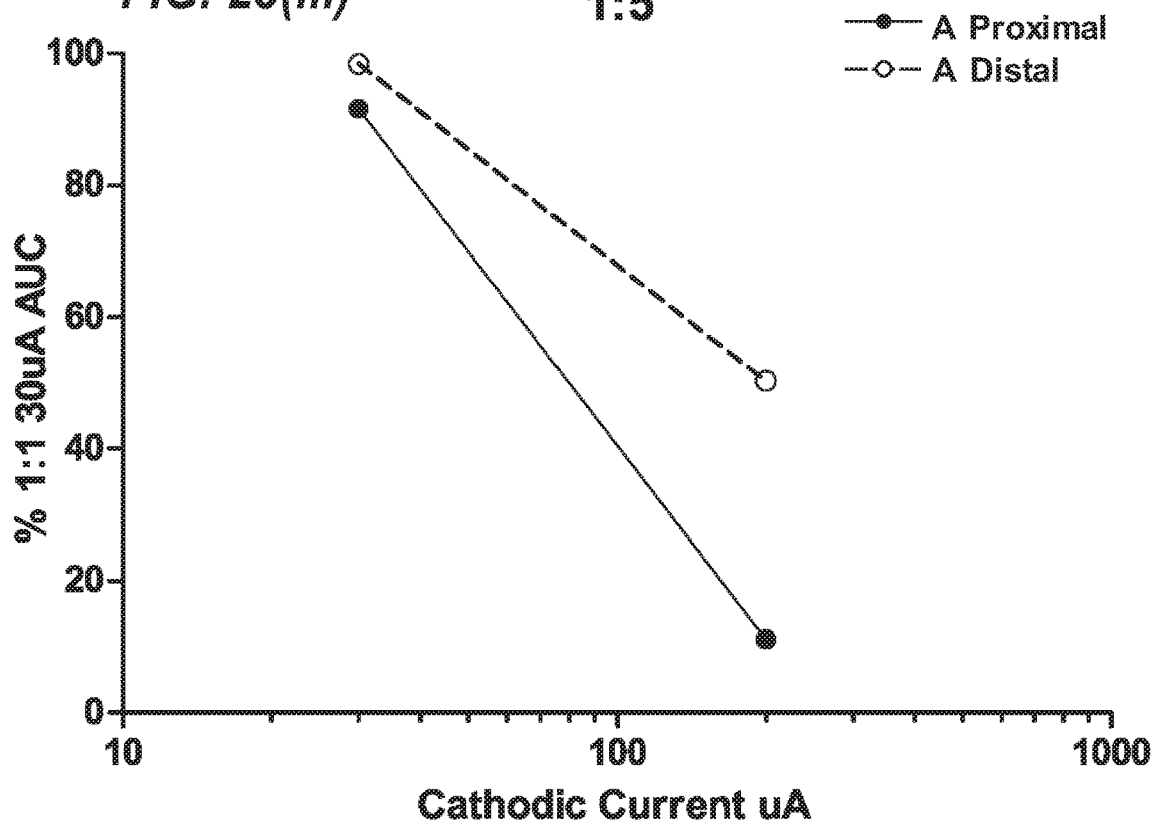
FIG. 28(iii)

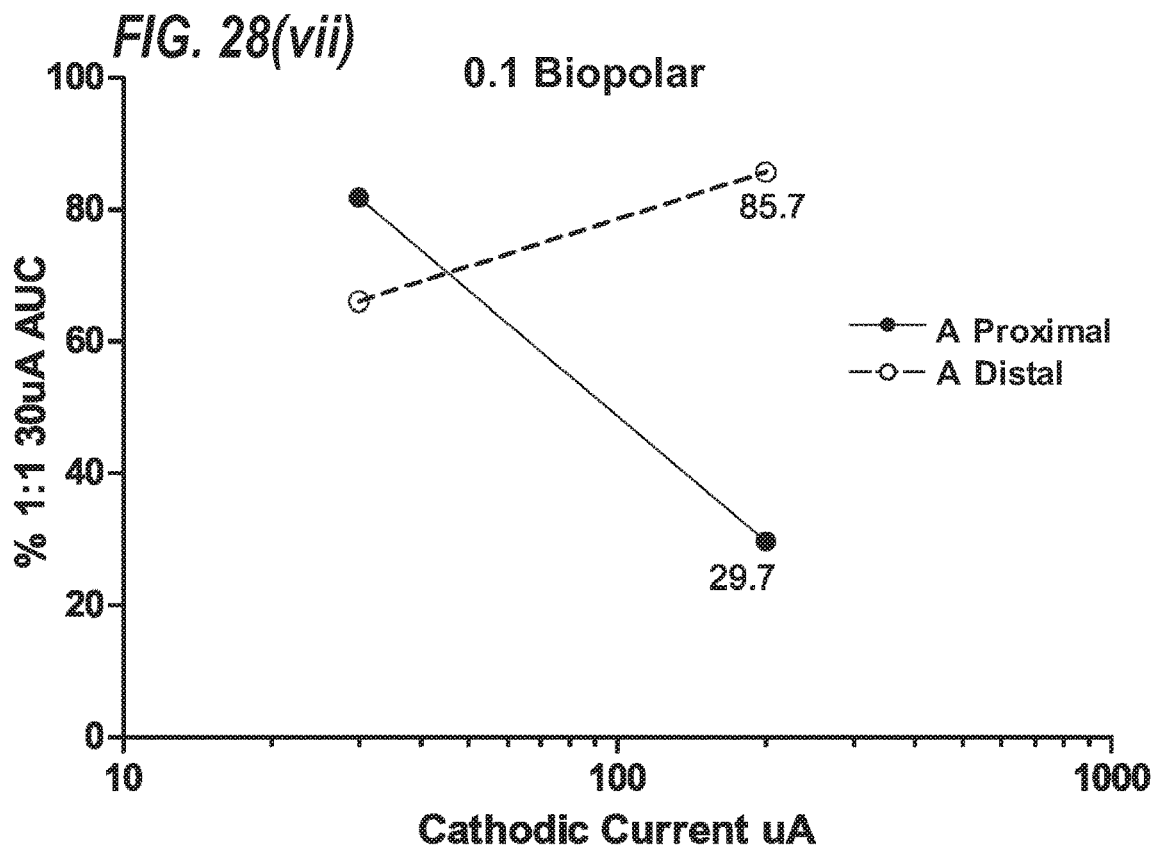
FIG. 28(vii)
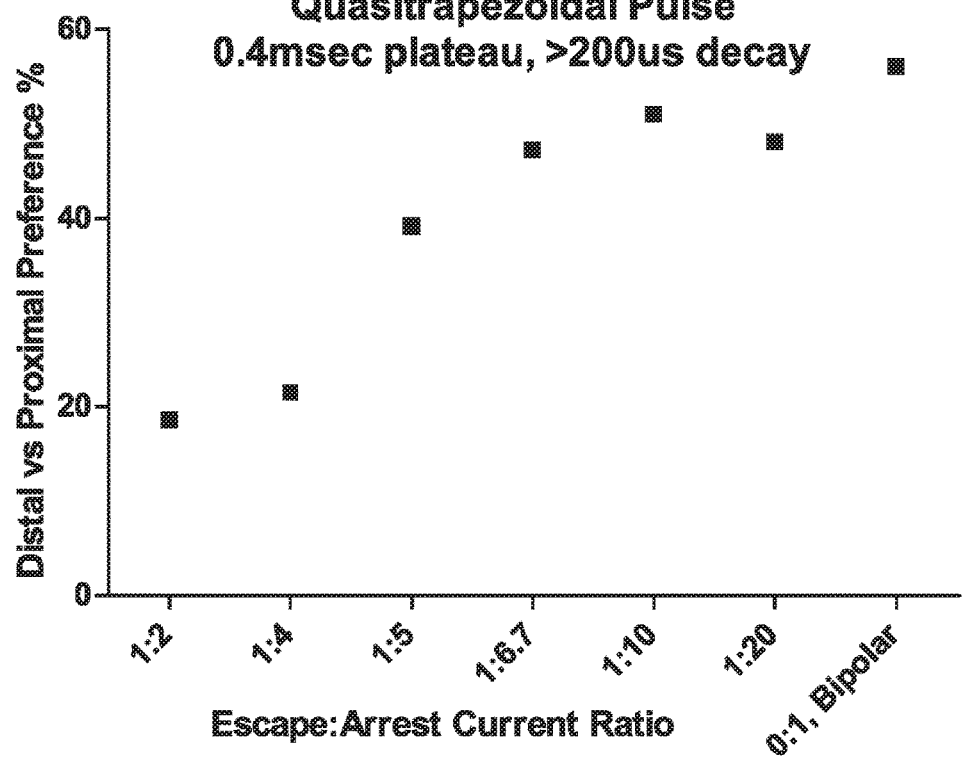
FIG. 28(viii)

NERVE STIMULATION DEVICE FOR UNIDIRECTIONAL STIMULATION AND CURRENT STEERING

PRIORITY CLAIM

The present application is a National Phase entry of PCT Application No. PCT/GB2018/053602, filed Dec. 11, 2018, which claims priority from U.S. Provisional Application No. 62/609,227, filed Dec. 21, 2017, each of which is hereby fully incorporated herein by reference.

TECHNICAL FIELD

This disclosure relates to a system, a method and a computer program for stimulating a nerve.

BACKGROUND

It is desirable to be able to selectively stimulate bundles of nerves or fascicles, within a complex nerve, which are specific to certain organs. This may allow certain responses in specific organs to be induced. The vagus nerve is an example of a complex nerve, and it is known that different fascicles within the vagus nerve may be stimulated in order to induce certain responses in different organs.

The desire to selectively stimulate bundles of nerves or fascicles, within a complex nerve, follows on from research that allows for the identification of organ specific fibers within a peripheral nerve. One known method for this involves inserting an electrode array with penetrating shanks into the nerve and recording local field potentials. The correlation of the recording of spontaneous local field potentials with physiological activity, such as ECG and respiration, allows the position of organ specific bundles to be determined. This known method has drawbacks because the insertion of electrodes into the nerve may result in the damage of fibers. This has potentially serious consequences.

Selective stimulation of specific fiber types within a mixed nerve (including myelinated and unmyelinated fibers) could provide higher specificity and lower side effects when targeting specific types of fibers to cause specific physiological responses. However, this can be difficult to achieve with known electrodes assemblies, such as the electrode ring described in WO 2016/170327. Furthermore, selective stimulation using penetrative electrodes is undesirable as outlined above.

It is known that different geometries of electrode are capable of stimulating different fiber types.

Furthermore, there is a desire for treatment by neural stimulation to be as minimally invasive as possible. Hitherto, treatment of multiple diseases by neural stimulation involved implanting a neural stimulation system for each treatment. Particularly in situations where such treatment takes place on the same nerve, particularly a complex nerve, such that available space is highly restricted, the use of multiple neural stimulation systems can be problematic. There is therefore a desire for more compact and less invasive neural stimulation systems, particularly for treatment of multiple diseases, particularly on complex nerves.

SUMMARY

In a first aspect, the present disclosure provides a nerve interface device comprising: at least one cuff portion having an assembled position in which the cuff portion forms at least part of a passageway for receiving a nerve along a longitudinal axis passing through the passageway; and first and second rings of electrodes mounted on the at least one cuff portion, each ring of electrodes comprising a plurality of electrodes, and wherein each electrode in the first ring has a corresponding longitudinally-aligned electrode in the second ring so as to form a plurality of pairs of electrodes spaced apart from each other along the longitudinal axis; wherein the plurality of pairs of electrodes includes at least a first pair of electrodes, the first pair of electrodes mounted on the at least one cuff portion; wherein the at least one cuff portion comprises an asymmetric configuration about a central axis perpendicular to the longitudinal cuff axis.

In the present disclosure, since there is an asymmetric configuration, it is possible to provide a signal to the nerve, which travels in a particular direction along the nerve. This can help to avoid off target effects, which may occur when signals travel in the direction of the brain as opposed to an organ being targeted.

BRIEF DESCRIPTION OF THE DRAWINGS

Embodiments of the disclosure will be described, by way of example, with reference to the following drawings, in which:

FIGS. 1a-c illustrate various examples of a nerve stimulation device for use with the present disclosure.

FIG. 3a illustrates an embodiment of application of nerve stimulation devices according to the present disclosure and FIG. 3b illustrates measurements of compound action potentials (CAP) measured in response to stimulation of a nerve using the nerve stimulation devices.

FIG. 5 illustrates the position of electrode pairs in the nerve stimulation devices.

FIG. 7A illustrates in vivo data obtained using an optimized design.

FIG. 15 illustrates an electrode configuration similar to that illustrated in FIG. 1a with the anode electrodes in one ring being stimulated with a different current source to the cathode electrodes in another ring.

FIG. 16 illustrates an example pulse applied to the electrode configuration illustrated in FIG. 15.

FIG. 18 illustrates experimental results for the electrode configuration of FIG. 17.

FIGS. 26A-D illustrate action potential propagation distal and proximal to a central electrode array when the electrode configuration described with reference to FIG. 22 is stimulated in a tripolar manner with a quasitrapezoidal pulse.

DETAILED DESCRIPTION

Described herein is a device, system and method that allows multiple specific nerve fibers to be selectively stimulated within a complex nerve such as the vagus nerve. This enables fibers to be targeted more precisely thereby treating diseases more effectively while avoiding off target effects, and enables treatment of multiple diseases.

For example, specific stimulation of pulmonary bundles of the vagus nerve could help treat asthma and other respiratory conditions, whilst avoiding side-effects on other organs. Alternatively, selective stimulation of descending c-fiber bundles could optimize the stimulation of visceral organs, without affecting the cardio-respiratory system. Also, selective stimulation could be used to avoid contraction of the thyroarytenoid (TA) muscle of the larynx, which is the most common and serious side-effect of current vagus nerve stimulators used to treat inflammatory diseases. This system may be provided in an implantable device.

Figure 1:
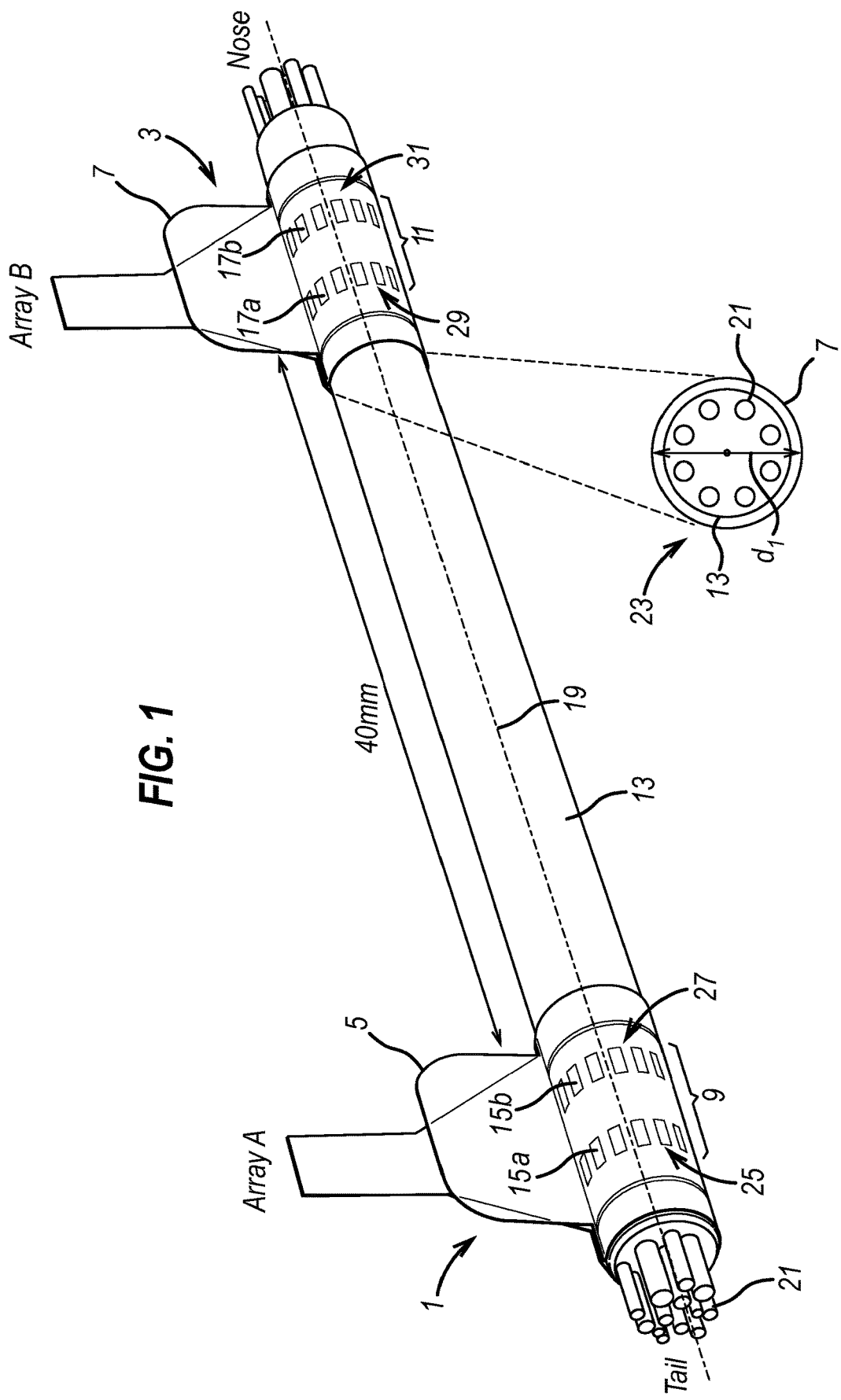
FIG. 1 illustrates examples of a nerve stimulation device.

Referring to FIG. 1, there is provided a first nerve stimulation device 1 (otherwise referred to as electrode array "A") and a second nerve stimulation device 3 (otherwise referred to as electrode array "B"). Each one of the arrays 1, 3 comprises a cuff portion 5, 7 upon which is provided a plurality of electrodes 9, 11. The provision of two devices 1, 3 is not essential and the benefits of the disclosure may be realized with just one.

The cuff portion 5, 7 is a flexible sheet with the electrodes 9, 11 mounted on the sheet. The sheet can be wrapped around a nerve of a subject 13, such that the electrodes 9, 11 form an electrical contact with the nerve at various points around the surface of the nerve 13. When the cuff is wrapped around the nerve 11, in its assembled position, the cuff forms an aperture (or tubular section/passageway) for receiving the nerve 13. As illustrated, the cuff 5, 7 receives the nerve along a cuff axis 19 (or longitudinal axis) which passes through the middle of the cuff 5, 7. This cuff axis 19 is also the longitudinal axis of the nerve 13.

As illustrated, in use the arrays 1, 3 can be separated from one another along the length of the nerve 13. In this example, the arrays 1, 3 are separated by a distance of 40 mm.

The electrodes may comprise stainless steel and can be fabricated by laser cutting the electrodes into a film. In one example, the film comprises silicon. However, other materials are also possible and equally effective.

As illustrated in the expanded cross-sectional view 23, the aperture formed by the cuff 7 has a diameter ($d_1$). The cuff axis 19 is perpendicular to the diameter and parallel with the depth of the aperture. In other words, the cuff axis is parallel with the depth of the tubular section. Furthermore, the pair of electrodes are offset from one another in a direction perpendicular to the diameter of the aperture and parallel with the depth of the aperture.

Each one of the arrays 1, 3 comprises a plurality of pairs of electrodes 15, 17. These electrode pairs 15, 17 are offset, or spaced apart, from one another in the direction of the cuff axis 19. Thus, the stimulation device can apply a signal to an electrode pair 15, 17 and induce a signal between the electrodes in the pair 15, 17 in a longitudinal direction along the nerve 11. In this way, an electrical channel is provided in the direction of the longitudinal axis 19 of the nerve. This can be used to stimulate specific nerve fibers 21 in the nerve 13, which may be associated with specific organs or physiological responses in the subject.

In this example, the plurality of electrodes in each array 1, 3 are mounted on the same cuff 5, 7. However, it may be possible to provide more than one cuff portion, with some electrode(s) provided on one cuff portion and some electrode(s) provided on another cuff portion.

Each one of the arrays 1, 3 comprises a first set of electrodes 25, 29 and a second set of electrodes 27, 31 mounted on the cuff portion. In the assembled position, the electrodes of first set of electrodes 25, 29 are mounted offset from one another in a direction perpendicular to the cuff axis; and the electrodes of second set of electrodes 27, 31 are mounted offset from one another in a direction perpendicular to the cuff axis 19. As illustrated, the electrodes of the first set of electrodes 25, 29 and the second set of electrodes 27, 31 are spaced in a ring around a circumference of the cuff 5, 7.

The electrodes of the first set of electrodes 25, 29 comprise a first electrode in a pair electrodes 15, 17, and the electrodes of the second set of electrodes 27, 31 comprise a second electrode in the pair 15, 17. The electrodes in each pair 15, 17 are offset from one another along the length of the nerve 11.

In each array 1, 3 the first set 25, 29 and/or the second set 27, 31 of electrodes may comprise 4 to 96 electrodes. However, in a specific example illustrated in FIG. 2, the first set of electrodes 25 and the second set of electrodes 27 of the first array 1 comprises 14 electrodes. Also, the first set of electrodes 25 and the second set of electrodes 27 of the second array 3 comprises 14 electrodes. As illustrated, each set of electrodes 25, 27, 29, 31 comprises a plurality of electrodes arranged sequentially to form a straight line of electrodes on the cuff sheet.

Figure 2:
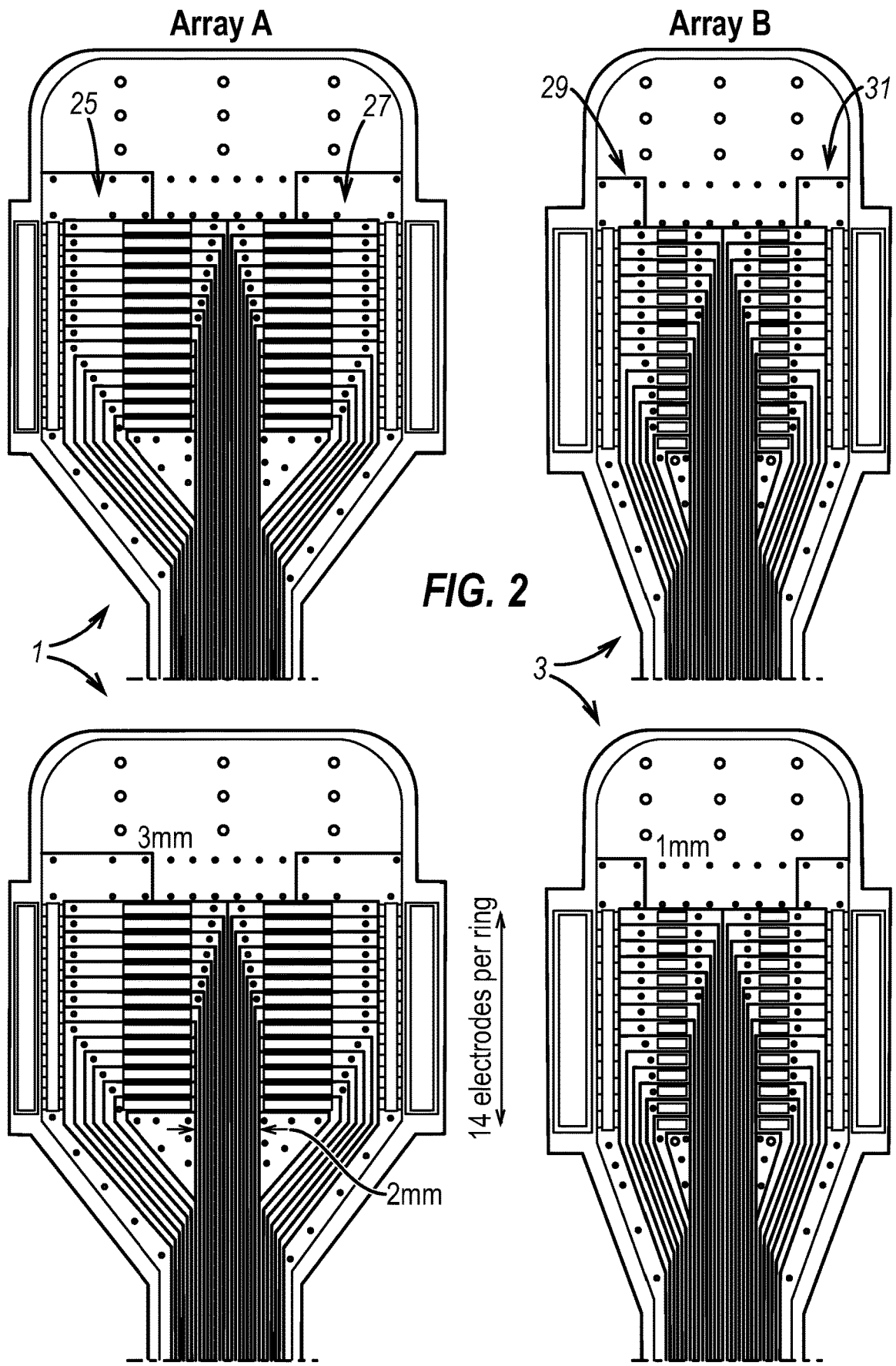
FIG. 2 illustrates schematic representations of the nerve stimulation devices.

FIG. 2 illustrates two schematic views of each of the electrode arrays 1, 3. Each of the electrodes in the arrays 1, 3 have a surface for making electrical contact with the nerve 13. In the first array 1, this surface is rectangular with a width of 0.2 mm and a length of 3 mm. In the second array 3, the surface is also rectangular with a width of 0.2 mm and a length of 1 mm. In another example array (not shown), each of the electrodes has a square surface. This square surface may be 0.2 mm wide and 0.2 mm long. In other words, the length is in the direction parallel to a longitudinal axis of a nerve and the width is in the direction perpendicular to a longitudinal axis of a nerve.

In each of the arrays 1, 3 illustrated in FIG. 2, the electrodes are paired. Each electrode in the first set 25, 29 is paired with an opposing electrode in the second set 27, 31. In the example illustrated, the electrodes in each pair are offset from one another by a distance of 3 mm. Thus, the first set of electrodes 25, 29 is offset from the second set of electrodes 29, 31 by a distance of 3 mm. This distance is measured in the direction of the cuff axis 19.

It will be appreciated that other distances between pairs/sets of electrodes could be used. For instance, the electrode pairs/sets may be offset from one another by a distance of 2 mm. In another example, the electrode pairs/sets may be offset from one another by a distance of 1 mm.

One or more of the arrays 1, 3 may be provided in a nerve stimulation system comprising a stimulation device (not shown) arranged to generate an electrical signal. In this example, the stimulation device is arranged for electrical communication with the first pair of electrodes 15, 17 or each of the plurality of pairs of electrodes of the first device. In this way, the stimulation device can provide an electrical signal to pairs of electrodes.

The stimulation device is capable of generating electrical signals with a variety of different properties. For example, the stimulation device may be arranged to generate signals each with a different pulse duration, frequency, pulse width and current. In addition, the stimulation device may be capable of generating a bipolar pulse.

In one example, the signal has a pulse width of 1 ms. The signal may have a frequency of 1-50 Hz frequency. More specifically, the signal may have a frequency of 2 Hz. The signal may have a pulse width of 50-1000 µs. A pulse width refers to a width (or time duration) of a primary phase of the waveform. In some cases where a pulse comprises a first phase that is the primary phase and a second phase which is the recovery phase, for example an anodic and/or a cathodic phase, the pulse width refers to a width (or duration) of the first phase. A pulse duration refers to the time duration during which the pulse is applied or delivered for. This may also be referred to as a stimulation time. The amplitude of the current of the signal may be between 100 µA-50 mA.

In another example, the signal has a current of 500 µA, a pulse width of 0.1 ms and/or a frequency of 5 Hz. In yet another example, the signal has a frequency of 20 Hz and/or a duration of 60 seconds.

With reference to FIG. 1a, in embodiments of the first aspect of the disclosure, the stimulation device 30 is configured to generate electrical signals for applying to the electrode pairs.

The nerve stimulation system further comprises a control device 32 which causes the stimulation device 30 to deliver electrical signals to the electrode pairs.

Purely by way of example, and with reference to FIG. 3a, a specific application of a nerve stimulation system according to the disclosure is shown. Here, a cross section of a cervical vagus nerve in the sheep is shown. Stimulating the vagus nerve with an 800 µA, 5-20 Hz frequency, 0.05 ms pulse width signal can yield a number of different physiological responses, including cardiac effects, laryngeal effects and pulmonary effects. Through testing, nerve bundles or fascicles within the cervical vagus nerve were identified as being particularly effective for specific responses. For instance, fascicles within the cervical vagus nerve that were identified as being particularly effective for cardiac effects (i.e. reduction in heart rate) were found to be anatomically opposite (i.e. around 180° from, or more specifically separated by around 100-120° from) fascicles also within the cervical vagus nerve that were identified as being particularly effective for pulmonary effects (change in expiratory time and/or respiratory rate). Similarly, fascicles within the cervical vagus nerve that were identified as being particularly effective for laryngeal effects were found positioned between (i.e. 90° away from) both of the fascicles that were identified as being particularly effective for laryngeal effects and the fascicles that were identified as being particularly effective for pulmonary effects. In other words, fascicles within the cervical vagus nerve that were identified as being particularly effective for laryngeal muscle activation were found positioned around the same area of the fascicles that were identified as being particularly effective for cardiac effects.

In general, electrically induced compound action potentials are generated if the depolarization under the cathode is sufficient to increase local membrane potentials past the activation threshold for voltage-gated sodium channels from the resting membrane potential. The activation threshold is typically around −40 mV, and the resting membrane potential is typically around −70 mV. Thus, the difference between the activation threshold and the resting membrane potential is around Δ30 mV.

Once the activation threshold is passed and the NaV channels (also known as "voltage-dependent" sodium channels) are opened, positively charged sodium ions flow down their concentration gradient into the cell until reaching their reversal potential (which is typically around +50 mV). This local influx of positively charged sodium ions, which is the first phase of the action potential, initiates a wave of depolarization in both directions along the axon axis, opening adjacent NaV channels, thus propagating an action potential in both directions. This wave of depolarization can locally be greater than ~Δ100 mV (resting membrane potential to reversal potential), but likely less due to passive diffusion between nodes of Ranvier. In order to arrest this propagation at a second point along the axon axis, electrical hyperpolarization, via a positively charged anode, must be employed to reduce the resting membrane potential ($E_{rest}=$−

70 mV) to a point that the incoming wave of depolarization (~Δ100 mV) is insufficient to reach the threshold potential ($E_{thres}$=−40 mV). Therefore for arrest to occur, the resting membrane potential would need to be hyperpolarized by −70 mV from the previous resting state. This is illustrated in following equation:

$$\Delta 100 \text{ mV}-(E_{thres}-E_{rest})=100 \text{ mV}-(-40 \text{ mV}-(-70 \text{ mV}))=-70 \text{ mV}=\Delta 70 \text{ mV hyperpolarization}$$

Therefore, the electrode charge density required to generate an action potential (i.e. to induce ~Δ30 mV depolarization to threshold) is always lower than the charge density required to arrest an action potential (induce ~Δ70 mV hyperpolarization) when the anode and cathode have the same surface area. When using anode or cathode pairs with symmetric surface area, charge density for a given current injection will be equal and opposite on each electrode. This will generate a bell shaped activation/arrest profile as charge density and current increase.

By introducing surface area differences between the electrodes in the pair, one can concentrate or reduce charge on any given electrode. When reducing the anode surface area compared to the cathode, charge density is increased under the anode for any given current injection compared to the cathode. This allows arrest to occur at lower currents than can be achieved in electrodes with equal surface areas. In conjunction, this surface area differential reduces cathodal charge density for a given current injection. This shifts activation to higher currents. The reduction of block current threshold due to anode surface area reduction and increase in activation current threshold due to cathode surface area increases can together result in a convergence of block and activation with the same current. Thus, an effective treatment can be provided with a reduced current to achieve block (where block is preferred) compared to electrodes with equal surface area.

Figure 1C:
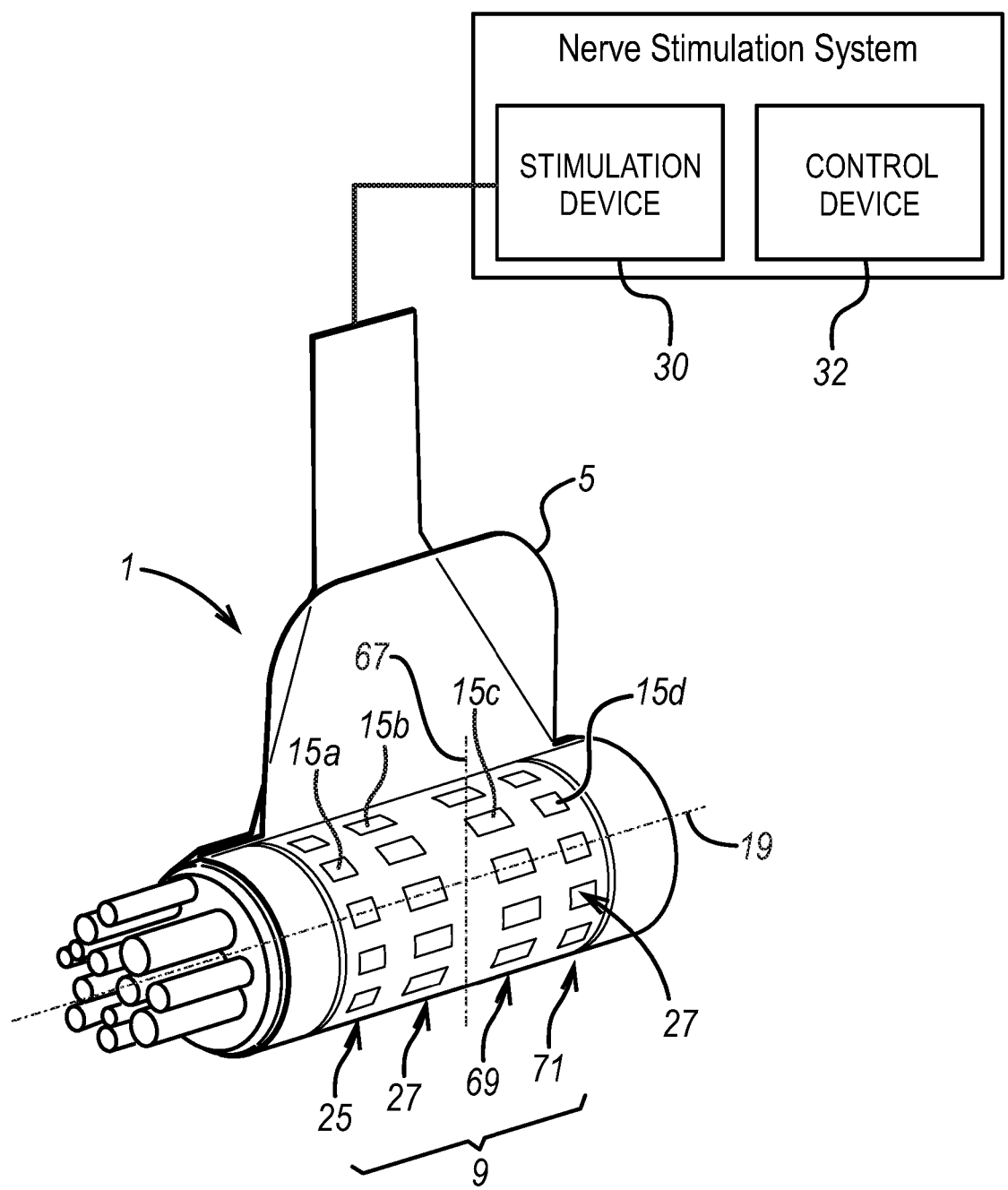

Referring to FIGS. 1a-c, there are arrays 1 which are arranged for providing stimulation to a nerve in a particular direction (or, in other words, to provide unidirectional stimulation) using the above described principle of increasing charge density under one of the electrodes, in this example the anode. Each array 1 is asymmetric about a central axis 67 which is perpendicular to the longitudinal cuff axis 19. The central axis 67, may be described as being located in a central position along the length of the cuff 5. For instance, the central axis 67 may be positioned in the middle of the length of the cuff, or the central axis 67 may bisect the cuff 5 into two portions of equal length.

Referring to FIG. 1a, there is an array 1 with a first ring of electrodes 25 comprising a first electrode 15a, and with a second ring of electrodes 27 comprising a second electrode 15b. The first electrode 15a and the second electrode 15b are in a first pair mounted on opposing sides of the central axis 67. In this example, the first electrode 15a is different to the second electrode 15b. This helps to provide stimulation in a specific direction along the nerve. Specifically, the first electrode 15a is configured to have a first surface area in contact with the nerve in the assembled position, and the second electrode 15b is configured to have a second surface area in contact with the nerve in the assembled position. The first surface area may be different to the second surface area. For instance, the first surface area may be larger than the second surface area, or the second surface area may be larger than the first surface area. Thus, allowing unidirectional stimulation to be achieved.

Referring to FIG. 1a, there is an electrode configuration for creation of unidirectional action potentials in the nerve, which is a bipolar 'active/dispersive surface area' configuration comprising a first electrode and a second electrode, where the first electrode is positioned along the nerve axis distal to the brain and the second electrode is positioned along the nerve axis proximal to the brain relative to the first electrode. The surface area of the first electrode which is in contact with the nerve is greater than the surface area of the second electrode in contact with the nerve.

In this configuration, when an electrical signal is applied to the first electrode such that it becomes negatively charged (cathode) and an electrical signal is applied to the second electrode such that it becomes positively charged (anode), the smaller surface area of the anode in comparison to the surface area of the cathode results in an unbalanced current density which strengthens an anodal block. Consequently, the action potentials are greater in the direction away from the brain. Thus, this configuration describes stimulation preferentially down the nerve away from the brain. It will be appreciated by those skilled in the art that the cuff may be positioned or the cathode and anode arrangement may be configured to achieve any preferred directionality. For example, stimulation in the direction away from the brain may be preferential in cases of epilepsy treatment, whereas stimulation in the direction toward the brain may be preferential when trying to avoid recurrent laryngeal activation.

The surface area of the first electrode is adapted to be larger than the surface area of the second electrode to concentrate charge density under the second electrode, thus strengthening the hyperpolarization of the nerve without increased energy requirements. Thus, the length of the first electrode (in the longitudinal direction) is greater than the length of the second electrode (in the longitudinal direction). For example, the length of the first electrode (in the longitudinal direction) may be at least twice the length of the second electrode (in the longitudinal direction).

In bipolar electrode arrangements, the length of the first electrode (in the longitudinal direction) may also be less than or equal to five times the length of the first electrode (in the longitudinal direction. This is to increase blocking efficiency of the second electrode.

Thus, in a bipolar electrode arrangement, the length of the first electrode may be set at any value between the upper and lower limits described above. For example, the length of the first electrode may be one of: 2.0, 2.5, 3.0, 3.5, 4.0, 4.5 or 5.0 times the length of the second electrode.

The electrode configuration, shown in FIG. 1a, for creation of unidirectional action potentials in the nerve may be a bipolar 'balanced surface area' configuration, where the first electrode is positioned along the nerve axis distal to the brain and the second electrode is positioned along the nerve axis proximal to the brain relative to the first electrode. The surface area of the first electrode which is in contact with the nerve may be equal in size to the surface area of the second electrode in contact with the nerve. In this configuration, when an electrical signal is applied to the first electrode such that it becomes negatively charged (cathode) and an electrical signal is applied to the second electrode such that it becomes positively charged (anode), and when the pulse width of the electrical signals applied is tuned with the inter-electrode distance for fiber type conduction velocities (so the anode is on when an action potential reaches it), the escaping action potentials are greater in the direction away from the brain.

The nerve is stimulated by the first electrode such that two compound action potentials, which propagate in opposite directions along the nerve, are generated in the nerve under the first electrode. Once one of the compound action potentials reaches the second electrode, it is impeded such that it cannot propagate along the nerve any further, leading to unidirectional stimulation from the first electrode in the direction away from the second electrode. Thus, the first electrode and second electrode are positioned along the nerve respectively in the direction of the unidirectional stimulation. Put another way, the first electrode is at the "escape end" of the neural interface device, from which compound action potentials caused by applying the electrical signal may propagate. The second electrode, on the other hand, is at the "arrest end" of the neural interface device, from which compound action potentials cannot propagate.

In particular, a compound action potential is impeded by adapting the pulse width of the electrical signal applied to the nerve based on the size of the gap between pairs of electrodes in the longitudinal direction of the cuff. More specifically, the size of the gap between the first electrode and the second electrode is set so that one of the compound action potential generated in the nerve under the first electrode arrives at the second electrode when hyperpolarization of the nerve is present. This impedes the compound action potential from propagating along the nerve any further.

According to the disclosure, compound action potentials are impeded by adapting the pulse width of the electrical signal applied to the nerve based on the size of the gap between pairs of electrodes in the longitudinal direction of the cuff.

In particular, the pulse width may be set above a lower limit. The lower limit for the pulse width is the size of the gap between the stimulation and arresting pair of electrodes in the longitudinal direction plus the length of the first electrode, then divided by the slowest conduction velocity of the action potentials wishing to be targeted. The pulse width may be any value above the lower limits.

Referring to FIGS. 1b and 1b', there is an array 1 with a first ring 25, a second ring 27 and a third ring 69 of electrodes. The three rings 25, 27, 69 of electrodes form a plurality of triplets of electrodes spaced apart from each other along the longitudinal axis. The plurality of triplets comprises a first electrode 15a, a second electrode 15b and a third electrode 15c, and the first electrode 15a and the third electrode 15c are mounted on opposing sides of the central axis 67. The first electrode 15a is spaced apart from the second electrode 15b by a first gap, and the second electrode 15b is spaced apart from the third electrode 15c by a second gap. In this example, the first gap is different to the second gap, and thus provides an asymmetrical configuration that allows unidirectional stimulation to be achieved. For instance, the first gap may be larger than the second gap, or the second gap may be larger than the first gap. In another example, referring to FIG. 1b, the first electrode 15a is arranged to provide a different charge to the charge arranged to be provided by the third electrode 15c, which provides the asymmetry in this example.

Referring to FIG. 1b, the configuration for the creation of unidirectional action potentials in the nerve is a tri-polar 'passive imbalance' configuration. The second electrode is positioned along the nerve axis proximal to the first electrode and the third electrode is positioned along the nerve axis proximal to the second electrode. The first electrode is distal to the brain, and the third electrode is proximal to the brain.

The electrode configuration may employ asymmetric spatial variance to provide a passive imbalance such that the spacing between the first electrode and the second electrode is greater than the spacing between the second electrode and the third electrode. In this configuration, when an electrical signal is applied to the first electrode and the third electrode such that they become positively charged (anode) and an electrical signal is applied to the second electrode such that it becomes negatively charged (cathode), and when the pulse width of the electrical signals applied is tuned with the inter-electrode distance for fibre type conduction velocities, there is an impedance mismatch conveyed by the current path length along the nerve. The third electrode has a larger current density than the first electrode. The action potentials are therefore greater in the direction away from the brain. The neural interface devices may comprise a dual current source and tri-polar electrode arrangements with different insulation spacing.

The distance between the first electrode and the second electrode may be referred to as the width of the first gap $g_1$. The distance between the second electrode and the third electrode may referred to as the width of the second gap $g_2$. This second gap $g_2$ may be specially adapted for unidirectional stimulation. A compound action potential is impeded under the first electrode by adapting the pulse width of the electrical signal applied to the nerve based the width of the first gap $g_1$. This is so that the compound action potential generated under the second electrode arrives in the nerve under the first electrode when hyperpolarization of the nerve is present. In order for the compound action potential travelling in the opposite direction along the nerve not to be impeded under the third electrode, the nerve under the third electrode should not be hyperpolarized when the compound action potential arrives. In some embodiments, the neural activity of the nerve under the third electrode has returned to baseline activity upon arrival of the compound action potential, allowing the compound action potential to pass unimpeded. This can be achieved by adapting the width of the second gap $g_1$ based on the width of the first gap $g_1$.

The width of the second gap $g_2$ may be greater than the sum of the width of the first gap $g_1$ and the length of the second electrode.

Another exemplary electrode configuration for creation of unidirectional action potentials in a nerve is a tri-polar 'active, current balance' configuration comprising a first electrode, a second electrode and a third electrode. The second electrode is positioned along the nerve axis proximal to the first electrode and the third electrode is positioned along the nerve axis proximal to the second electrode, where the spacing between the first electrode and the second electrode is the same in length as the spacing between the second electrode and the third electrode. The first electrode is distal to the brain, and the third electrode is proximal to the brain. Additionally, the surface area of the first electrode in contact with the nerve is equal in size to the surface area of the second electrode in contact with the nerve, and to the surface area of the third electrode in contact with the nerve. Two independent non-equal current sources in the IPG provide positive currents to the first electrode and the third electrode respectively and the second electrode shares or sums the negative lead from both current sources. In this configuration, the current source of the first electrode provides a greater current than the current source of the third electrode such that the third electrode becomes more positively charged (anode) than the first electrode. The second electrode, which shares both current sources, becomes negatively charged (cathode). The current density mismatch between the first and third electrodes steers action potentials in the direction away from the brain.

Neural interfaces may comprise a dual current source and tri-polar electrode arrangements with different insulation spacing.

The surface area of the second electrode can be adapted to be larger than the surface area of the first electrode so that charge density is concentrated under the first electrode, thus strengthening the hyperpolarization of the nerve without increased energy requirements. Thus, the length of the second electrode $x_2$ (in the longitudinal direction) is greater than the length of the first electrode $x_1$ (in the longitudinal direction). In particular, the length of the second electrode $x_2$ can be at least twice the length of the first electrode $x_1$. This is because the charge applied by the second electrode to the nerve in a tri-polar electrode arrangement is split between the first electrode and the third electrode, meaning that the second electrode is required to apply at least twice the amount of charge to the nerve than in the bipolar electrode arrangement. The second electrode therefore has at least twice the surface area than the first electrode.

In a tri-polar electrode arrangement, the length of the second electrode $x_2$ may also be less than or equal to ten times the length of the first electrode $x_1$.

Thus, in a tri-polar electrode arrangement, the length of the second electrode length $x_2$ may be set at any value between the upper and lower limits described above. For example, the length of the second electrode $x_2$ may be one of: $2.0x_1$, $2.5x_1$, $3.0x_1$, $3.5x_1$, $4.0x_1$, $4.5x_1$, $5.0x_1$, $5.5x_1$, $6.0x_1$, $6.5x_1$, $7.0x_1$, $7.5x_1$, $8.0x_1$, $8.5x_1$, $9.0x_1$, $9.5x_1$ or $10.0x_1$. Typical values for the length of the first electrode $x_1$ are described above.

The length of the third electrode $x_3$ may be at least the length of the first electrode $x_1$. This is so that more of the charge applied to the nerve by electrical signal, via the second electrode, propagates in the direction towards the first electrode (i.e. the direction of stimulation) than towards the third electrode. In other words, the strength of the compound action potential propagating in the direction of the unidirectional stimulation is greater than the compound action potential propagating in the opposite direction.

Referring to FIG. 1c, there is an array 1 with a first ring 25, a second ring 27, a third ring 69 and a fourth ring 71 of electrodes. The first and second rings 25, 27 form a first plurality of pairs spaced apart from each other along the longitudinal axis, while the third and fourth rings 69, 71 form a second plurality of pairs spaced apart from each other along the longitudinal axis. In this case the middle pair of rings (i.e. the second ring 27 and the third ring 69) depolarize the nerve, while the outer pair of rings (i.e. the first ring 25 and the fourth ring 71) hyperpolarize the nerve. The spacing between the pairs of adjacent rings and/or the surface area of the electrodes in of adjacent rings can be adjusted to cause asymmetric hyperpolarization in order to provide unidirectional stimulation.

Referring to FIG. 1a, there is a first insulation portion 73 positioned towards a proximal end of the cuff portion 5 and a second insulation portion 75 positioned towards a distal end of the cuff portion 5. The first insulation portion 73 and the second insulation portion 75 are arranged to contact the nerve in the assembled configuration. The size of first insulation portion 73 arranged to contact the nerve is different to the size of the second insulation portion 75 arranged to contact the nerve.

Referring to FIG. 1a, there is first central offset between the central axis 67 and a first electrode 15a of the first pair, and a second central offset between the central axis 67 and a second electrode of the first pair 15b. The first central offset is different to the second central offset. The first central offset may be described as the distance between the central-most end of the first electrode 15a and the middle of the cuff 5. The second central offset may be described as the distance between the central-most end of the second electrode 15b and the middle of the cuff. The middle of the cuff is designated by the central axis 67.

Referring to FIG. 1a, there is a first radial offset between the longitudinal cuff axis 19 and a first electrode 15a of the first pair, and a second radial offset between the cuff axis 19 and a second electrode 15b of the second pair. The asymmetrical configuration may be provided by the first radial offset being different to the second radial offset. The first radial offset may be described as the distance between the surface of the first electrode 15a arranged to contact the nerve and the longitudinal axis of the cuff 19, passing through the middle of the cuff 5. The second radial offset may be described as the distance between the surface of the second electrode 15b arranged to contact the nerve and the longitudinal axis of the cuff 19, passing through the middle of the cuff 5. This provides a bipolar 'recessed electrode' configuration.

The number of electrodes in each ring and the width of each electrode (i.e. the width of each electrode around the circumference of the cuff) is dependent on the circumference of the nerve in question (e.g. the vagus nerve is typically around 6-7 mm in diameter) and on the average diameter of the nerve fascicles (e.g. the average diameter of the nerve fascicles in the vagus is around 200 um). The distance between each adjacent electrode within the same ring should be approximate to the width of each electrode. This helps to ensure that selective fascicular stimulation is possible.

The number of electrodes in each ring is defined by the following equation:

Number of electrodes=half of the circumference of the nerve in question ($2\pi(R/2)$/width of the fascicle within the nerve For instance, if the vagus nerve has a diameter of 2 mm and the fascicles have an average diameter of 0.2 mm, then using the equation above (i.e. 2*Pi*Radius/0.2*2) provides the optimum number of electrodes to be used in each ring. This number may be the minimum number of electrodes necessary to obtain spatial selectivity at the fascicular level and thereby obtain a specific physiological effect.

The system may also comprise a physiological sensor arranged to detect physiological activity in a subject. This sensor may be used to detect activity in the subject such as heart rate or EMG activity in a muscle.

In one example application, the control system may be configured to deliver a first signal every 20 minutes. Of course, this time period is only exemplary and shorter or longer time periods are possible depending on application and including every 20 minutes, 30 minutes, 1 hour, 2 hours, 3 hours, 4 hours, 6 hours, 12 hours, 24 hours, 48 hours, 72 hours, week and month. The control system may be configured to deliver a second signal according to the same or a different schedule. Where the schedule is the same, it may be offset in time such that the delivery of the first and second signals is not taking place simultaneously.

In another example application, the control system may be configured to deliver a first signal upon receipt of a first trigger, wherein the trigger is user-initiated. For example, the first signal may be suitable for treating a disease whose symptoms are perceptible by a user such as anxiety or pain. A user device such as a portable interface (not shown), or a smartphone or watch loaded with software configured to communicate with the nerve stimulation system may be used to generate the user-initiated trigger by pressing a button. The control system may be configured to deliver a second signal upon receipt of a second trigger, wherein the trigger is generated by (or the result of data from) a physiological sensor arranged to detect physiological activity in a subject. For example, a physiological sensor may be configured to detect heart rate and a trigger activated when heart rate increases beyond a threshold, for example.

It will be appreciated that any combination of schedules and triggers may be used, depending on circumstances.

In one example application, the electrodes of the arrays are placed on the right vagus nerve of anesthetized adult sheep and stimulation is applied between electrode pairs. In this example, the arrays are arranged in a similar fashion to that illustrated in FIG. 1 with the nerve 13 being the vagus nerve of the sheep.

FIG. 3b illustrates a number of charts which show the response induced in the nerve 13 when stimulation was applied to the electrode pairs. Charts 35 and 37 illustrate the compound action potential (CAP) measured in the nerve of different sheep when stimulation was applied to electrode pairs of the second array 2. On the other hand, charts 39 and 41 illustrate the CAP measured in the nerve of different sheep when stimulation was applied to electrode pairs of the second array 2. Referring to FIG. 3b, the peak appearing at around 10 ms of delay in the nerve recording represents a EMG contamination from the contraction of the trachea and larynx (laryngeal muscles), pronounced in the 3 mm electrode.

It was found that in any of the electrode pairs of the second array 3, the 1 mm long electrodes mostly elicited fast fiber response (myelinated fibers). In addition, it was found that the longer electrode arrays of the first array 1 stimulated both slow (small myelinated and unmyelinated) and fast fibers, but with a much higher proportion of slow fibers (small myelinated and unmyelinated) being stimulated. This was found when either the same current or the same charge density were applied in either one of the electrode arrays.

Furthermore, it was found that the first array 1 was able to reliably cause bradypnea (slow breathing) when stimulating the vagus nerve. On the other hand, the second array 2 always failed to achieve this (with any of the tested combination of electrodes) even at much higher charge densities.

Figure 4:
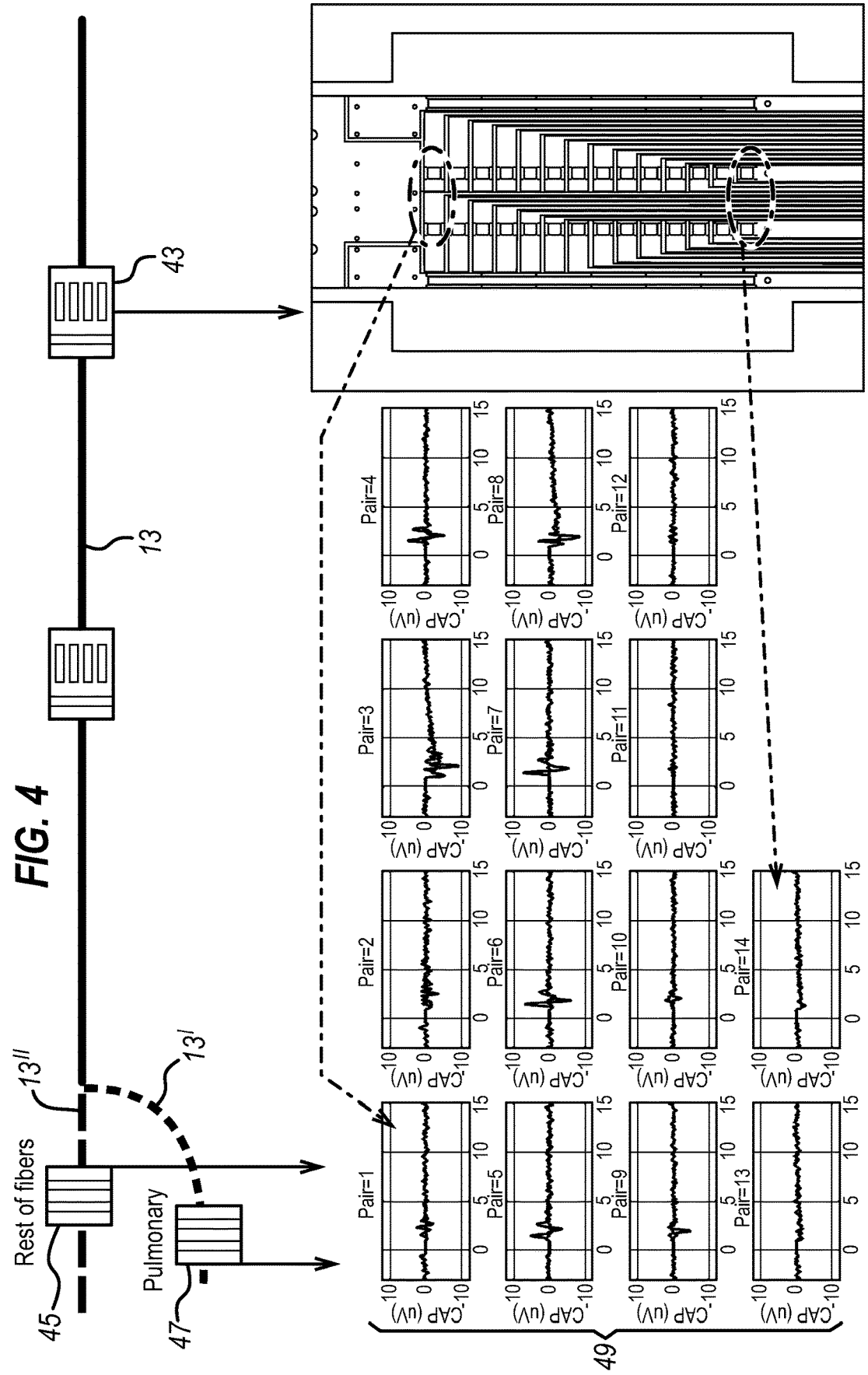
FIG. 4 illustrates further measurements of CAP measured in response to stimulation of a nerve using the nerve stimulation devices.

The arrays described above have been shown to selectively stimulate specific nerve fibers in a nerve. Referring to FIG. 4, arrays comprising two electrode rings each comprising 14 electrodes were used to selectively stimulate nerve fibers. Here, each electrode had a surface of 0.2 mm in width and 0.2 mm in length, and each pair of electrodes were 1 mm apart. One such array 43, was positioned on the vagus nerve 13 of a subject in order to provide selective stimulation to the nerve.

A stimulation device was used to generate electrical signals. In this example, the signals comprise bipolar stimulating pulses with a current of 500 µA, a pulse width of 0.1 ms and a frequency of 5 Hz. These signals were applied to electrode pairs, one longitudinal pair at a time. CAP responses to the stimulation were measured using an array 47 placed on the pulmonary branch 13' of the nerve 13 and another array 45 placed on the rest of descending vagus nerve fibers 13". For example, a CorTec array may be used.

The activation patterns for each of the 14 pairs of electrodes are illustrated in the chart 49. In the charts 49 the lines represent the readings from the pulmonary branch and the readings from the rest of vagus nerve fibers.

In one example, in order to optimize electrode configuration for optimal differential activation of fascicles within a target nerve, which is the vagus nerve in this example, an in-silico model was initially used. A 3D cylindrical model of the human-sized vagus nerve was produced in the COMSOL simulation software. The model was 2.8 mm in diameter, and had 2 compartments: intraneural space with fascicles (effective average conductivity 0.3 S/m), and 100 µm-thick epineurium (0.083 S/m, (Calvetti et al., 2011)) surrounding the latter (FIG. 4A(i)). The discretization was performed according to mesh convergence criteria with the smallest electrode sizes, resulting in the optimal mesh to be 5M regular tetrahedral elements refined in the area of electrode application. The electrodes were placed via applying a complete electrode model on the elements occupying relevant areas of the outer surface of the model in order to simulate effects of the current redistribution due to a contact impedance (Somersalo et al., 1992). Two radially located "virtual fascicles" were placed beneath the electrodes, one ⅓ and another ⅔ of the radius deep (see FIG. 4B), to serve as a target for neuronal stimulation. Threshold current density for fascicle activation is based on historical literature (Warman et al., 1992).

Figure 4A:
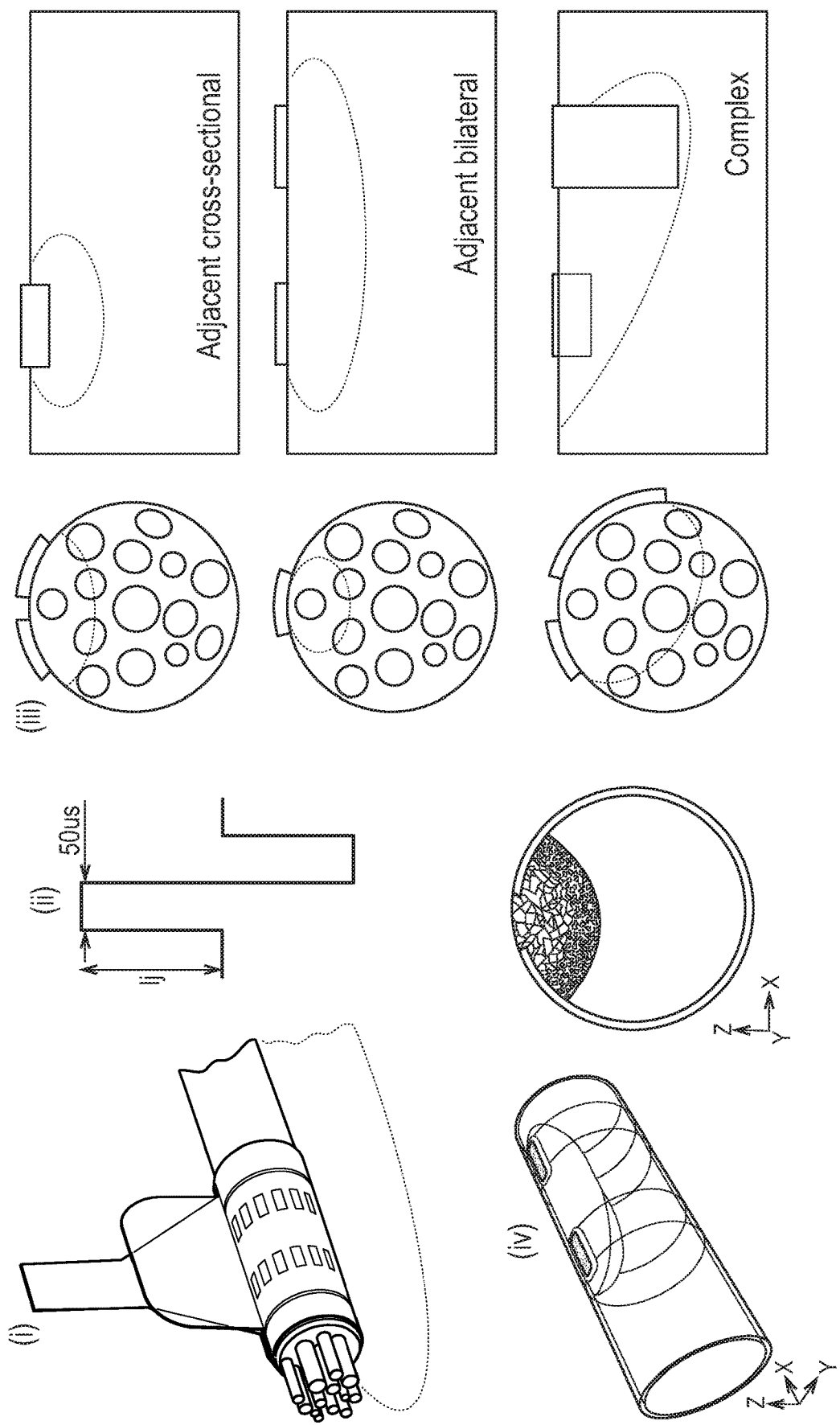
FIG. 4A illustrates examples of modelled stimulations.

FIG. 4A illustrates examples of modelled stimulations. In FIG. 4A(i) there is an image which illustrates the 3D rendering of the human-sized vagus nerve with a cuff electrode around the nerve; FIG. 4A(ii) is an image which illustrates the representative pulse used for simulations as well as for in vivo experiments. The pulse width in this example experiment was 50 µs; FIG. 4A(iii) is a schematic representation of the cross section of the vagus nerve and includes indications of different electrode arrangements used during optimization model. The boxes on the right represent the arrangement of the electrode along the longitudinal axis of the nerve; and FIG. 4A(iv) illustrates two images which show the activation area in the nerve, represented longitudinally and in cross-section, during a simulated stimulation with adjacent bilateral electrodes.

Figure 4B:
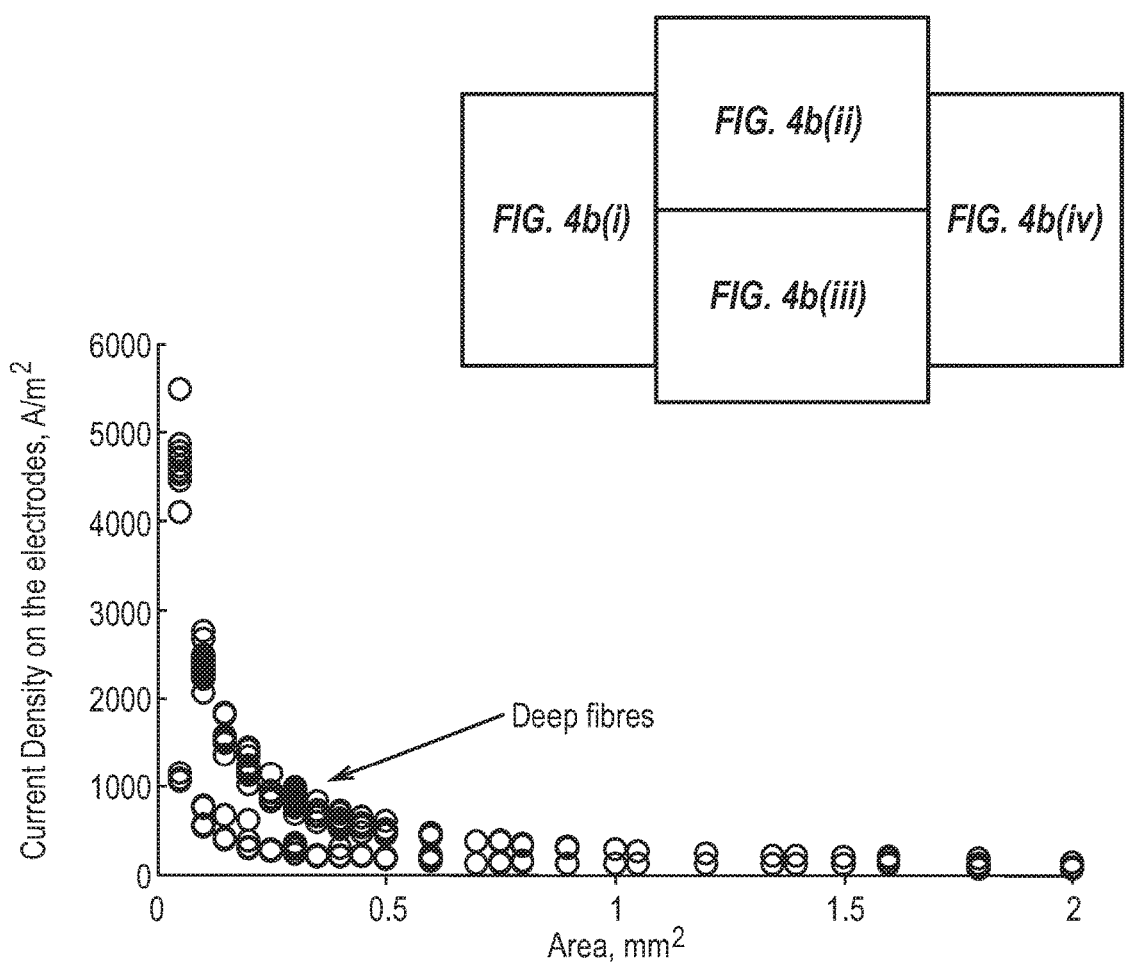
FIG. 4B illustrates radially located "virtual fascicles".
Figure 4B:
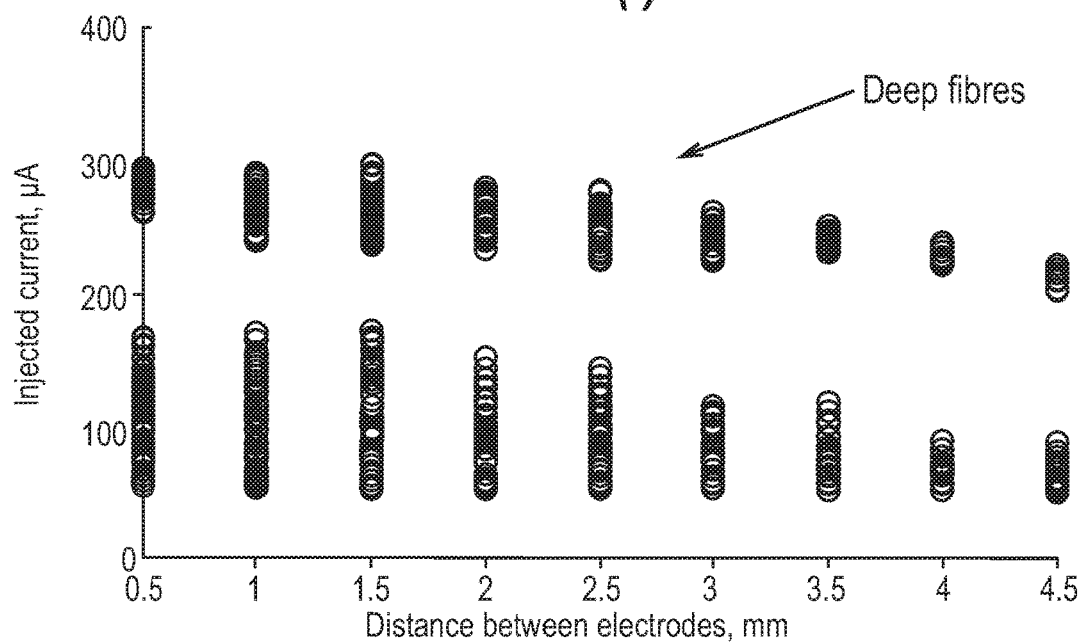

FIG. 4B illustrates modelling results. The graphs summarize the modelling results, and the optimized electrode designed obtained by modelling recruitment of superficial and deep fascicles.

The simulations were performed for each sets of parameters ($p_i$): Electrode Width: 0.05-2.0 mm, Electrode Length 0.5-4.5 mm, and Distance between electrodes: 0.5-4.5 mm, evaluating the minimum current which is required to activate the fascicle, and computing total current distribution given this criterion. Then total activated area in the cross-section (above the activation threshold) $A(J>J_a)$ and maximum current density directly beneath the electrodes ($J_m$) were calculated. Before considering the complex geometrical arrangements, the symmetrical longitudinal bipolar configuration was optimized by varying electrode width, length, and distance between the electrodes.

The model shows that a bipolar configuration produces an absolute minimum on objective function over all possible extended geometrical arrangements, and hence completes the optimization process. The model also shows that the ideal electrode design consisted of an electrode width of 0.35 mm, length of 3.0 mm and interelectrode distance (between 1 electrode in 1 ring and the paired electrode on the second ring) of 3.0 mm and 14 pairs of electrodes (14 for each ring). Selected optimal parameters were then slightly adjusted (width of electrode was 0.2 mm, with 0.2 mm distance between two consecutive electrodes) given the practicality of the manufacturing and in-vivo experimental requirements, and optimal designs were produced.

As illustrated, it can be seen that there was a significant difference in the activation patterns depending on the pairs of electrodes being stimulated at a particular time. Therefore, it will be appreciated that the electrode array 43 is capable of selectively stimulating nerve fibers in a nerve.

Referring again to FIG. 1, another example of selective stimulation will be described. In this example, an in-vivo experiment was conducted in which selective stimulation was combined with electrical impedance tomography (EIT) imaging. Two arrays 1, 3 were implanted on the right cervical vagus nerve 13 of an anesthetized sheep. The first array 1 (Array A) was used to stimulate the nerve 13, whilst the second array 3 (Array B) was used for CAP recording and EIT imaging. The arrays 1, 3 were placed 40 mm apart. In addition, physiological sensors were used to measure physiological parameters, such as end tidal $CO_2$ ($EtCO_2$), electrocardiogram (ECG), blood pressure (BP), heart rate (HR), respiration rate (RR) and peripheral capillary oxygen saturation ($SpO_2$) in the subject. The specific electrode arrays described above with reference to FIG. 2 were used in this example. Although, EIT imaging has been used as an example herein, it is envisaged that other techniques could be used, such as electroneurogram (ENG) recording.

One longitudinal pair at a time was stimulated with 20 Hz frequency, 0.05 ms pulse width, biphasic stimulation pulses in total lasting 60 seconds. This was followed by rest period lasting another 60 seconds. Then, the adjacent pair of electrodes in the array was selected and the protocol repeated for all of the electrodes. The position of each of the electrode pairs is illustrated schematically in FIG. 5, in which the solid circle represents the position of the electrode pair relative to the other pairs.

Figure 6A:
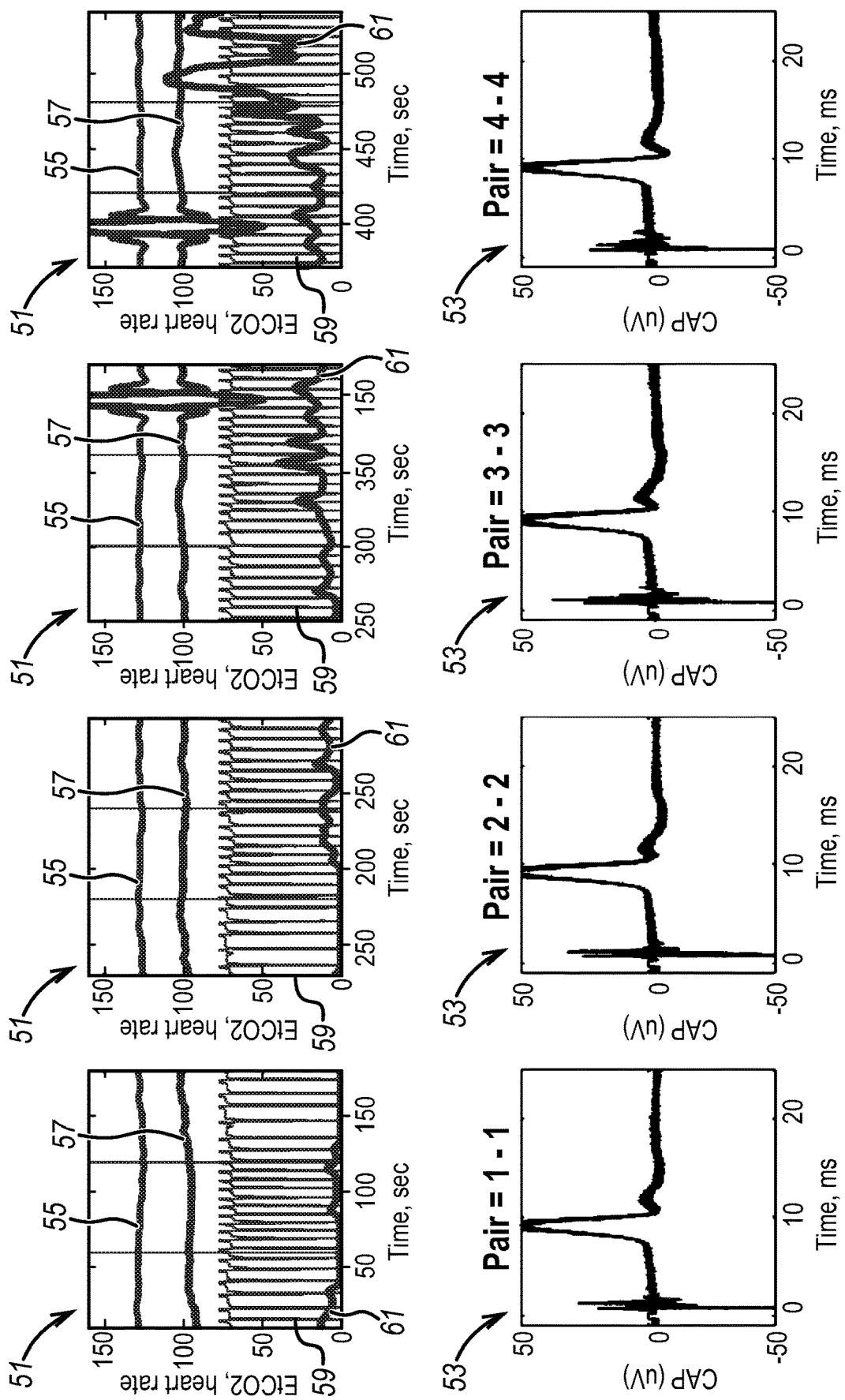
FIGS. 6A and 6B illustrate measurements of physiological activity and CAP measured in response to stimulation of a nerve using the nerve stimulation devices.
Figure 6B:
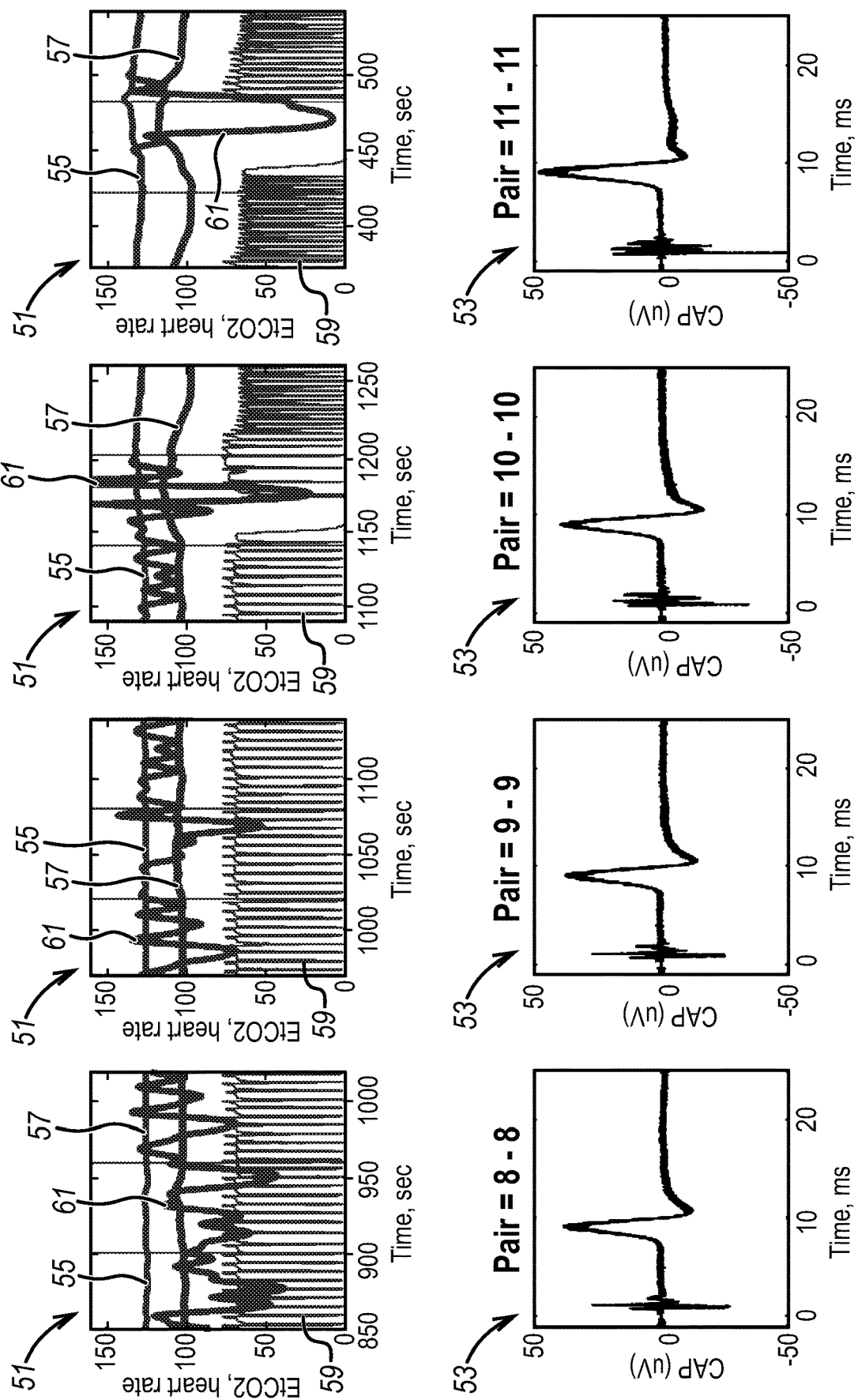

The process of stimulating the electrode pairs lasted 28 minutes during which RR, BP, $EtCO_2$, $SpO_2$ and ECG were constantly monitored. The results of this process are illustrated in FIG. 6A and FIG. 6B in which the upper chart 51 for each pair shows physiological data and the lower chart 53 for each pair shows the average CAP measured during 60 s of stimulation. Referring to FIG. 6A and FIG. 6B, the peak appearing at around 10 ms of delay in the nerve recording represents an EMG contamination from the contraction of the trachea and larynx.

In the upper charts 51 showing physiological data the line 55 shows HR, the line 57 shows BP and the dark line 59 shows $EtCO_2$ indicative of breathing pattern. The line 61 shows HR measured from ECG; however, the HR from ECG readings tended to be inconsistent and, thus, will be ignored for the purposes of this example.

As illustrated in the charts 51, stimulation of specific pairs of electrodes can induce specific physiological responses. For example, stimulation of pairs 3 and 4 resulted in a change in HR and blood pressure. As another example, stimulation of pairs 10-12 resulted in a changed in breathing pattern. In this way, it is possible to determine that specific nerve fibers in proximity to the electrodes of a particular pair are associated with specific organs and physiological responses.

After selective stimulation process, a first pair of electrodes which provided the most prominent pulmonary response was selected. Then, another 3 pairs were selected: the pair opposite the first pair, the pair located 90° clockwise of the first pair and the pair located 90° anti-clockwise of the first pair. This resulted in the selection of 4 pairs, each located at 4 equidistant points around the circumference of the array. Then, by stimulating 1 pair at a time, full EIT recording was performed using the opposite array. In this example, a 14-pair injecting protocol was used with 30 seconds per injection for EIT recording. This required 7 mins per imaging data set. The EIT signal used has a frequency of 6 kHz and 9 kHz, with a current amplitude of 100 uA. Thus, when EIT was combined with stimulation of the most respiratory effective pair of electrodes and the opposing pair, different areas for the vagus nerve were imaged. The results of the EIT imaging process are illustrated in FIG. 7.

Figure 7:
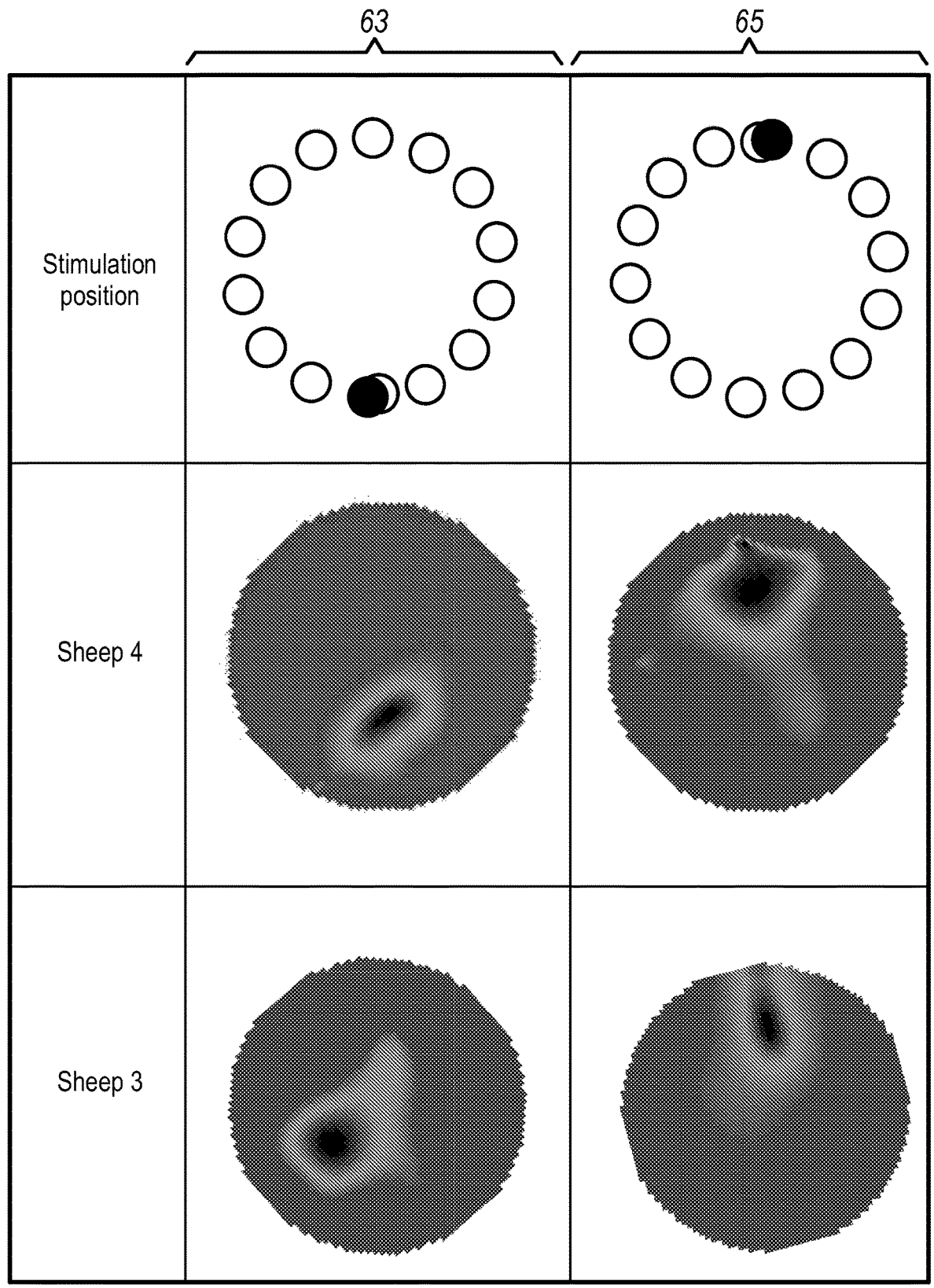
FIG. 7 illustrates images of nerve activity.

Referring to FIG. 7, the images show EIT imaging reconstruction obtained in two different sheep when selective stimulation was performed with array B, and EIT recording was performed with array A. The images in the first column 63 show the EIT images obtained during stimulation of an electrode pair that was found not to cause any respiratory change. The images in the second column 65 show the EIT images obtained during stimulation of an electrode pair that was found to cause respiratory changes. Therefore, it has been shown that the electrode arrays described herein allow specific nerve fibers to be selectively stimulated and imaged.

The in vivo data obtained using the optimized design are summarized in FIG. 7A. Stimulation of the right cervical vagus nerve, in anesthetized sheep (N.8), using a 15 electrode pair cuff electrode, selectively induced cardiovascular responses (defined as bradycardia and hypotension, vs baseline values) and pulmonary responses (defined as an increase in the expiratory time and decrease in respiratory rate, vs baseline values). The relative fascicle positions and the magnitude of the observed physiological effect is shown in FIG. 7A.

FIG. 7A illustrates the estimated location of cardiovascular and pulmonary fascicles in the vagus nerve based on cardiovascular and pulmonary effects cause by stimulation. The average magnitude (N=8)±s.d. of the responses are shown in the graph on the right.

In another example, an implantable system for stimulating and/or monitoring activity in a nerve is provided. This system includes at least one nerve interface device, which may correspond with one or more of the nerve interface device described above. The at least one nerve interface device is arranged, in use, to apply an electrical signal to at least one nerve fiber of a subject. The electrical signal may be applied in a manner consistent with that described above.

The implantable system may comprise a signal generator which is configured to generate a signal to be delivered to the at least one nerve fiber by the first pair of electrodes of the nerve interface device to modulate neural activity within the at least one nerve fiber. The implantable system may also comprise a control sub-system configured to cause the signal generator to deliver the signal to the first pair of electrodes.

The control sub-system may be configured to cause the signal generator to deliver the signal to the first pair of electrodes upon receiving a trigger generated by an operator. In addition, or as an alternative, the control sub-system may be configured to cause the signal generator to deliver the signal to the first pair of electrodes according to a predetermined pattern.

The implantable system may further comprises a detection sub-system configured to detect activity within the at least one nerve fiber at the first pair of electrodes. In this way, the system is able to monitor activity in the nerve, for instance, via imaging the nerve using a technique such as EIT imaging or ENG recording.

The implantable system may be further configured to generate probe electrical signals to be delivered to the at least one nerve fiber by the first pair of electrodes to cause a corresponding electrical response within the at least one nerve fiber. The system may further comprise: a stimulation sub-system configured to cause the signal generator to deliver the probe electrical signals to the first pair of electrodes. The detection sub-system may be configured to detect an electrical response within the at least one nerve fiber at the first pair of electrodes.

The implantable system may further comprise one or more physiological sensors configured to detect physiological activity that is associated with corresponding neural activity within the at least one nerve fiber. An example of a physiological sensor is an ECG monitor, which can be used to monitor heart activity. In one example, the neural activity is autonomic neural activity. In particular, the detection sub-system is configured to detect the corresponding neural activity within the at least one nerve fiber at the first pair of electrodes.

The implantable system discussed herein may comprise at least one nerve interface device. Examples of nerve interface devices are described above. The stimulation sub-system may be configured to generate probe electrical signals to be delivered to the at least one nerve fiber by each of the plurality of pairs of electrodes of the nerve interface device.

The implantable system may comprise processing means configured to determine, based on the electrical responses and/or corresponding neural activity detected by the detection subsystem, electrical properties at one or more locations within the nerve fiber.

The control sub-system may be configured to determine one or more pairs of electrodes for delivering the signal based on the one or more locations within the nerve fiber at which the detection subsystem determined the electrical properties.

There is also provided a method of modulating activity in at least one nerve fiber of a subject which uses the system described herein. In the method, the system causes the signal generator to deliver a signal to the first pair of electrodes. Then, the signal is delivered via the first pair of electrodes to the at least one nerve fiber. In one example, the signal generator may be initiated to deliver the signal upon receipt of a trigger signal generated by an operator. In another example, the signal generator may be initiated to deliver the signal according to a predetermined pattern.

The method may further comprise the step of detecting, via the first pair of electrodes, activity in the nerve. The method may further comprise the step of delivering a probe electrical signal to the nerve via the first pair of electrodes, wherein the activity in the nerve that is detected via the first pair of electrodes is an electrical response caused by the probe electrical signal. The activity in the nerve that is detected via the first pair of electrodes may be neural activity caused by corresponding physiological activity.

In another example, there is an implantable system for stimulating and monitoring activity in a nerve. This system may comprise first and second nerve interface devices, which may be any one the devices described above. The first device may be arranged, in use, to apply an electrical signal to at least one nerve fiber of a subject. In addition, the second device may be arranged, in use, to detect said electrical signal in the at least one nerve fiber.

The system may further comprise a signal generator configured to generate a signal to be delivered to the at least one nerve fiber by the first pair of electrodes in the first nerve interface device to modulate neural activity within the at least one nerve fiber; a control sub-system configured to cause the signal generator to deliver the signal to the first pair of electrodes in the first nerve interface device; and a detection sub-system configured to detect activity within the at least one nerve fiber at the first pair of electrodes in the second nerve interface device.

In another example, there is a method of stimulating and monitoring activity in at least one nerve fiber of a subject. The method may use an implantable system, which may be one of the systems described above. The method may comprise the steps of causing the signal generator to deliver a signal to the first pair of electrodes in the first nerve interface device; and detecting via the first pair of electrodes in the second nerve interface device activity in the nerve, the activity caused by the signal delivered to the at least one nerve fiber by the first pair of electrodes in the first nerve interface device.

An Implantable Device/System for Implementing Embodiments of the Disclosure

Figure 8:
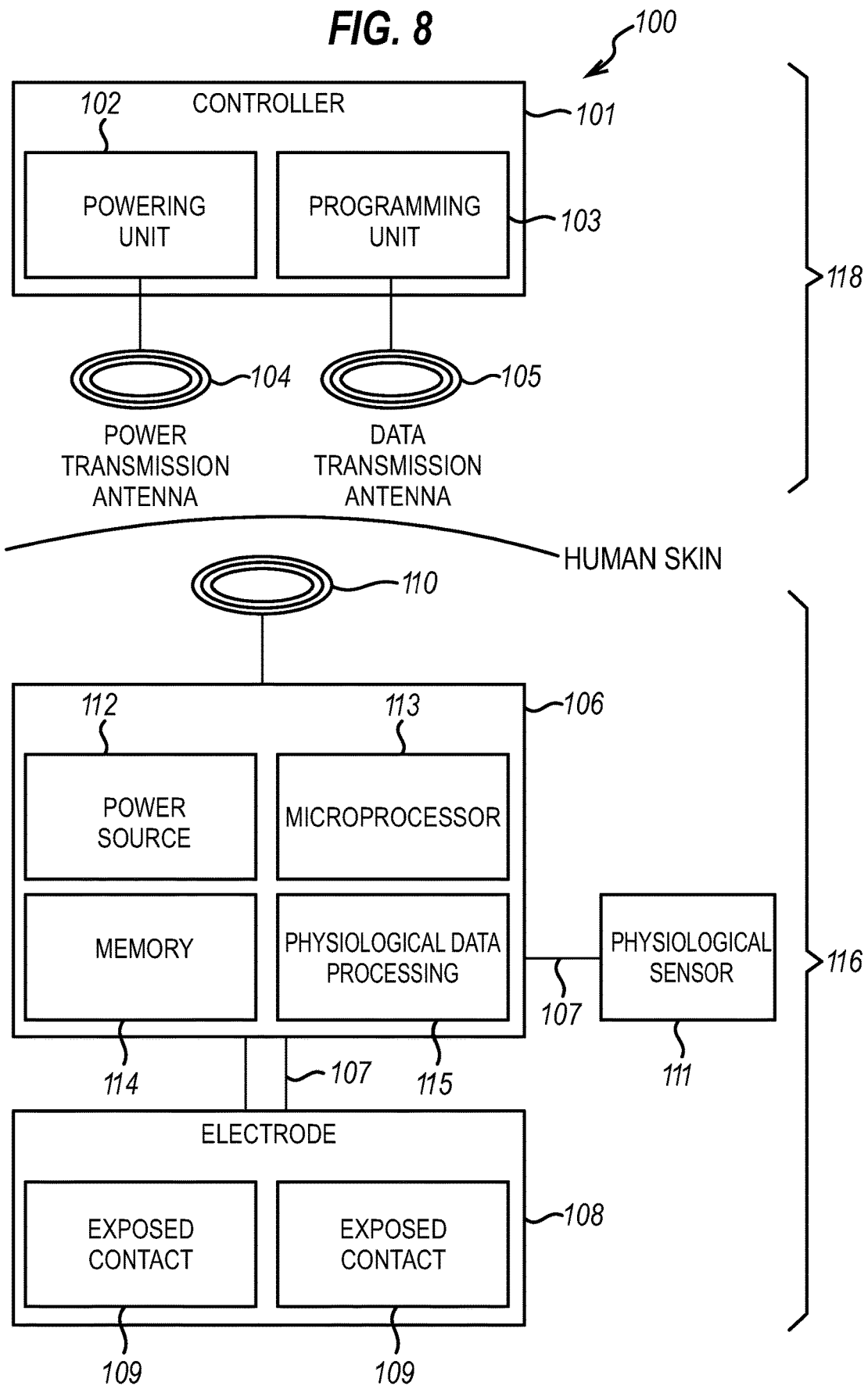
FIG. 8 illustrates an overview of the system.

An implantable system according to the disclosure comprises an implantable device (e.g. implantable device 106 of FIG. 8). The implantable device comprises at least one neural interfacing element such as a transducer, for example an electrode (e.g. electrode 108), suitable for placement on, in, or around a nerve. As will be appreciated, the implantable system also provides a stimulation device such as a current or voltage source, and a power source such as a battery. The implantable system also can comprise a processor (e.g. microprocessor 113) coupled to the at least one neural interfacing element.

The at least one neural interfacing element may take many forms, and includes any component which, when used in an implantable device or system for implementing the disclosure, is capable of applying a stimulus or other signal that modulates electrical activity in a nerve.

The various components of the implantable system can be part of a single physical device, either sharing a common housing or being a physically separated collection of interconnected components connected by electrical leads (e.g. leads 107). As an alternative, however, the disclosure may use a system in which the components are physically separate, and communicate wirelessly. Thus, for instance, the at least one neural interfacing element (e.g. electrode 108) and the implantable device (e.g. implantable device 106) can be part of a unitary device, or together may form an implantable system (e.g. implantable system 116). In both cases, further components may also be present to form a larger device or system (e.g. system 100).

Suitable Forms of a Modulating Signal

The disclosure uses a signal applied via one or more neural interfacing elements (e.g. electrode 108) placed in signaling contact with a nerve.

Signals applied according to the disclosure are ideally non-destructive. As used herein, a "non-destructive signal" is a signal that, when applied, does not irreversibly damage the underlying neural signal conduction ability of the nerve. That is, application of a non-destructive signal maintains the ability of the nerve (e.g. a nerve) or fibers thereof, or other nerve tissue to which the signal is applied, to conduct action potentials when application of the signal ceases, even if that conduction is in practice artificially stimulated as a result of application of the non-destructive signal.

The signal will usually be an electrical signal, which may be, for example, a voltage or current waveform. The at least one neural interfacing element (e.g. electrode 108) of the implantable system (e.g. implantable system 116) is configured to apply the electrical signals to a nerve, or a part thereof. However, electrical signals are just one way of implementing the disclosure, as is further discussed below.

An electrical signal can take various forms, for example, a voltage or current. In certain such embodiments the signal applied comprises a direct current (DC) or an alternating current (AC) waveform, or both a DC and an AC waveform. A combination of DC and AC is particularly useful, with the DC being applied for a short initial period after which only AC is used. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. In other words, a charge-balance alternating current includes a cathodic pulse and an anodic pulse.

In certain embodiments, the AC waveform may be a square, sinusoidal, triangular, trapezoidal, quasitrapezodial or complex waveform. The DC waveform may alternatively be a constant amplitude waveform. In certain embodiments the electrical signal is an AC sinusoidal waveform. In other embodiments, waveform comprise one or more pulse trains, each comprising a plurality of charge-balanced biphasic pulses.

The signal may be applied in bursts. The range of burst durations may be from sub-seconds to minutes, and in rare occasions hours; applied continuously in a duty cycled manner from 0.01% to 100%, with a predetermined time interval between bursts. The electric signal may be applied as step change or as a ramp change in current or intensity. Particular signal parameters for modulating (e.g. stimulating) a nerve are further described below. In one example, the duty cycle of a signal intermittently stimulating a nerve is based on the type of disease or physiology that is being targeted. In addition, indicative feedback may be provided by measuring physiological changes caused due to the stimulation provided and/or clinician input may be provided to update the duty cycle of the signal.

Modulation of the neural activity of the nerve can be achieved using electrical signals which serve to replicate or magnify the normal neural activity of the nerve.

Signal Parameters for Modulating Neural Activity

In all of the above examples, a signal generator may be configured to deliver an electrical signal for modulating (e.g. stimulating) a nerve (e.g. the vagus nerve). In the present application, the signal generator is configured to apply an electrical signal with certain signal parameters to modulate (e.g. stimulate) neural activity in a nerve (e.g. the vagus nerve). Signal parameters for modulating (e.g. stimulating) the nerve, which are described herein, may include waveform shape, charge amplitude, pulse width, frequency, and duration.

It will be appreciated by the skilled person that the current amplitude of an applied electrical signal necessary to achieve the intended modulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

Electrodes

As mentioned above, the implantable system comprises at least one neural interfacing element, the neural interfacing element can be an electrode 108. The neural interface is configured to at least partially and in some embodiments fully circumvent the nerve. The geometry of the neural interface is defined in part by the anatomy of the nerve.

In some embodiments (for example, FIG. 8), electrode 108 may be coupled to implantable device 106 of implantable system 116 via electrical leads 107. Alternatively, implantable device 106 may be directly integrated with the electrode 108 without leads. In any case, implantable device 106 may comprise AC or DC output circuits, optionally based on capacitors and/or inductors, on all output channels (e.g. outputs to the electrode 108, or physiological sensor 111). Electrode 108 may be shaped as one of: a rectangle, an oval, an ellipsoid, a rod, a straight wire, a curved wire, a helically wound wire, a barb, a hook, or a cuff. In addition to electrode 108 which, in use, is located on, in, or near a nerve (e.g. the ICN), there may also be a larger indifferent electrode placed 119 (not shown) in the adjacent tissue.

In some embodiments, electrode 108 may contain at least two electrically conductive exposed contacts 109 configured, in use, to be placed on, in, or near a nerve. Exposed contacts 109 may be positioned, in use, transversely along the axis of a nerve.

Microprocessor

The implantable system 116, in particular the implantable device 106, may comprise a processor, for example microprocessor 113. Microprocessor 113 may be responsible for triggering the beginning and/or end of the signals delivered to the nerve (e.g., a nerve) by the at least one neural interfacing element. Optionally, microprocessor 113 may also be responsible for generating and/or controlling the parameters of the signal.

Microprocessor 113 may be configured to operate in an open-loop fashion, wherein a pre-defined signal (e.g. as described above) is delivered to the nerve at a given periodicity (or continuously) and for a given duration (or indefinitely) with or without an external trigger, and without any control or feedback mechanism. Alternatively, microprocessor 113 may be configured to operate in a closed-loop fashion, wherein a signal is applied based on a control or feedback mechanism. As described elsewhere herein, the external trigger may be an external controller 101 operable by the operator to initiate delivery of a signal. Alternatively, the electrodes of the implanted device may be used to at least indirectly sense physiological attributes that can be affected by the vagus nerve (or another target nerve) without using an external or additional physiological sensor.

For example, EMG signals may be detected at the electrodes of the neural interface which is used to stimulate the nerve. Such EMG signal may consist of the response produced by the laryngeal muscles due to activation of the recurrent laryngeal nerve.

In one example, the electrodes may switch between a stimulation mode and a detection mode. During the stimulation mode, the electrode may be configured to stimulate and during the detection mode the electrodes may be configured to detect a signal. In another example, one or more pairs of electrodes may be used for stimulation whilst the other pairs of electrodes are used to detect the EMG response from the larynges. In yet another example, the stimulating pair of electrodes may be configured to detect. In accordance with these examples, any EMG response from the larynges evoked by the electrodes can be detected by the electrodes as they are being evoked. In other words, stimulation and detection of evoked response can be carried out simultaneously. Thus, it is possible to obtain information about physiological attributes without using an external or additional physiological sensor, or even requiring multiple cuffs of electrodes to be used. The signal derived from the detection at the electrodes may be used as physiological feedback to titrate or adjust stimulation parameters such as signal parameters including ratio of currents (e.g. ratio between a first current source (J1) coupled to each cathode electrode and a second current source (J2) coupled to each anode electrode or amplitude of the currents) applied to the electrodes and/or pulse parameters.

The above described closed-loop system enables dynamic adjustment in response to real-time feedback to select the appropriate pair of electrodes for stimulation and increase the therapeutic window.

Thus, the electrodes in any of the embodiment described herein may be configured to detect a physiological response in a user to the application of an electrical signal to the nerve. Furthermore, different pairs of electrodes may operate in different modes, such that stimulation and detection are performed simultaneously.

It will further be appreciated that the physiological sensor, the electrodes and the user input may be used separately or in any combination with each other.

Microprocessor 113 of the implantable system 116, in particular of the implantable device 106, may be constructed so as to generate, in use, a preconfigured and/or operator-selectable signal that is independent of any input. In some embodiments, however, microprocessor 113 is responsive to an external signal, such as information (e.g. data) pertaining to one or more physiological parameters of the subject.

Microprocessor 113 may be triggered upon receipt of a signal generated by an operator, such as a physician or the subject in which the device 116 is implanted. To that end, the implantable system 116 may be part of a system which additionally comprises an external system 118 comprising a controller 101. An example of such a system is described below with reference to FIG. 8.

External system 118 of system 100 is external the implantable system 116 and external to the subject, and comprises controller 101. Controller 101 may be used for controlling and/or externally powering implantable system 116. To this end, controller 101 may comprise a powering unit 102 and/or a programming unit 103. The external system 118 may further comprise a power transmission antenna 104 and a data transmission antenna 105, as further described below.

The controller 101 and/or microprocessor 113 may be configured to apply any one or more of the above signals to the nerve intermittently or continuously. Intermittent application of a signal involves applying the signal in an (on-off)$_n$ pattern, where n >1. For example, the stimulation may be applied for at least 1 minute, then turned off for several minutes, and then applied again, so as to ensure correct electrode placement during surgery, and validation of successful stimulation. Such intermittent application may be used for on table surgical application, for example. A continuous application may be applied as a therapeutic application, for example after the surgical placement has been achieved. In an example continuous application, the signal may be applied continuously for at least 5 days, optionally at least 7 days, before ceasing for a period (e.g. 1 day, 2 days, 3 days, 1 week, 2 weeks, 1 month), before being again applied continuously for at least 5 days, etc. Thus the signal is applied for a first time period, then stopped for a second time period, then reapplied for a third time period, then stopped for a fourth time period, etc. In such an embodiment, the first, second, third and fourth periods run sequentially and consecutively. The duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d.

In certain embodiments, the signal is applied by controller 101 and/or microprocessor for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

Continuous application may continue indefinitely, e.g. permanently. Alternatively, the continuous application may be for a minimum period, for example the signal may be continuously applied for at least 5 days, or at least 7 days.

Whether the signal applied to the nerve is controlled by controller 101, or whether the signal is continuously applied directly by microprocessor 113, although the signal might be a series of pulses, the gaps between those pulses do not mean the signal is not continuously applied.

In certain embodiments, the signal is applied only when the subject is in a specific state e.g. only when the subject is awake, only when the subject is asleep, prior to and/or after the ingestion of food, prior to and/or after the subject undertakes exercise, during surgical placement under anesthesia, etc.

The various embodiments for timing for modulation of neural activity in the nerve can all be achieved using controller 101 in a device/system of the disclosure.

Other Components of the System Including the Implantable Device

In addition to the aforementioned electrode 108 and microprocessor 113, the implantable system 116 may comprise one or more of the following components: implantable transceiver 110; physiological sensor 111; power source 112; memory 114; and physiological data processing module 115. Additionally or alternatively, the physiological sensor 111; memory 114; and physiological data processing module 115 may be part of a sub-system external to the implantable system. Optionally, the external sub-system may be capable of communicating with the implantable system, for example wirelessly via the implantable transceiver 110.

In some embodiments, one or more of the following components can be contained in the implantable device 106: power source 112; memory 114; and a physiological data processing module 115.

The power source 112 may comprise a current source and/or a voltage source for providing the power for the signal delivered to a nerve by the electrode 108. The power source 112 may also provide power for the other components of the implantable device 106 and/or implantable system 116, such as the microprocessor 113, memory 114, and implantable transceiver 110. The power source 112 may comprise a battery, the battery may be rechargeable.

It will be appreciated that the availability of power is limited in implantable devices, and the disclosure has been devised with this constraint in mind. The implantable device 106 and/or implantable system 116 may be powered by inductive powering or a rechargeable power source.

System Including Implantable Device

With reference to FIG. 8, the implantable device 106 of the disclosure may be part of a system 110 that includes a number of subsystems, for example the implantable system 116 and the external system 118. The external system 118 may be used for powering and programming the implantable system 116 and/or the implantable device 106 through human skin and underlying tissues.

The external subsystem 118 may comprise, in addition to controller 101, one or more of: a powering unit 102, for wirelessly recharging the battery of power source 112 used to power the implantable device 106; and, a programming unit 103 configured to communicate with the implantable transceiver 110. The programming unit 103 and the implantable transceiver 110 may form a communication subsystem. In some embodiments, powering unit 102 is housed together with programming unit 103. In other embodiments, they can be housed in separate devices.

The external subsystem 118 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in implantable system 116 for data reception and transmission from/to the external system 118. If more than one antenna is used in the implantable system 116, these antennae are rotated 30 degrees from one another to achieve a better degree of power transfer efficiency during slight misalignment with the with power transmission antenna 104.

External system 118 may comprise one or more external body-worn physiological sensors 121 (not shown) to detect signals indicative of one or more physiological parameters. The signals may be transmitted to the implantable system 116 via the at least one antennae of implantable transceiver 110. Alternatively or additionally, the signals may be transmitted to the external system 116 and then to the implantable system 116 via the at least one antennae of implantable transceiver 110. As with signals indicative of one or more physiological parameters detected by the implanted physiological sensor 111, the signals indicative of one or more physiological parameters detected by the external sensor 121 may be processed by the physiological data processing module 115 to determine the one or more physiological parameters and/or stored in memory 114 to operate the implantable system 116 in a closed-loop fashion. The physiological parameters of the subject determined via signals received from the external sensor 121 may be used in addition to alternatively to the physiological parameters determined via signals received from the implanted physiological sensor 111.

For example, in a particular embodiment a detector external to the implantable device may include an optical detector including a camera capable of imaging the eye and determining changes in physiological parameters, in particular the physiological parameters described above. As explained above, in response to the determination of one or more of these physiological parameters, the detector may trigger delivery of signal to a nerve by the electrode 108, or may modify the parameters of the signal being delivered or a signal to be delivered to a nerve by the electrode 108 in the future.

The system 100 may include a safety protection feature that discontinues the electrical stimulation of a nerve in the following exemplary events: abnormal operation of the implantable system 116 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by an operator (e.g. a physician or the subject). The safety precaution feature may be implemented via controller 101 and communicated to the implantable system 116, or internally within the implantable system 116.

The external system 118 may comprise an actuator 120 (not shown) which, upon being pressed by an operator (e.g. a physician or the subject), will deliver a signal, via controller 101 and the respective communication subsystem, to trigger the microprocessor 113 of the implantable system 116 to deliver a signal to the nerve by the electrode 108.

System 100 of the disclosure, including the external system 118, but in particular implantable system 116, can be made from, or coated with, a biostable and biocompatible material. This means that the device/system is both protected from damage due to exposure to the body's tissues and also minimizes the risk that the device/system elicits an unfavorable reaction by the host (which could ultimately lead to rejection). The material used to make or coat the device/system should ideally resist the formation of biofilms. Suitable materials include, but are not limited to, poly(p-xylene) polymers (known as Parylenes) and polytetrafluoroethylene.

The implantable device 116 of the disclosure will generally weigh less than 50 g. In other examples, the implantable device 116 may weigh more, for example around 100-200 g.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the disclosure.

The term "about" in relation to a numerical value x is optional and means, for example, x+10%.

Unless otherwise indicated each embodiment as described herein may be combined with another embodiment as described herein.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

It will be appreciated that the modules described herein may be implemented in hardware or in software. Furthermore, the modules may be implemented at various locations throughout the system.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person. For example, a range "between" "x" and "y" may include values "x" and "y".

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and a method or apparatus may contain additional blocks or elements.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought. Any of the module described above may be implemented in hardware or software.

It will be understood that the above description of some embodiments is given by way of example only and various modifications may be made by those skilled in the art. Although various embodiments have been described above with a certain degree of particularity, or with reference to one or more individual embodiments, those skilled in the art could make numerous alterations to the disclosed embodiments without departing from the scope of this disclosure.

Figure 9:
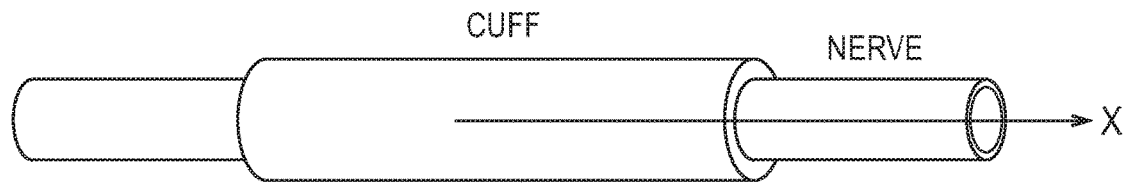
FIG. 9 illustrates a cuff arranged about a nerve.
Figure 10:
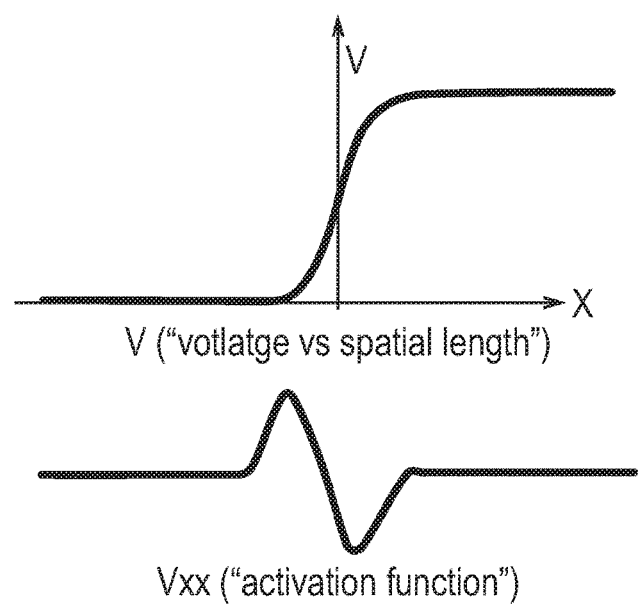
FIG. 10 illustrates an example of voltage varying with respect to the position along the length of a nerve in a scenario in which action potentials are non-directional.
Figure 11:
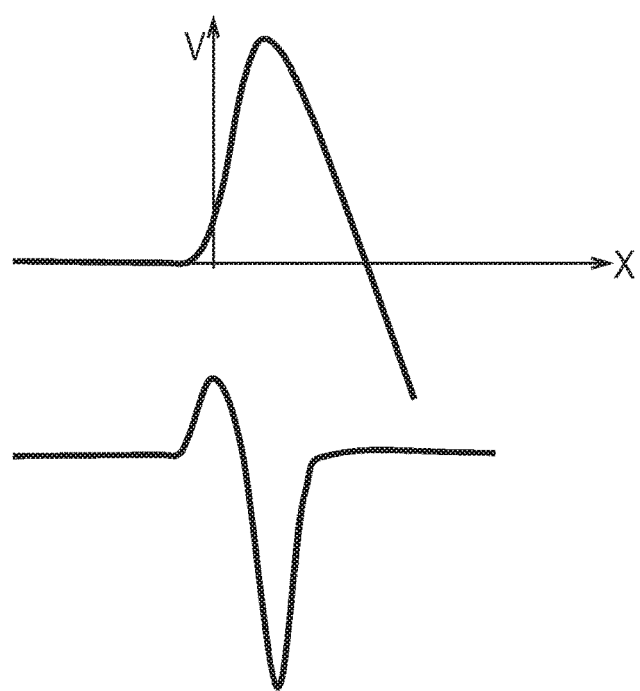
FIG. 11 illustrates an example of voltage varying with respect to the position along the length of a nerve in a scenario in which action potentials are directional.

Ideal "Non-Directional" Example Versus Ideal "Directional" Example (FIGS. 9 to 11)

FIGS. 9 and 10 illustrate the ideal voltage (V) with respect to the distance along the length of the nerve (X) when action potentials are induced non-directionally in the nerve. The "voltage vs spatial length" chart in FIG. 10 illustrates the ideal relationship between V and X where a nerve is stimulated non-directionally (i.e. when the action potentials travel in both directions along the length of the nerve when the nerve is stimulated by the cuff). The "activation function" chart in FIG. 10 illustrates the second derivative of the relationship between V and X shown in the "voltage vs spatial length" chart in FIG. 10. In other words, the "activation function" chart in FIG. 10 illustrates the rate of change of the rate of change of voltage (V) with respect to the distance along the length of the nerve (X). Thus, FIG. 10 shows the ideal "activation function" in the scenario in which action potentials travel in both directions along the length of the nerve.

On the other hand, FIGS. 9 and 11 illustrate the ideal voltage (V) with respect to the distance along the length of the nerve (X) when action potentials are induced directionally in the nerve. The "voltage vs spatial length" chart in FIG. 11 illustrates the ideal relationship between V and X where a nerve in stimulated directionally (i.e. when the action potentials travel in a single direction along the length of the nerve when the nerve is stimulated by the cuff). The "activation function" chart in FIG. 11 illustrates the second derivative of the relationship between V and X shown in the "voltage vs spatial length" chart in FIG. 11. In other words, the "activation function" chart in FIG. 11 illustrates the rate of change of the rate of change of voltage (V) with respect to the distance along the length of the nerve (X). Thus, FIG. 11 shows the ideal "activation function" in the scenario in which action potentials travel in one direction along the length of the nerve.

Virtual Cathode

The directionality described above can be achieved using various embodiments described above in relation to FIGS. 1a-1c. However, under certain conditions such as application of higher currents in order to stimulate nerve with higher stimulation threshold, virtual cathodes can form at either side of the anode along the length of the electrode. These virtual cathodes, particularly the one distal from the cathode can reduce the effectiveness of the arrest electrode (i.e. blocking). This is because the virtual cathode may in some cases sufficiently depolarize and launch an action potential. Thus, even if an action potential is blocked at the anode, it may be re-launched at a virtual cathode formed adjacent to the anode (and distal from the cathode).

Therefore, another aspect of the disclosure is to reduce such virtual cathode which may be created around the anode when trying to block action potential.

According to this aspect of the disclosure, a reduction of virtual cathode is achieved by providing impedance matching between the anode and the surrounding tissue.

By providing impedance matching between the anode and the surrounding tissue (which surrounds the anode itself or the cuff on which the anode is positioned), it is possible to reduce virtual cathode and thereby apply higher currents to stimulate higher threshold nerves with directional selectivity in a reliable manner.

In one embodiment, such impedance matching is achieved by gradually increasing the resistance along the length of the electrode in the direction away from the cathode. In this embodiment, the anode may be considered as having a first portion which is closer to the cathode and a second portion further away from the cathode. The first portion may increase charge density as described above to achieve directionality, and the second portion may function to decrease any virtual cathode that may be formed around the anode. Some examples on how gradual increase in resistance along the length of the electrode (anode in this case) is described in more detail below.

Figure 12:
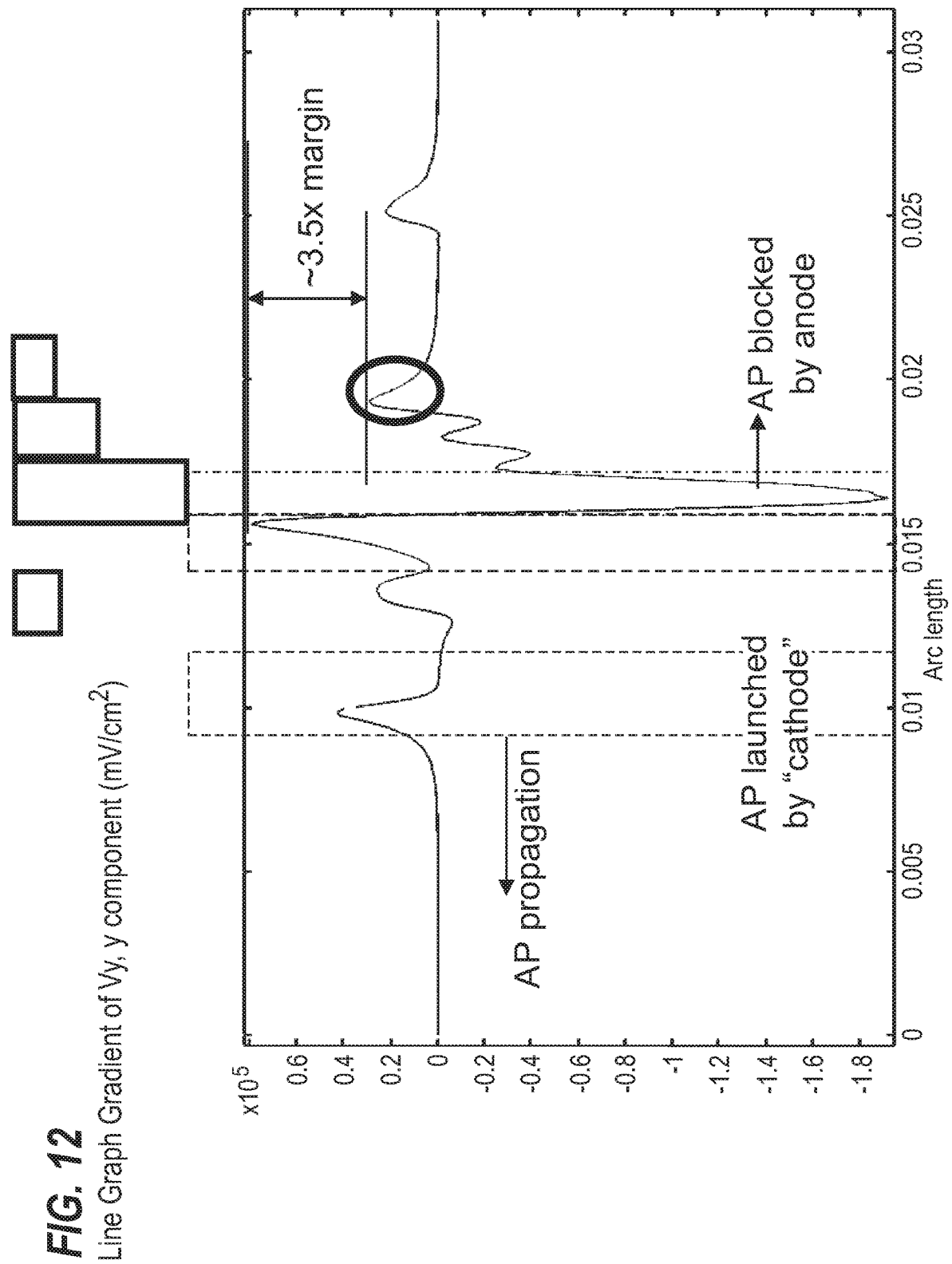
FIG. 12 illustrates experimental results for an electrode configuration similar to that illustrated in FIG. 1a with each of the anode electrodes having a stepped configuration.

Stepped Anode Example (FIG. 12)

FIG. 12 illustrates an example of an electrode configuration similar to that described with reference to FIGS. 1, 1a and 1b where there are two rings of electrodes, and each electrode in a first ring has a corresponding electrode in a second ring thus forming a plurality of pairs of electrodes. In this example, each electrode in the first ring is an anode electrode and each electrode in the second ring is a cathode electrode. Each cathode electrode has a square or rectangular shape. In this specific example, each anode electrode comprises a plurality of electrode portions each having a different surface area. As illustrated, the plurality of electrode portions comprises a first electrode portion, a second electrode portion and a third electrode portion. The surface area illustrated in FIG. 12 do not represent the actual surface area of the electrodes. For example, the first electrode may have a smaller surface area than the corresponding cathode, The first electrode portion is closer to the corresponding cathode than the second and third electrode portions. The second electrode portion is closer to the corresponding cathode than the third electrode portion. The first electrode portion has a larger surface area than the second portion, and the second electrode portion has a larger surface area than the third electrode portion. Each one of the plurality of electrode portions are electrically connected to one another so as to form a unitary electrode. In this case, the first electrode portion may be the first portion which achieves directionality, and the second and third electrode portions may be the second portion which reduces formation of virtual cathodes.

In this example, the device stimulates the nerve directionally in that action potentials are induced in the nerve that propagate along the length of the nerve in the proximal direction. However, in this example a virtual cathode is not formed which minimizes the risk of action potentials propagating in a distal direction away from the cathode beyond the anode.

Figure 13:
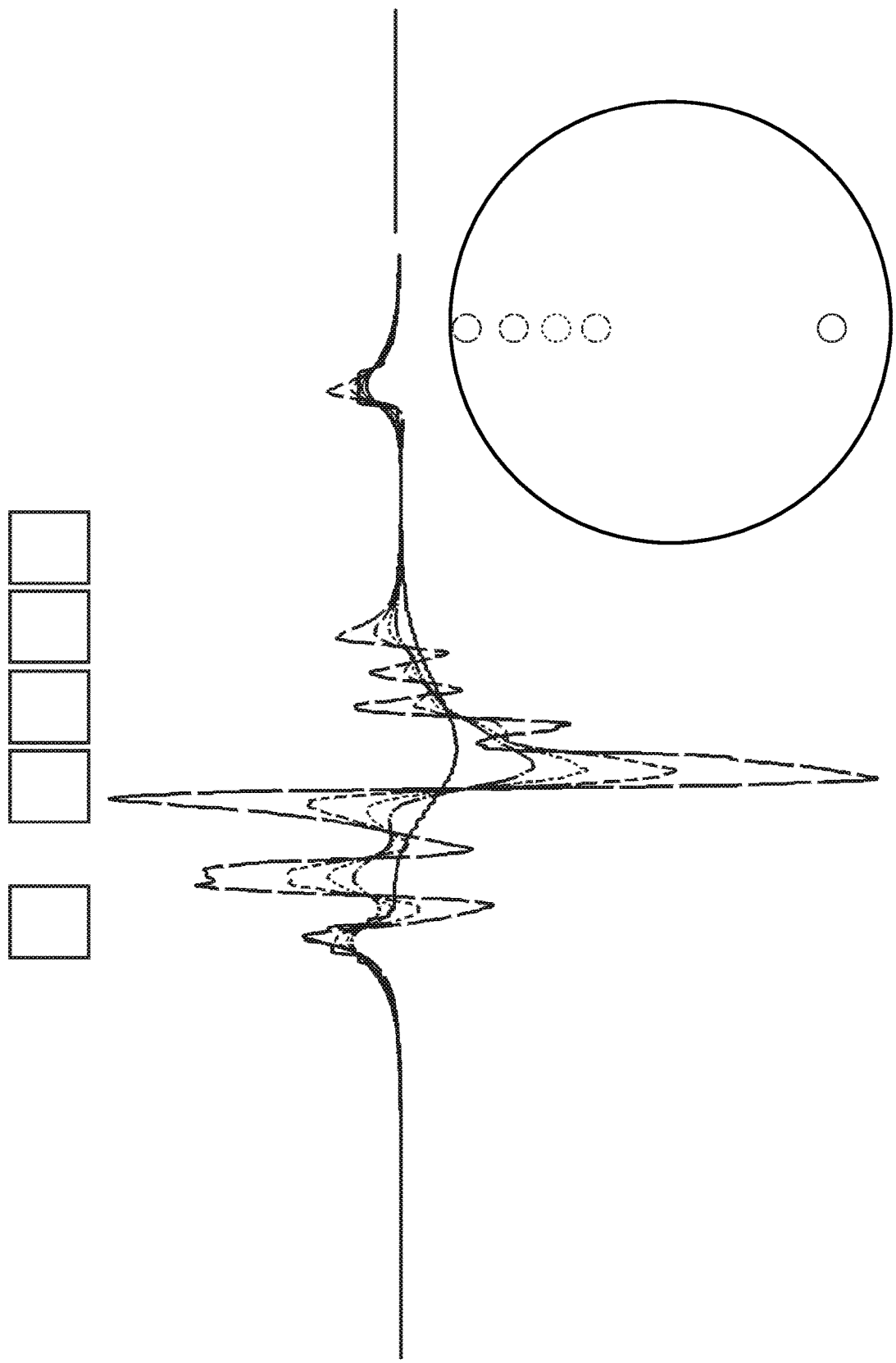
FIG. 13 illustrates experimental results for an electrode configuration similar to that illustrated in FIG. 1a with each of the anode electrodes comprising an electrode array.

Multiple Anodes Supplying Different Current Example (FIG. 13)

FIG. 13 illustrates an example of an electrode configuration similar to that described with reference to FIGS. 1, 1a and 1b where there are two rings of electrodes, and each electrode in a first ring has a corresponding electrode in a second ring thus forming a plurality of pairs of electrodes. In this example, each electrode in the first ring is an anode electrode and each electrode in the second ring is a cathode electrode. Each cathode electrode has a square or rectangular shape. In this specific example, each anode electrode comprises a plurality of electrode portions that separated are from one another, so that there is a gap between each adjacent electrode portion. In this way, it is possible to stimulate each one of the electrode portions with a different current, for instance by using a different current source for each electrode portion. Each one of the plurality of electrode portions may be stimulated with a different current, so that the impedance of the first electrode portion is lower than the impedance of the second electrode portion and so that the impedance of the second electrode portion is lower than the impedance of the third electrode portion.

By using this electrode configuration, the device stimulates the nerve directionally in that action potentials are induced in the nerve that propagate along the length of the nerve in the proximal direction, and action potentials are minimized in the distal direction which is shown in the charts in FIG. 13. These charts also show that the magnitude of response is greater for nerve fibers that are closer to the outer surface of the nerve in comparison to nerve fibers that are further from the outer surface.

Figure 14:
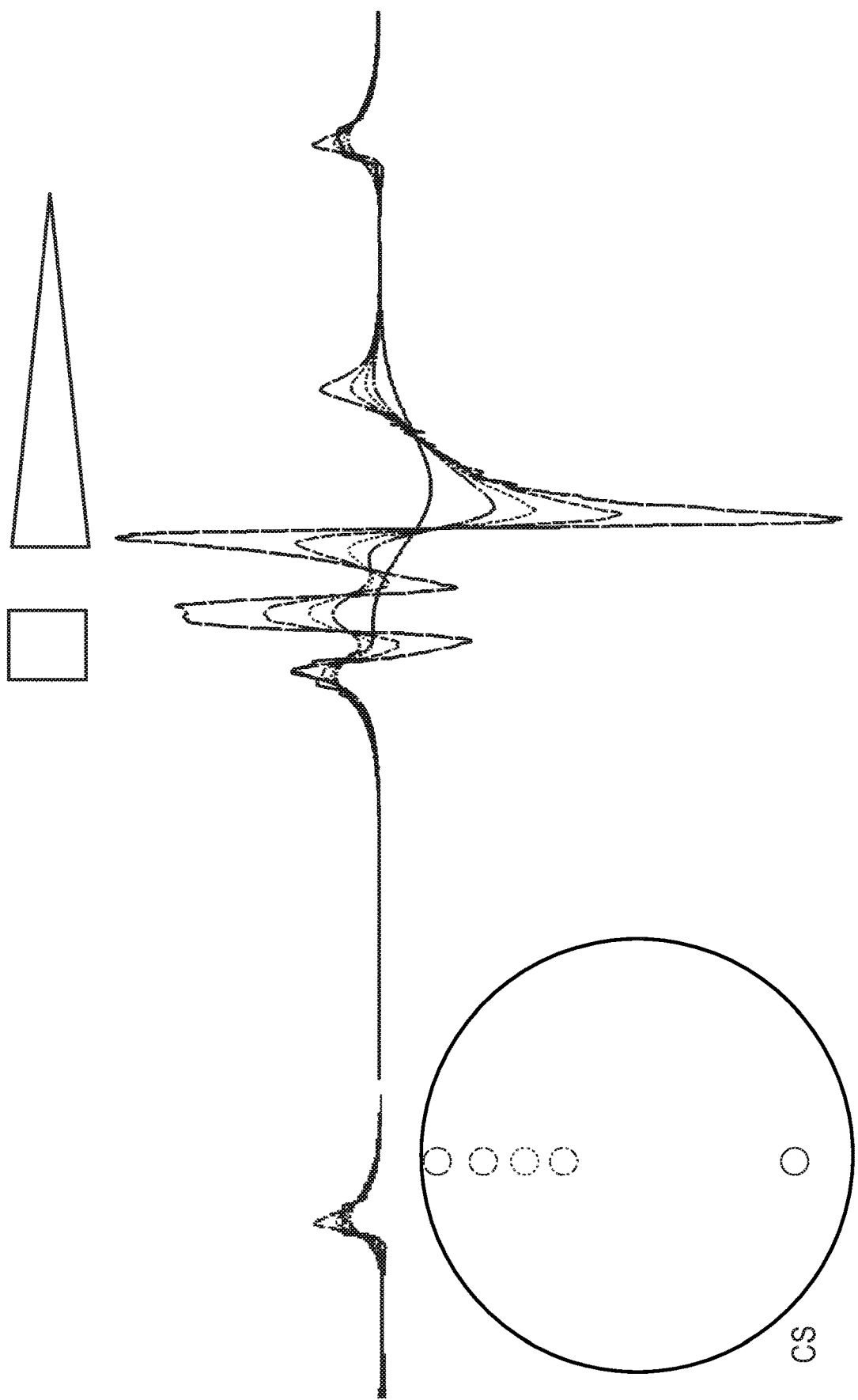
FIG. 14 illustrates experimental results for an electrode configuration similar to that illustrated in FIG. 1a with each of the anode electrodes of the second ring being triangular in shape.
Figure 17:
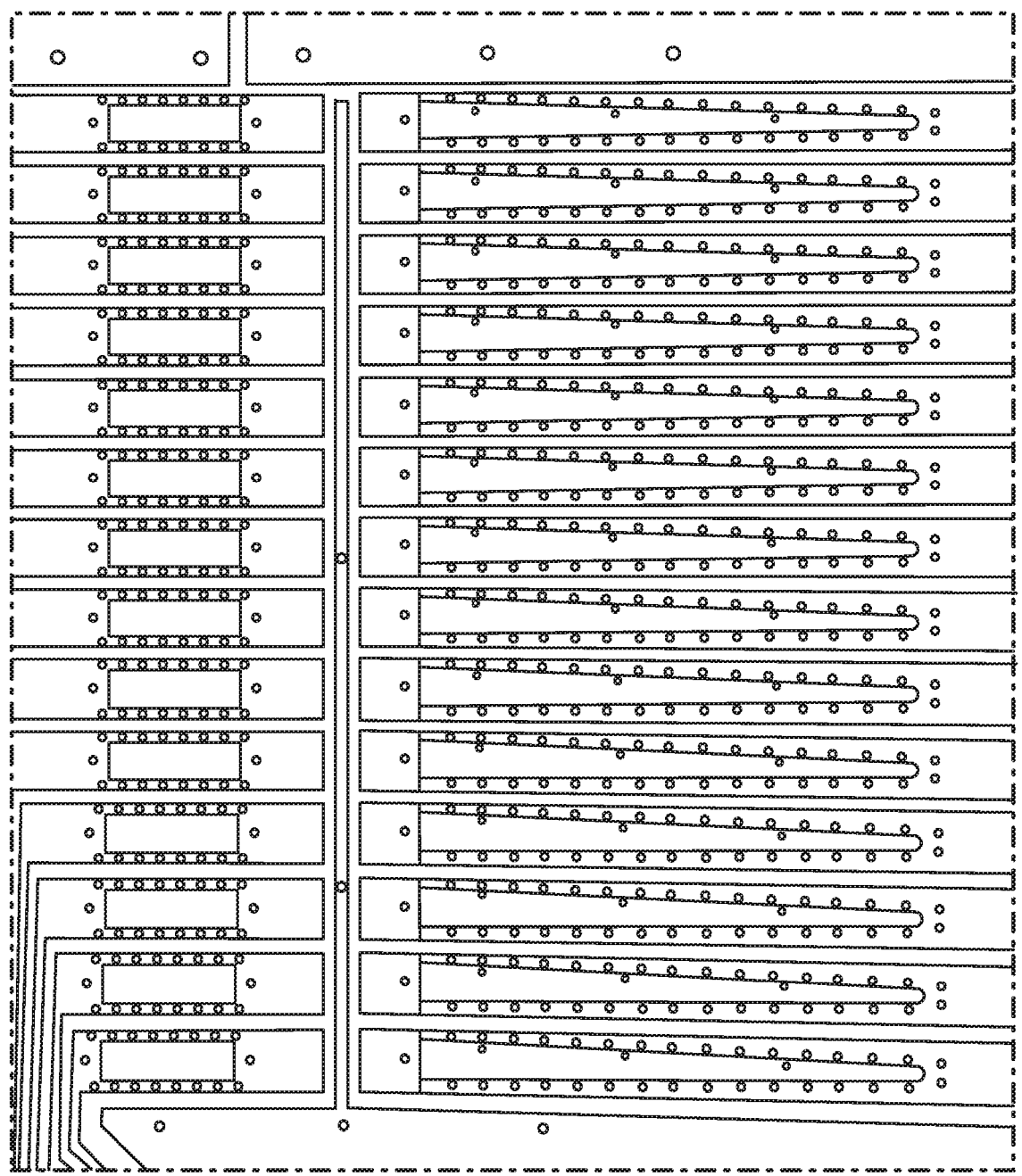
FIG. 17 illustrates an example of the electrode configuration of FIG. 14.

Triangular Anode Example (FIGS. 14 and 17)

FIGS. 14 and 17 illustrate an example of an electrode configuration similar to that described with reference to FIGS. 1, 1a and 1b where there are two rings of electrodes, and each electrode in a first ring has a corresponding electrode in a second ring thus forming a plurality of pairs of electrodes. In this example, each electrode in the first ring is an anode electrode and each electrode in the second ring is a cathode electrode. Each cathode electrode has a square or rectangular shape and each anode electrode has a triangular shape. In this specific example, each anode has the shape of an isosceles triangle. The length of the isosceles triangle shape extends in a direction parallel with the longitudinal axis of the nerve. The width of the isosceles triangle shape extends in a direction perpendicular to the longitudinal axis of the nerve.

By using this electrode configuration, the device stimulates the nerve directionally in that action potentials are induced in the nerve that propagate along the length of the nerve in the proximal direction, and action potentials are minimized in the distal direction which is shown in the charts in FIG. 14. These charts also show that the magnitude of response is greater for nerve fibers that are closer to the outer surface of the nerve in comparison to nerve fibers that are further from the outer surface.

Two Current Sources Example (FIGS. 15, 16 and 18)

FIGS. 15 and 16 illustrate an example of an electrode configuration and stimulation system similar to that described with reference to FIGS. 1, 1a and 1b where there are two rings of electrodes, and each electrode in a first ring has a corresponding electrode in a second ring thus forming a plurality of pairs of electrodes. In this example, each electrode in the first ring is an anode electrode and each electrode in the second ring is a cathode electrode. In addition, each cathode electrode is coupled to a first current source (J1), and each anode electrode is coupled to a second current source (J2).

The first current source (J1) delivers a different current to the second current source (J2). This system is configured to deliver a quasitrapezoidal pulse, as illustrated in the lower chart in FIG. 16. The quasitrapezoidal pulse is made up of two components: a square wave pulse (TON) and a decay period (TDECAY). This results in a charged balanced asymmetric pulse.

By using this system with two current sources delivering different currents to the anodes in comparison to the cathodes, the device stimulates the nerve directionally in that action potentials are induced in the nerve that propagate along the length of the nerve in the proximal direction, and action potentials are minimized in the distal direction which is shown in the charts in FIG. 14. These charts also show that the magnitude of response is greater for nerve fibers that are closer to the outer surface of the nerve in comparison to nerve fibers that are further from the outer surface.

FIG. 18 illustrates an example and corresponding results of the triangular anode configuration described with reference to FIGS. 14 and 17 in combination with the two current sources described with reference to FIGS. 15 and 16.

Figure 19:
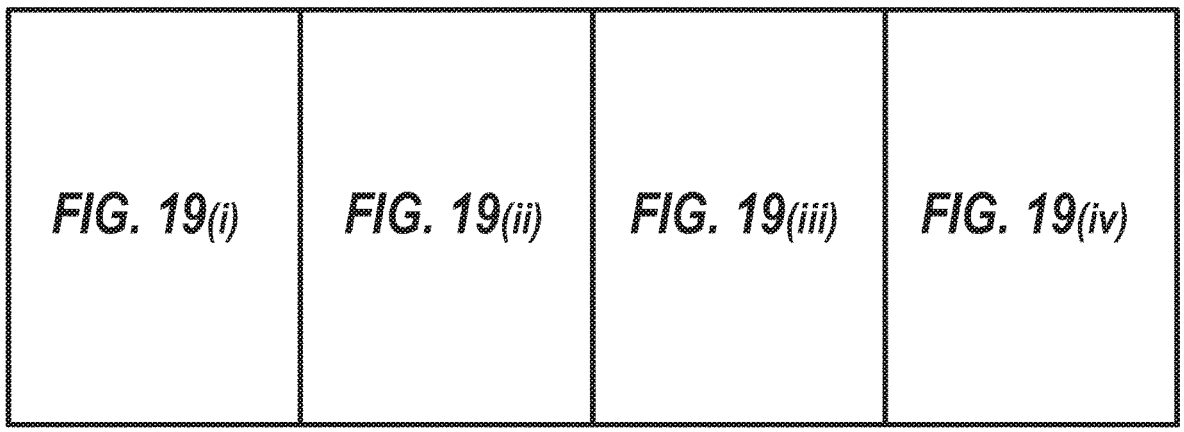
FIG. 19 illustrates the resulting measured expiratory time, recurrent laryngeal (RL) EMG, RL eCAP and esophageal eCAP as the porcine cervical vagus is acutely stimulated using a 14 pair (28 electrode) Directional and Spatially Selective (DASS-CV) neural interface. In this example, the encircled plots shows the electro pair that most closely achieves the intended effect of increasing expiratory time using the "spatial/directional" feature of the DASS-CV interface with stimulation current I1.
Figure 20:
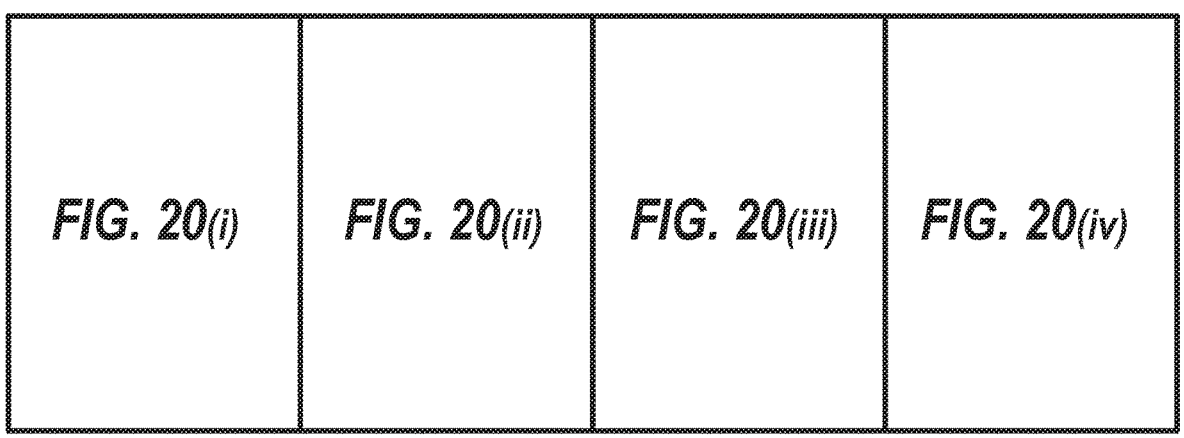
FIG. 20 illustrates a similar experiment as in FIG. 19 wherein the current sources I1 and I2 for the most optimal DASS-CV pair of electrode is varied to minimize the activation of the larynges and esophagus as illustrated by the corresponding EMG and eCAP measurements. In this example, a current ratio of I1=600 uA and I2=400 uA achieves the most optimal results.
Figure 21:
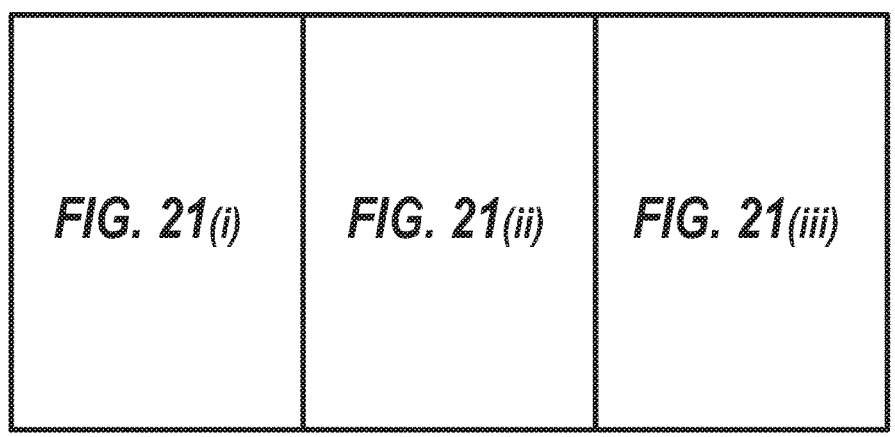
FIG. 21 illustrates a similar experiment as in FIG. 20 wherein a charge balanced asymmetrical (CBA) pulse is applied to current sources I1 and I2 across the most optimal DASS-CV pair of electrode.
Figure 19:
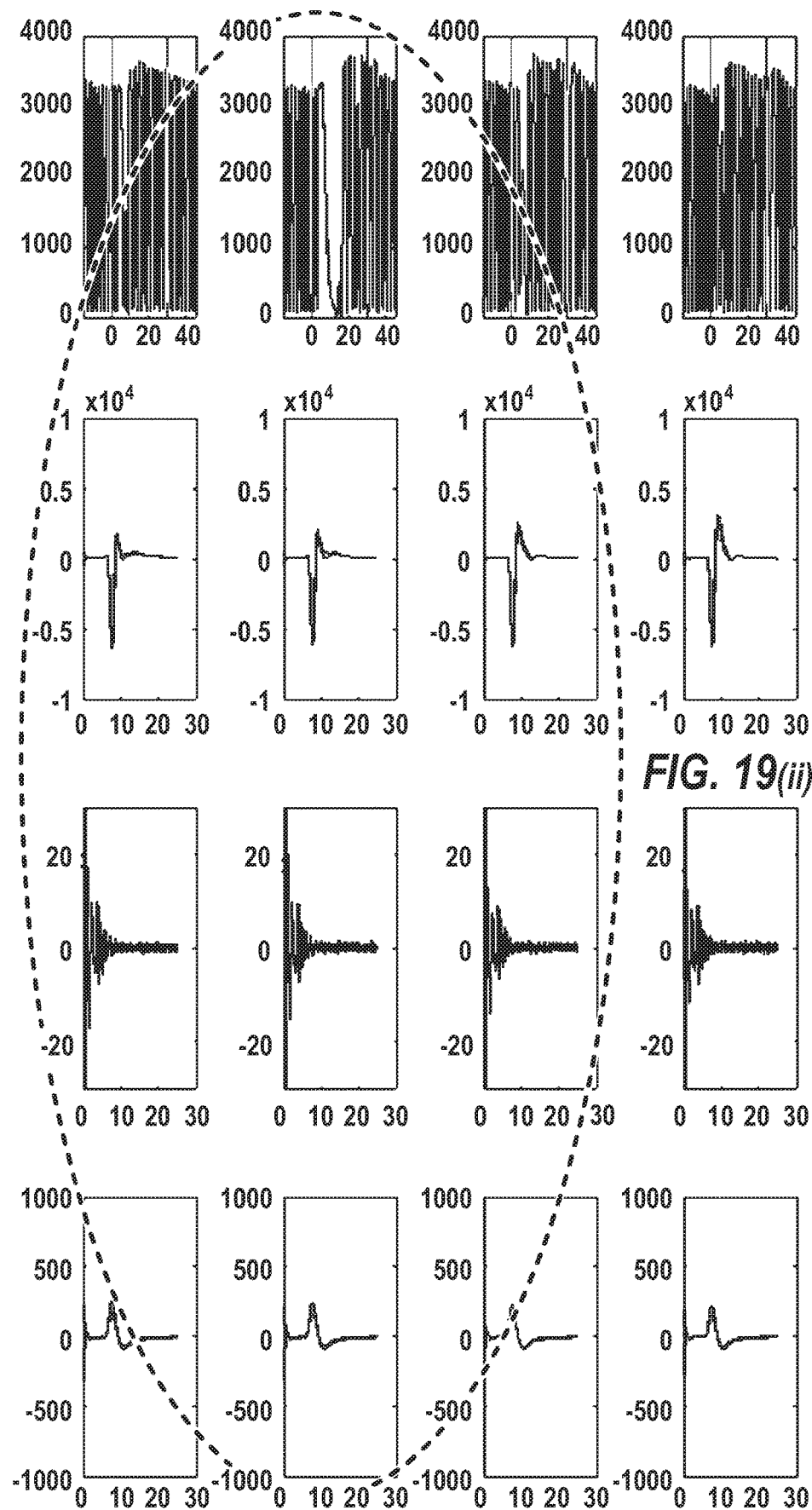
Figure 20I:
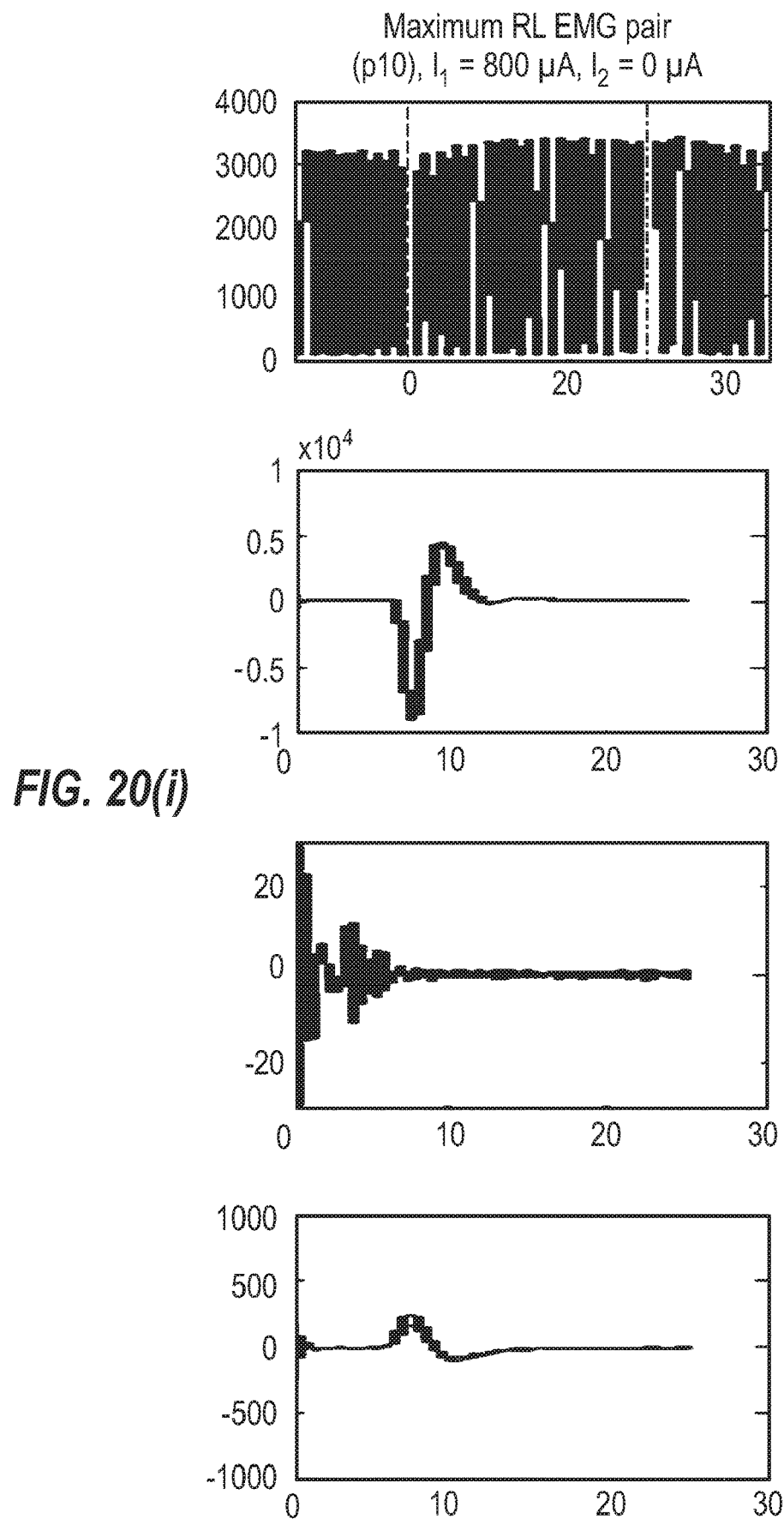
Figure 20:
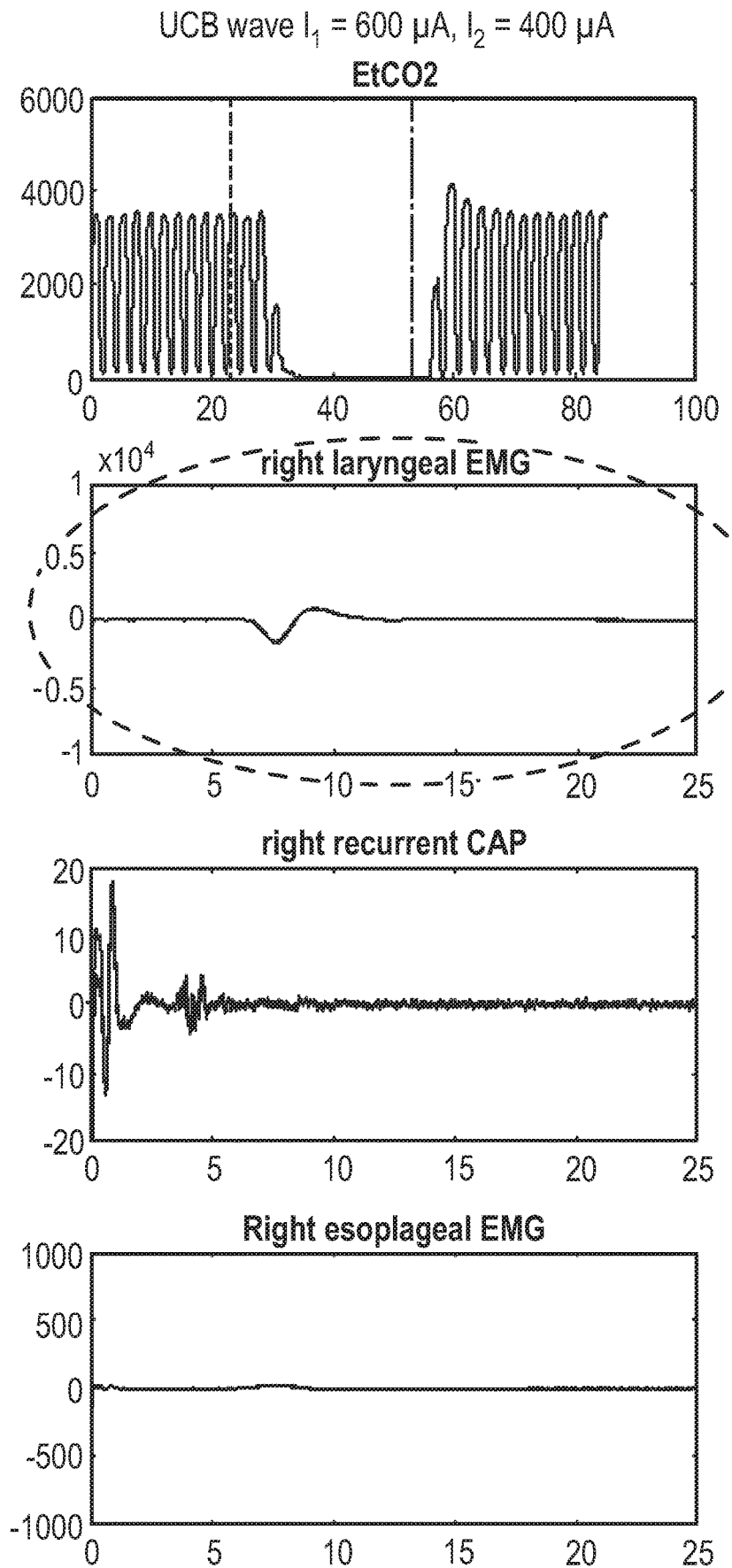
Figure 21I:
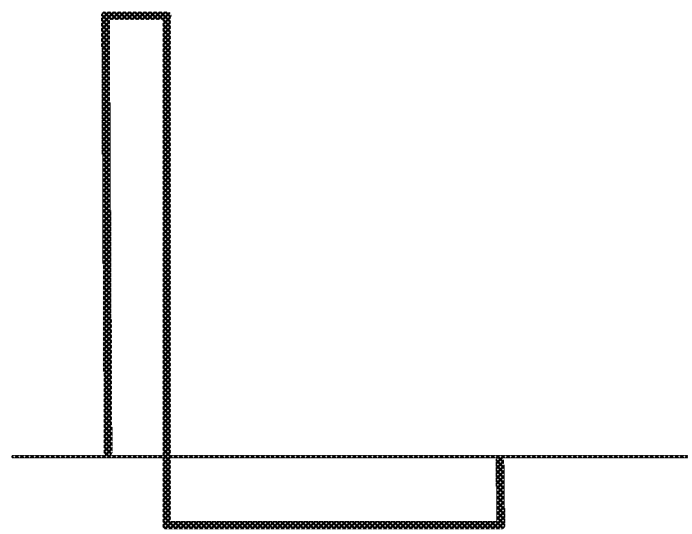

Experimental Data (FIGS. 19 to 21)

FIG. 19 illustrates the resulting measured expiratory time, recurrent laryngeal (RL) EMG, RL eCAP and esophageal eCAP as the porcine cervical vagus is acutely stimulated using a 14 pair (28 electrode) Directional and Spatially Selective (DASS-CV) neural interface. In this example, the encircled plots shows the electro pair that most closely achieves the intended effect of increasing expiratory time using the "spatial/directional" feature of the DASS-CV interface with stimulation current I1.

FIG. 20 illustrates a similar experiment as in FIG. 19 wherein the current sources I1 and I2 for the most optimal DASS-CV pair of electrode is varied to minimize the activation of the larynges and esophagus as illustrated by the corresponding EMG and eCAP measurements. In this example, a current ratio of I1=600 uA and I2=400 uA achieves the most optimal results.

FIG. 21 illustrates a similar experiment as in FIG. 20 wherein a charge balanced asymmetrical (CBA) pulse is applied to current sources I1 and I2 across the most optimal DASS-CV pair of electrode Experimental Method Naive male Hartley guinea pigs were euthanized via Intraperitoneal barbiturate injection (Fatal-Plus) according to IACUC approved protocols. Tissue was assayed and processed in Krebs-Henseleit buffer (mM): NaCl (113.0), KCl (4.8), $CaCl_2$ (2.5), $KH_2PO_4$ (1.2), $MgSO_4$ (1.2), $NaHCO_3$ (25.0), dextrose (5.55), equilibrated with 95% $O_2$: 5% $CO_2$.

Left or right vagi, spanning 40-60 mm from the nodose and jugular ganglia to the subclavian arteries with the carotid artery were removed for processing. Under dissection microscopes, the vagus was separated from the carotid artery, connective tissue, and fat and partially de-sheathed. Tissue was transferred and mounted to a custom 3 chamber tissue with surgical silk (5.0). All chambers were filled with fresh assay buffer perfused for 30-60 min at 35+/−2° C. prior to recording.

Stimulation was performed in the central chamber on the cervical vagus with custom made 500 µm platinum/iridium silicone cuff electrodes. Stimuli of varying pulse duration (PD) and current were generated with a square-pulse stimulator (Grass model S48; Natus Neurology Inc., Warwick, R.I., U.S.A.) driving an optically isolated constant current source (Model 2200; AM Systems, Seqium, Wash., U.S.A.). Quasitrapezoidal pulses were generated by the addition of a schottky diode to a parallel resistor (770-5770 Ohm)/capacitor (0.1 uF) network prior to isolation. In some cases, the quasitrapezoidal stimulus was generated via a Kiethley 3390 50 MHz arbitrary waveform generator using KI Wave software v1.2 (Tektronix, Beaverton, Oreg., U.S.A) and fed into the constant current stimulus isolator.

Stimulation was applied centrally with compound action potentials recorded on the distal and proximal vagus with a microelectrode AC amplifier (A-M Systems model 1800, Carlsborg, Wash., U.S.A.) using Ag/AgCl hook electrodes in the outside baths. Arrest side of stimulus was always oriented proximally. Differential signals were filtered with a low cut-off frequency of 10 Hz and high cut-off frequency of 1 kHz. Tissue was grounded via a platinum hook electrode in the central bath. After checking viability of tissue, the recording baths were drained and rapidly filled with pre-warmed mineral oil and recording commenced.

Analog signals were digitized at 15 kHz using an analog-to-digital converter (Power1401 625 kHz; Cambridge Electronic Design Ltd., Cambridge, England, UK) and Spike 2 software (v5.21, Cambridge Electronic Design Ltd). Non-linear regressions were performed in Graphpad Prism (v5.03, GraphPad Software, San Diego Calif. USA).

Results are normalized to the maximal area under a curve observed for given fiber type from a square pulse stimulation.

Figure 22:
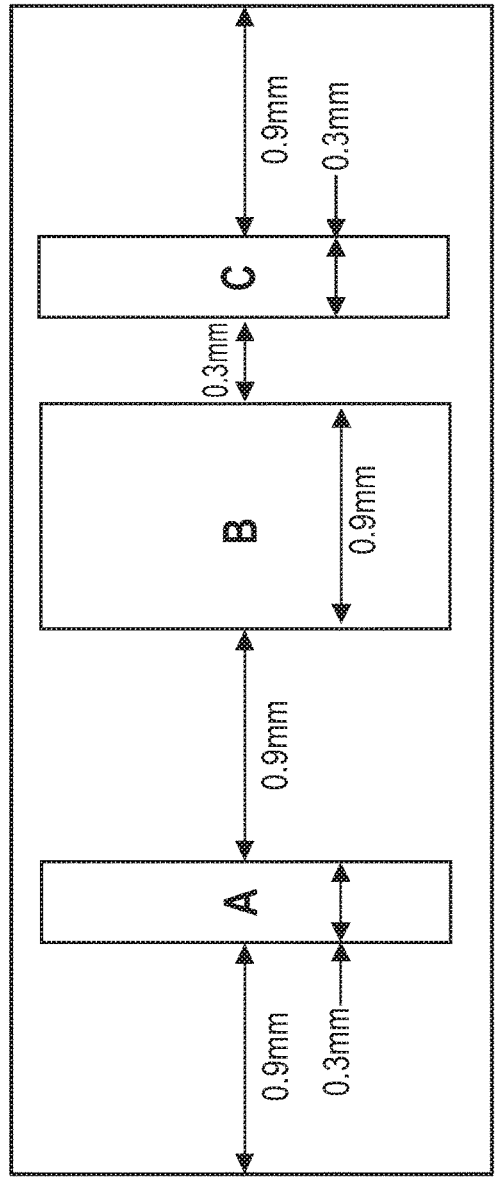
FIG. 22 illustrates an electrode configuration.

Cuff Design #1 (FIG. 22)

FIG. 22 illustrates an electrode configuration similar to that described with reference to FIG. 1*b* where there are three rings of electrodes and illustrates one triplet of electrodes of the plurality of triplets of electrodes formed by the three rings of electrodes. In this example, electrodes A and C are anodes and electrode B is a cathode.

In this example, the gap between a first end of the cuff is 0.9 mm; the width of electrode A is 0.3 mm; the gap between electrode A and electrode B is 0.9 mm; the width of electrode B is 0.9 mm; the gap between electrode B and electrode C is 0.3 mm; the width of electrode C is 0.3 mm; and the gap between a second end of the cuff is 0.9 mm.

In this configuration the first and the third electrode are equal in width and have the same surface area. The width of second electrode is three times that of the first or the third electrode. The gap between the third and the second electrode is three times that of the gap between the first and the second electrode.

Figure 23:
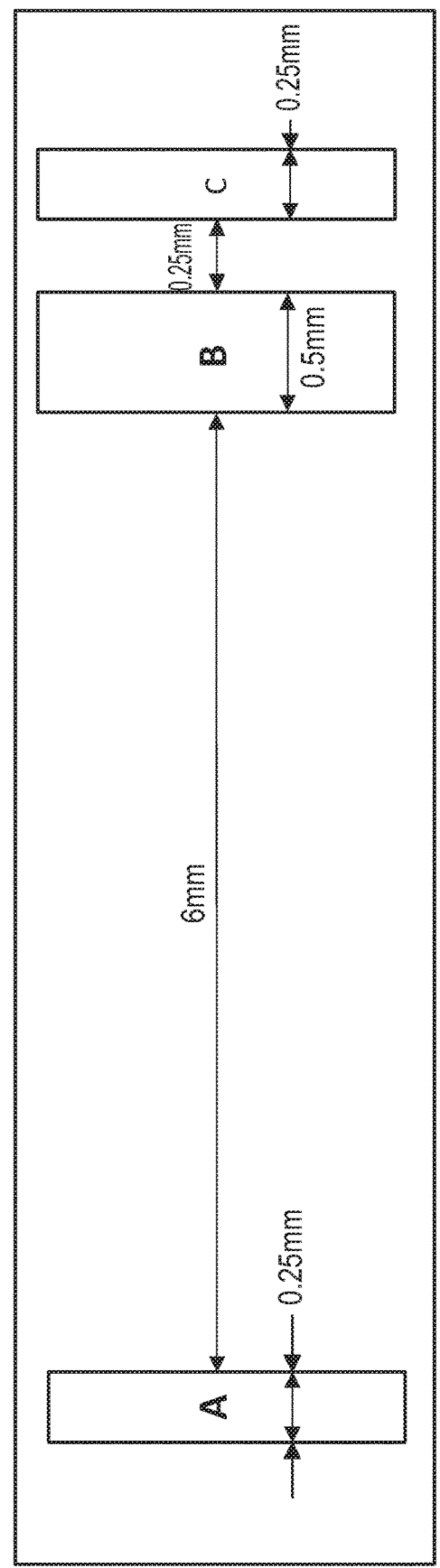
FIG. 23 illustrates another electrode configuration.
Figure 24A:
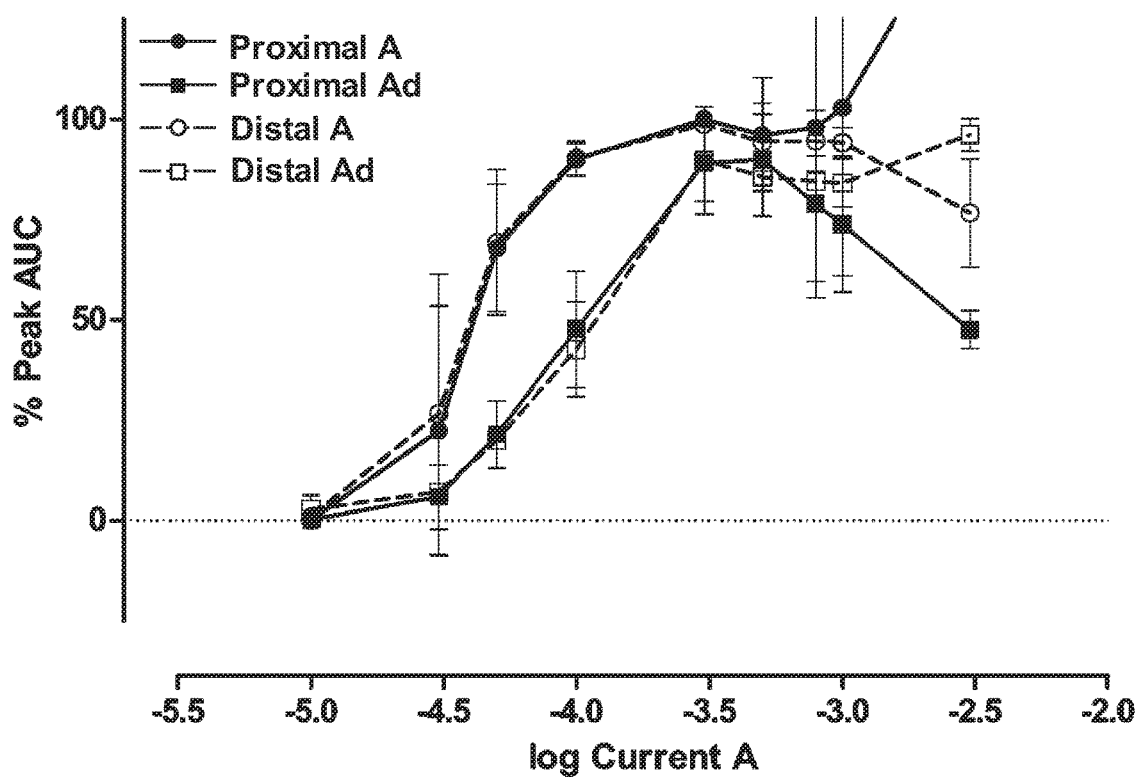
FIGS. 24A-D illustrate action potential propagation distal and proximal to a central electrode array when the electrode configuration described with reference to FIG. 22 is stimulated in a bipolar manner with a square pulse.
Figure 24B:
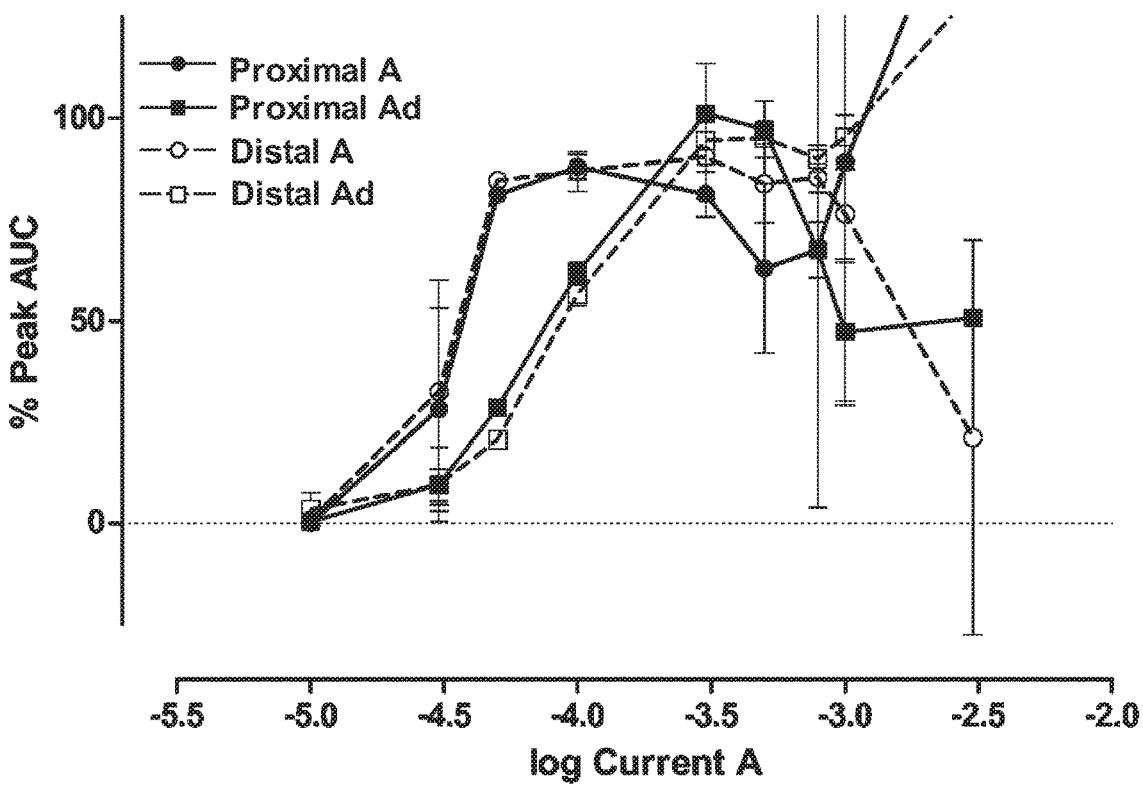
Figure 24C:
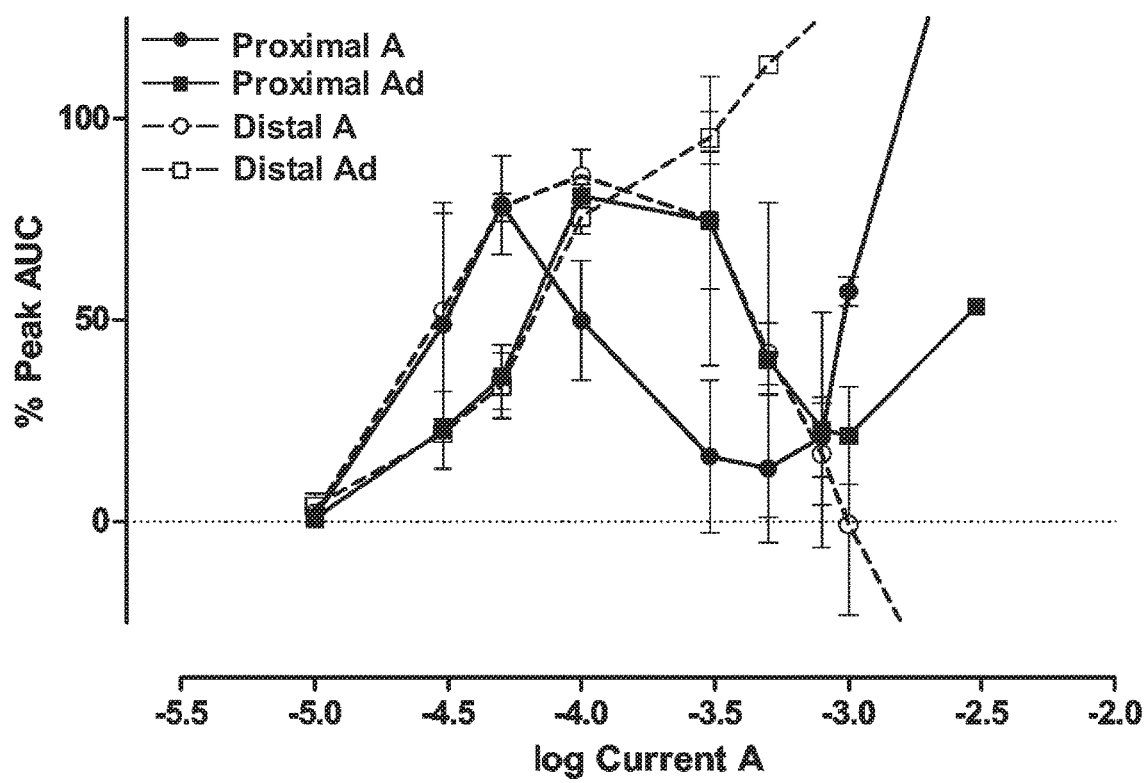
Figure 24D:
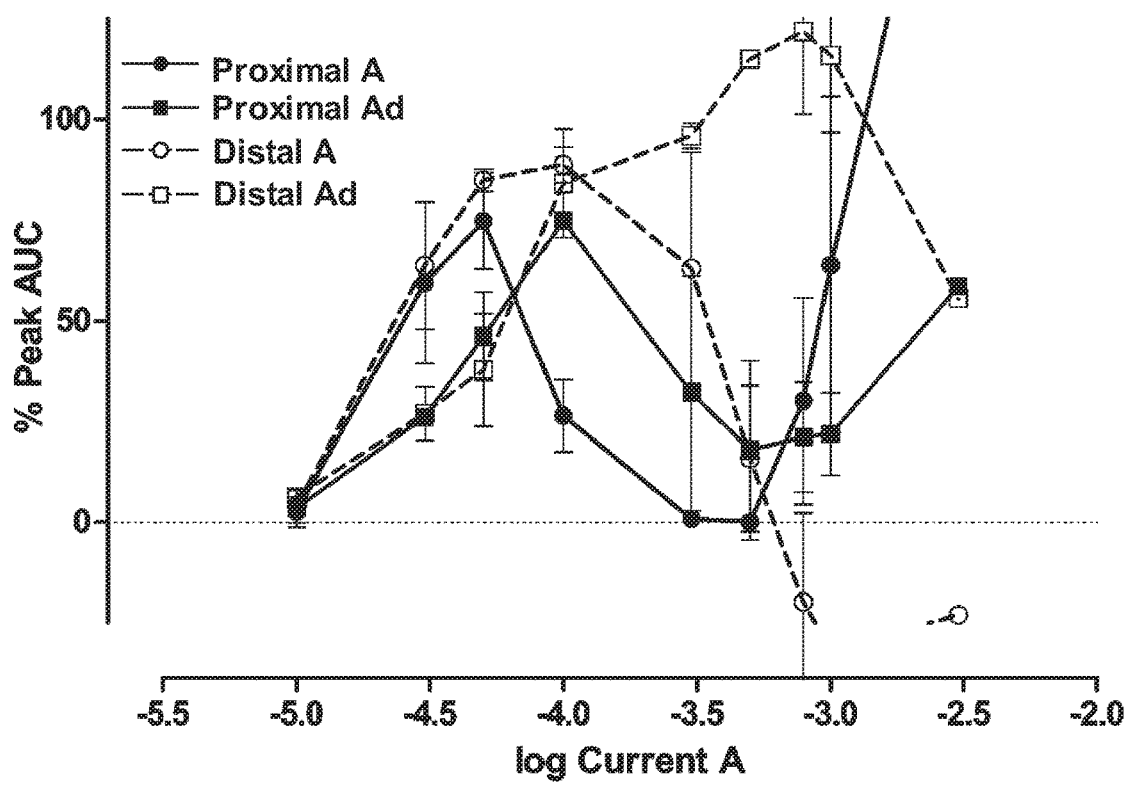
Figure 25A:
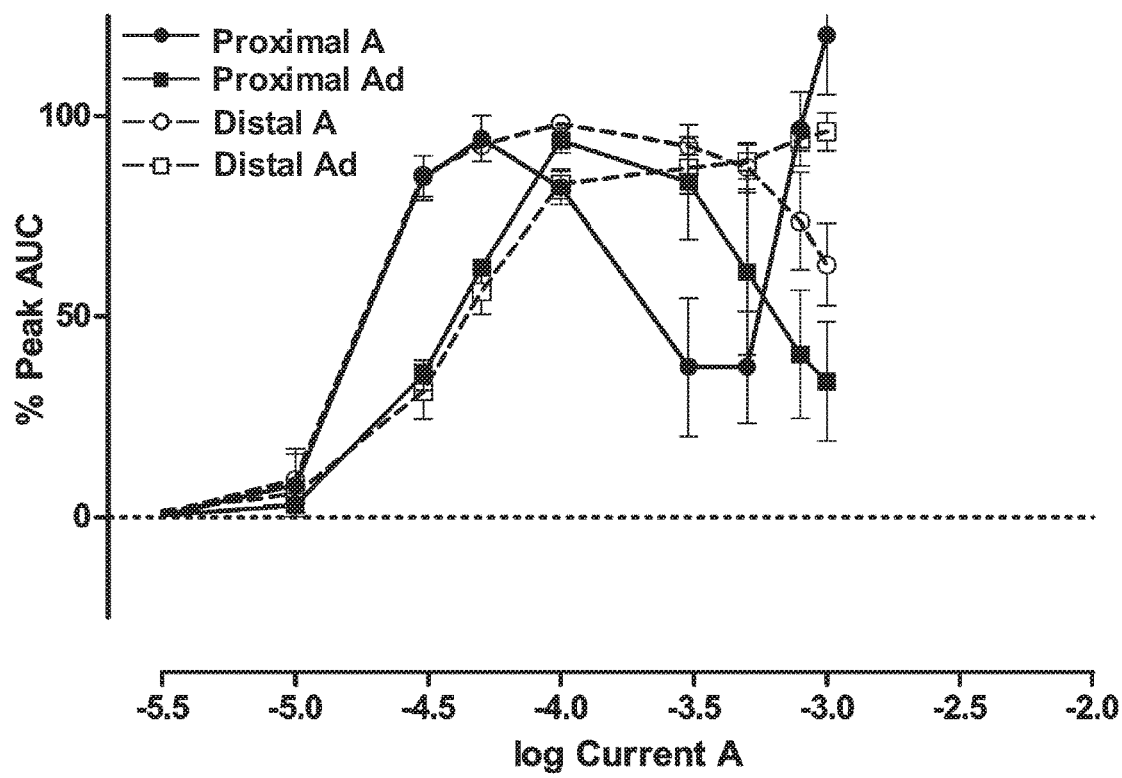
FIGS. 25A-D illustrate action potential propagation distal and proximal to a central electrode array when the electrode configuration described with reference to FIG. 22 is stimulated in a bipolar manner with a quasitrapezoidal pulse.
Figure 25B:
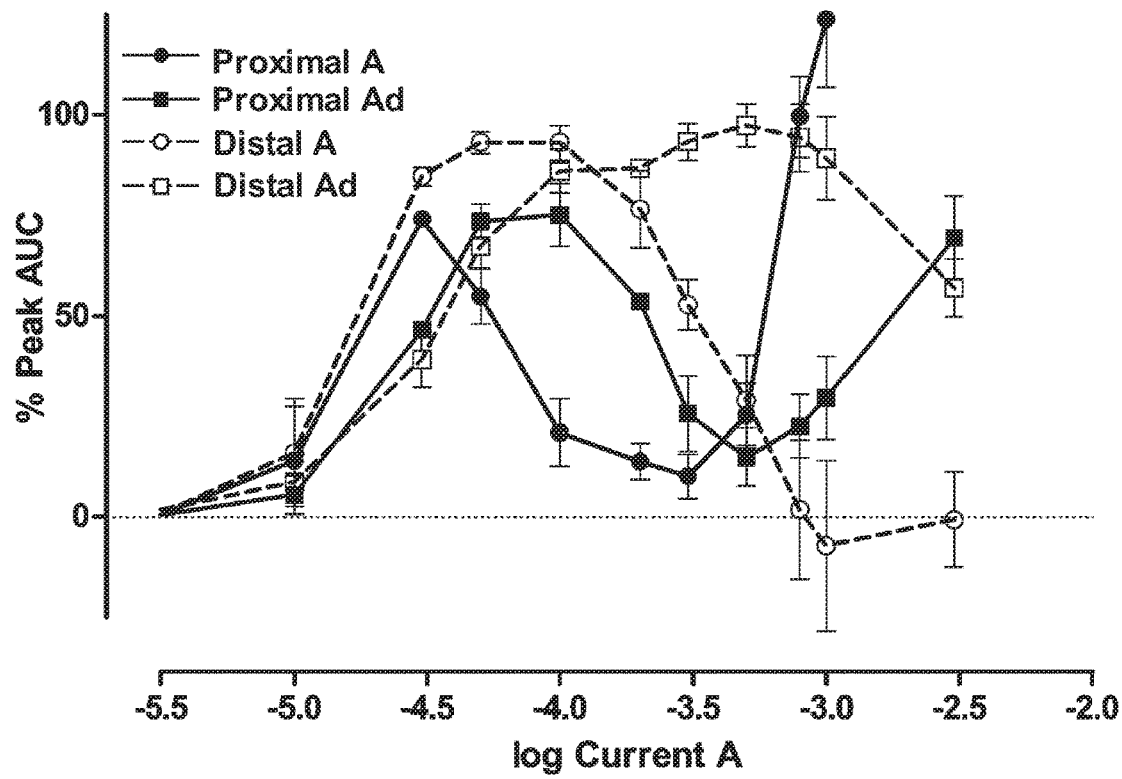
Figure 25C:
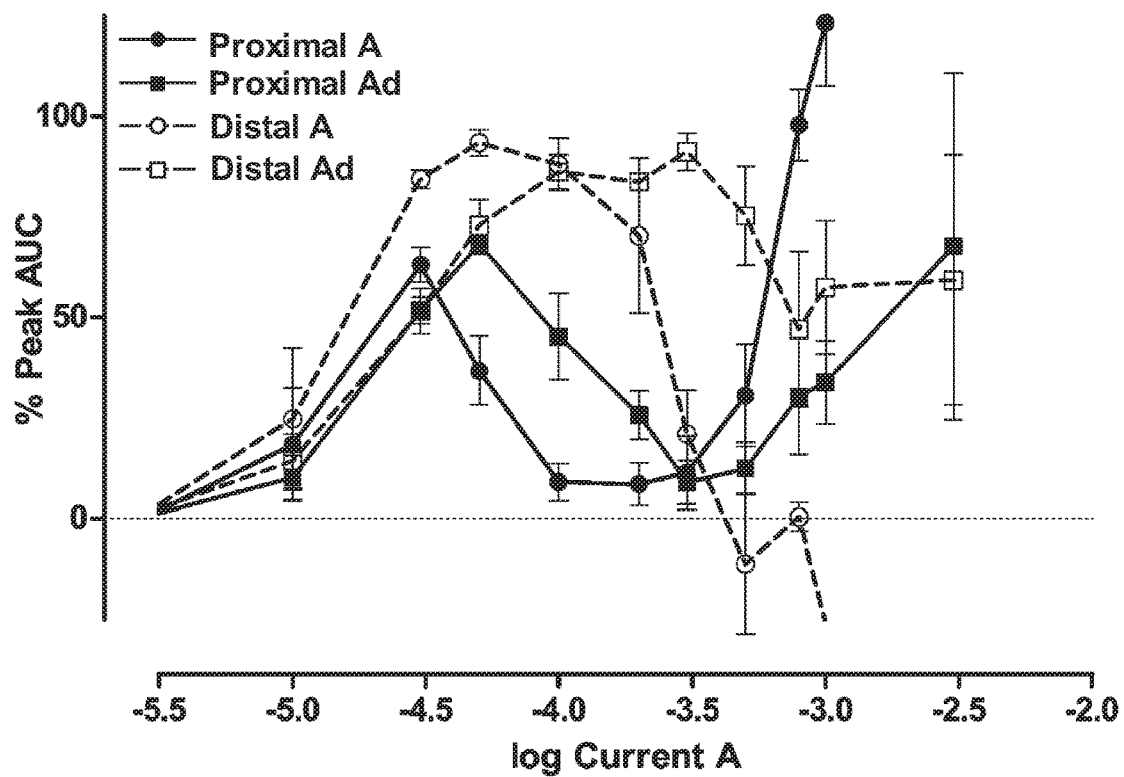
Figure 25D:
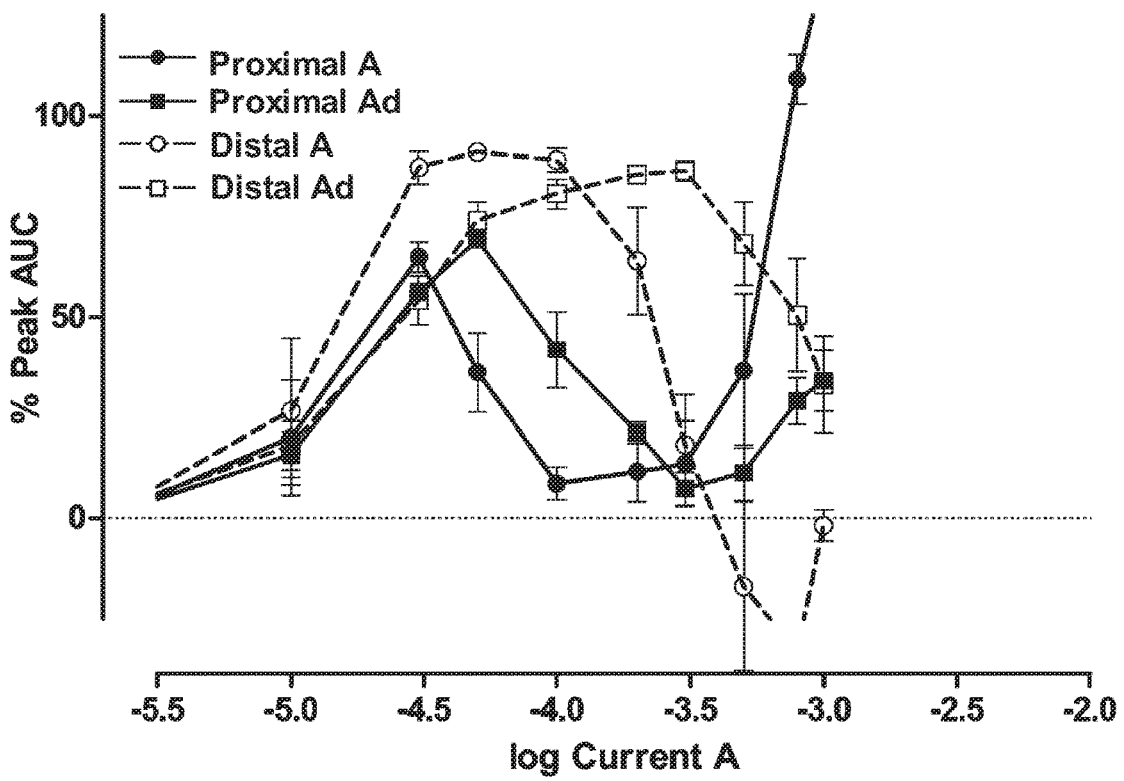
Figure 27A:
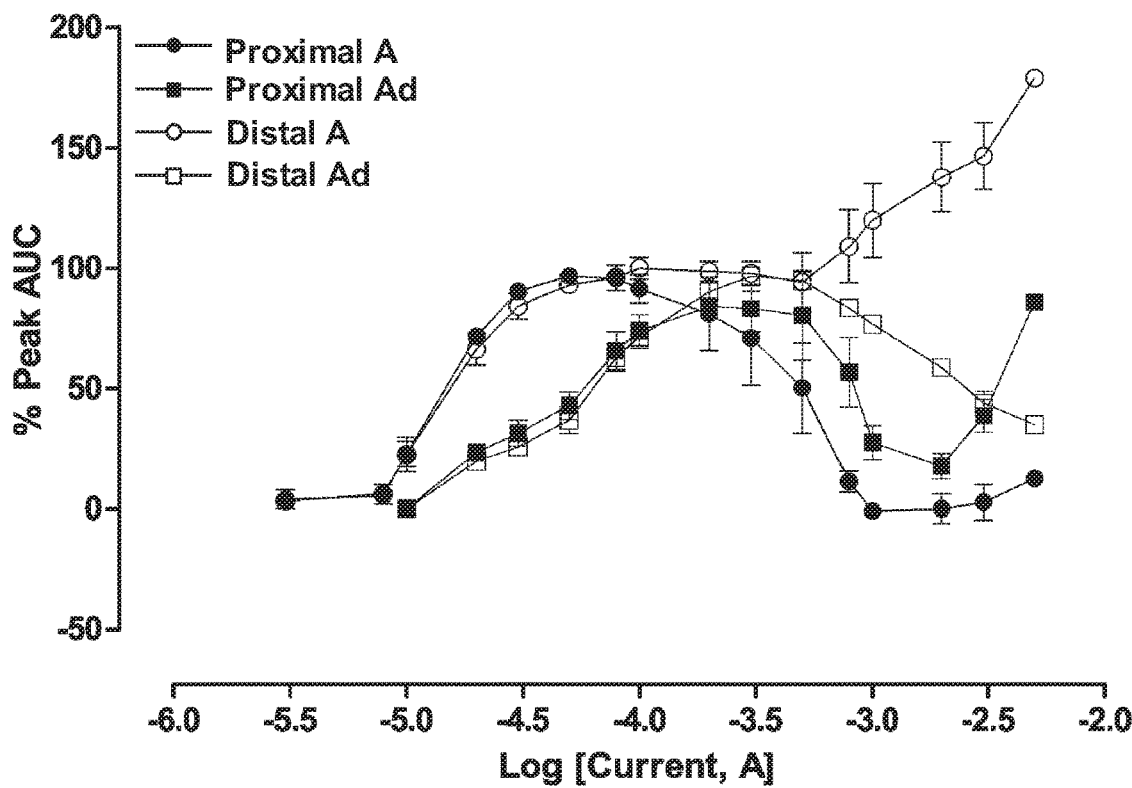
FIGS. 27A-D illustrate action potential propagation distal and proximal to a central electrode array when the electrode configuration described with reference to FIG. 23 is stimulated in a tripolar manner with a quasitrapezoidal pulse.
Figure 27B:
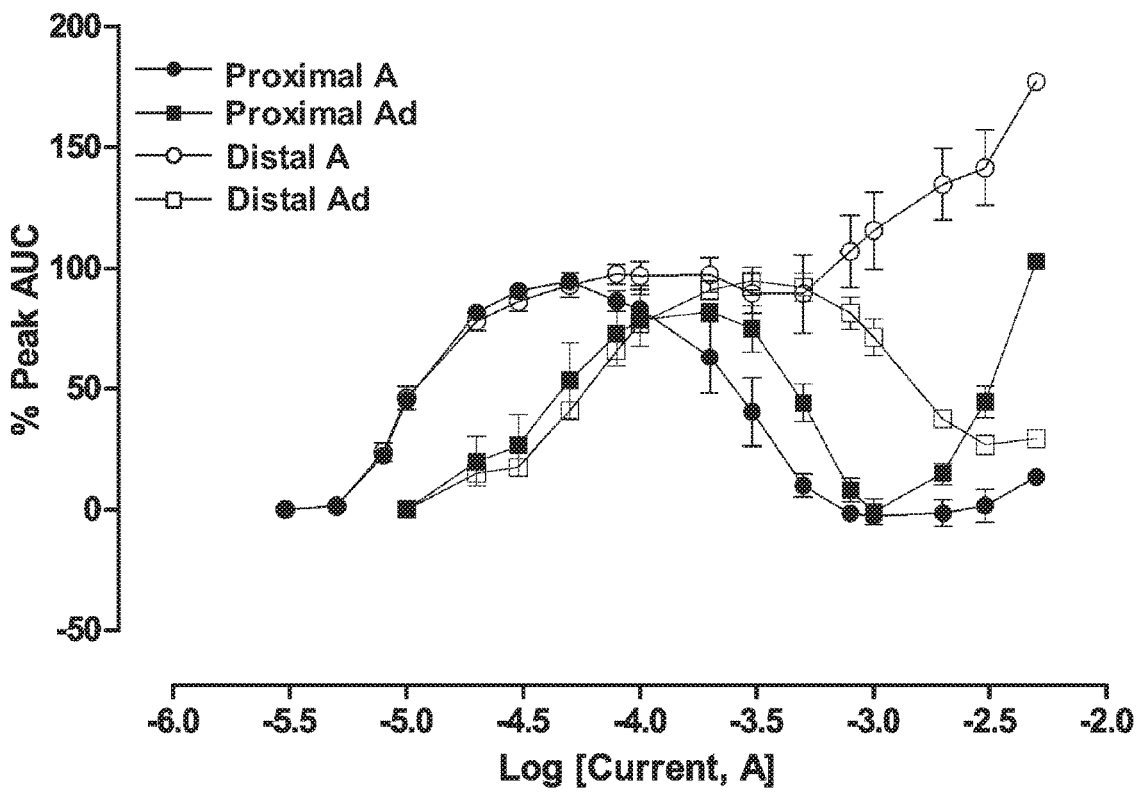
Figure 27C:
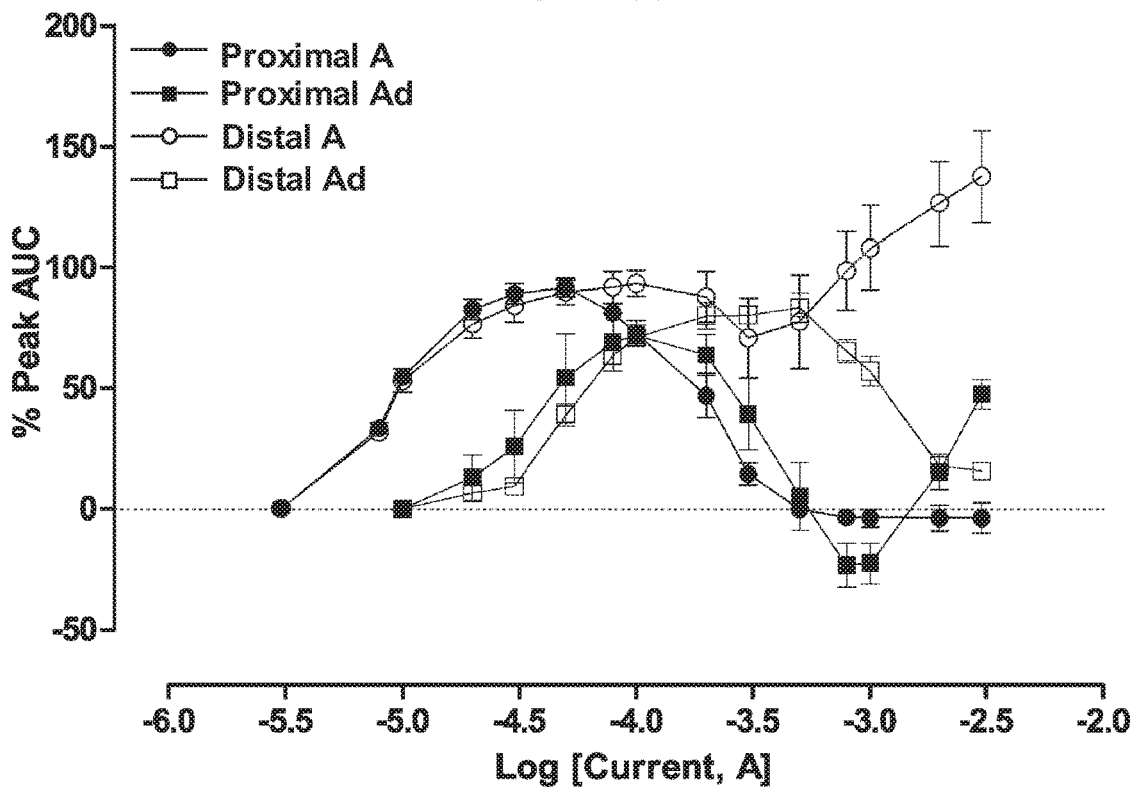
Figure 27D:
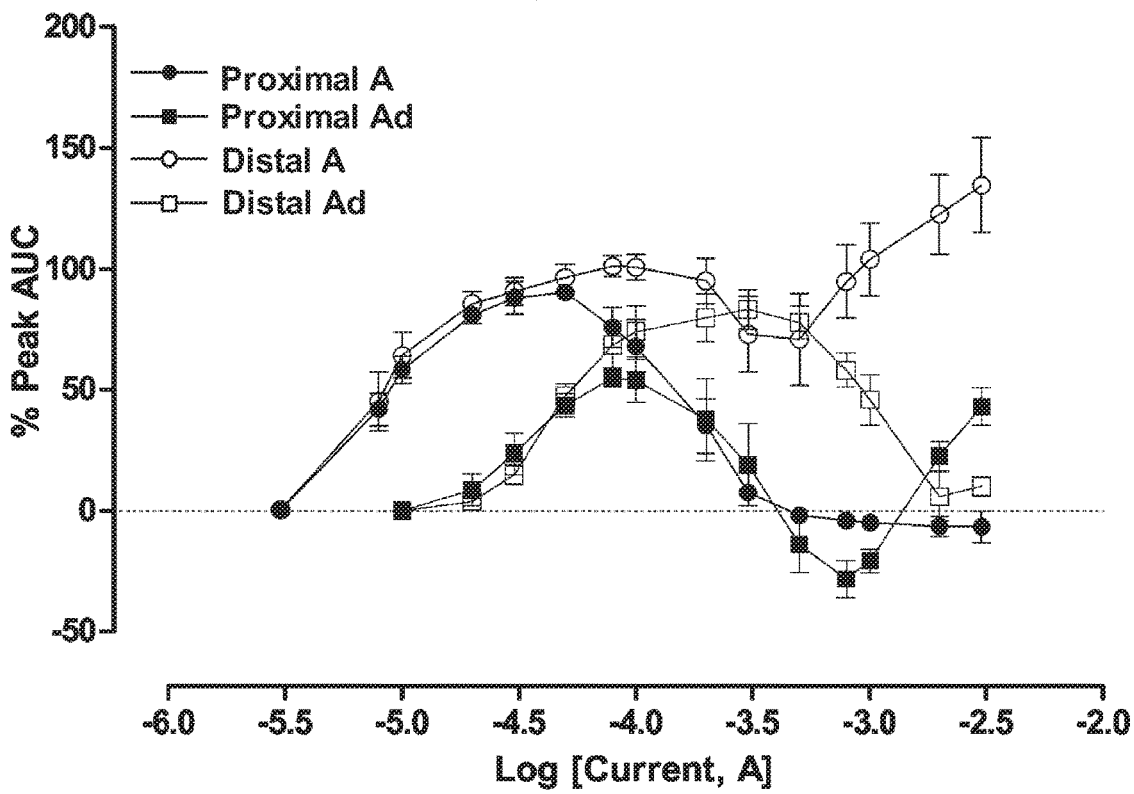

Cuff Design #2 (FIG. 23)

FIG. 23 illustrates an electrode configuration similar to that described with reference to FIG. 1*b* where there are three rings of electrodes and illustrates one triplet of electrodes of the plurality of triplets of electrodes formed by the three rings of electrodes. In this example, electrodes A and C are anodes and electrode B is a cathode.

In this example, the width of electrode A is 0.25 mm; the gap between electrode A and electrode B is 6 mm; the width of electrode B is 0.5 mm; the gap between electrode B and electrode C is 0.25 mm; and the width of electrode C is 0.3 mm.

In this configuration the first and the third electrode are equal in width and have the same surface area. The width of second electrode is two times that of the first or the third electrode. The gap between the third and the second electrode is twenty-four times that of the gap between the first and the second electrode.

Experimental Results (FIGS. 24A-D)

FIGS. 24A-D illustrate the results of bipolar square pulse stimulation (0.1-0.6 msec, monophasic) of a guinea pig vagus using cuff design #1 where the cathode (electrode B) is three times the geometric surface area of the anode (electrode C). These results are for stimulation of a pair of electrodes (i.e. electrodes B and C); however, these results can be extended to multiple pairs of electrodes formed by the two rings of electrode arrays.

The pulse durations (0.1-0.6 msec) refer to the duration of the pulse where the peak amplitude is provided (i.e. the plateau of the square wave). The stimulation was provided with one current source attached to the cathode and an anode (i.e. 'passive stimulation' was provided).

The A fibers (having a conduction velocity of ~>10 m/s) are donated by the red circles. The Ad fibers (having a conduction velocity of ~10-3 m/s) are denoted by the blue squares. A pulse width (plateau phase) dependent suppression of compound action potential propagation can be observed in the proximal direction (solid symbols) for both A and Ad fiber types, with a preference for propagation distally (open symbols). A virtual cathode/anode formation occurs close to 1 mA.

Experimental Results (FIGS. 25A-D)

FIGS. 25A-D illustrate the results of bipolar quasitrapezoidal stimulation (0.1-0.6 msec plateau phase, >200 us decay) of guinea pig vagus using cuff design #1 where the cathode (electrode B) is 3× the geometric surface area of the anode (electrode C). These results are for stimulation of a pair of electrodes (i.e. electrodes B and C); however, these results can be extended to multiple pairs of electrodes formed by the two rings of electrode arrays.

The pulse durations (0.1-0.6 msec) refer to the duration of the pulse where the peak amplitude is provided (i.e. the plateau of the quasitrapezoidal wave before the amplitude begins to decay). The stimulation was provided with one current source attached to the cathode and an anode (i.e. 'passive control' was provided).

The A fibers (having a conduction velocity of ~>10 m/s) are denoted by the red circles. The Ad fibers (having a conduction velocity of ~10-3 m/s) are denoted by the blue squares. A pulse width (plateau phase) dependent suppression of compound action potential propagation can be observed in the proximal direction (solid symbols) for both A and Ad fiber types, with a preference for propagation distally (open symbols). Virtual cathode/anode formation occurs close to 1 mA. Quasitrapezoidal stimulation conveys a benefit (lower current requirements to achieve directionality) over square wave stimulation to achieve directionality. The pulse durations (0.1-0.6 msec) refer to the duration of the pulse where the peak amplitude is provided (i.e. the plateau of the quasitrapezoidal wave before the amplitude begins to decay).

Experimental Results (FIGS. 26A-D)

FIGS. 26A-D illustrate the results of tripolar quasitrapezoidal stimulation (0.1-0.6 msec plateau phase, >200 us decay) of guinea pig vagus using cuff design #1 where the cathode (electrode B) is 3× the geometric surface area of the anodes (electrode A and C). These results are for stimulation of a triplet of electrodes (i.e. electrodes A, B and C); however, these results can be extended to multiple triplets of electrodes formed by the three rings of electrode arrays.

Positive output of a single stimulator is shorted to the outer two electrodes. A differential charge density on anodes is achieved through design spacings only, using a single current stimulator. The stimulation was provided with one current source attached to central cathode and both anodes (i.e. 'passive control' was provided).

The A fibers (having a conduction velocity of ~>10 m/s) are denoted by the red circles. The Ad fibers (having a conduction velocity of ~10-3 m/s) are denoted by blue squares. A pulse width (plateau phase) dependent suppression of compound action potential propagation can be observed in both proximal (solid symbols) and distal (open symbols) directions for both A and Ad fiber types. Virtual cathode/anode formation no longer occurs in tripolar configuration. The C-fibers (denoted by green triangles) are shown for reference. This configuration allows a preference for high threshold fibre types with a suppression of lower threshold fibre types in both directions.

Experimental Results (FIGS. 27A-D)

FIGS. 27A-D illustrate the results of tripolar quasitrapezoidal stimulation (0.1-0.6 msec plateau phase, >200 us decay) of guinea pig vagus using cuff design #2 where cathode (electrode B) is 2× the geometric surface area of the anodes (electrode A and C). These results are for stimulation of a triplet of electrodes (i.e. electrodes A, B and C); however, these results can be extended to multiple triplets of electrodes formed by the three rings of electrode arrays.

Positive output of a single stimulator is shorted to the outer two electrodes. A differential charge density on the anodes is achieved through design spacings only, using a single current stimulator). The stimulation was provided with one current source attached to the central cathode and both anodes (i.e. 'passive control' was provided).

The A fibers (having a conduction velocity of ~>10 m/s) are denoted by the red circles. The Ad fibers (having a conduction velocity of ~10-3 m/s) are denoted by the blue squares. A pulse width (plateau phase) dependent suppression of compound action potential propagation can be observed in the proximal direction (solid symbols) for both A and Ad fiber types, with a preference for propagation distally (open symbols). Virtual cathode/anode formation occurs close to 1 mA.

Figure 28I:
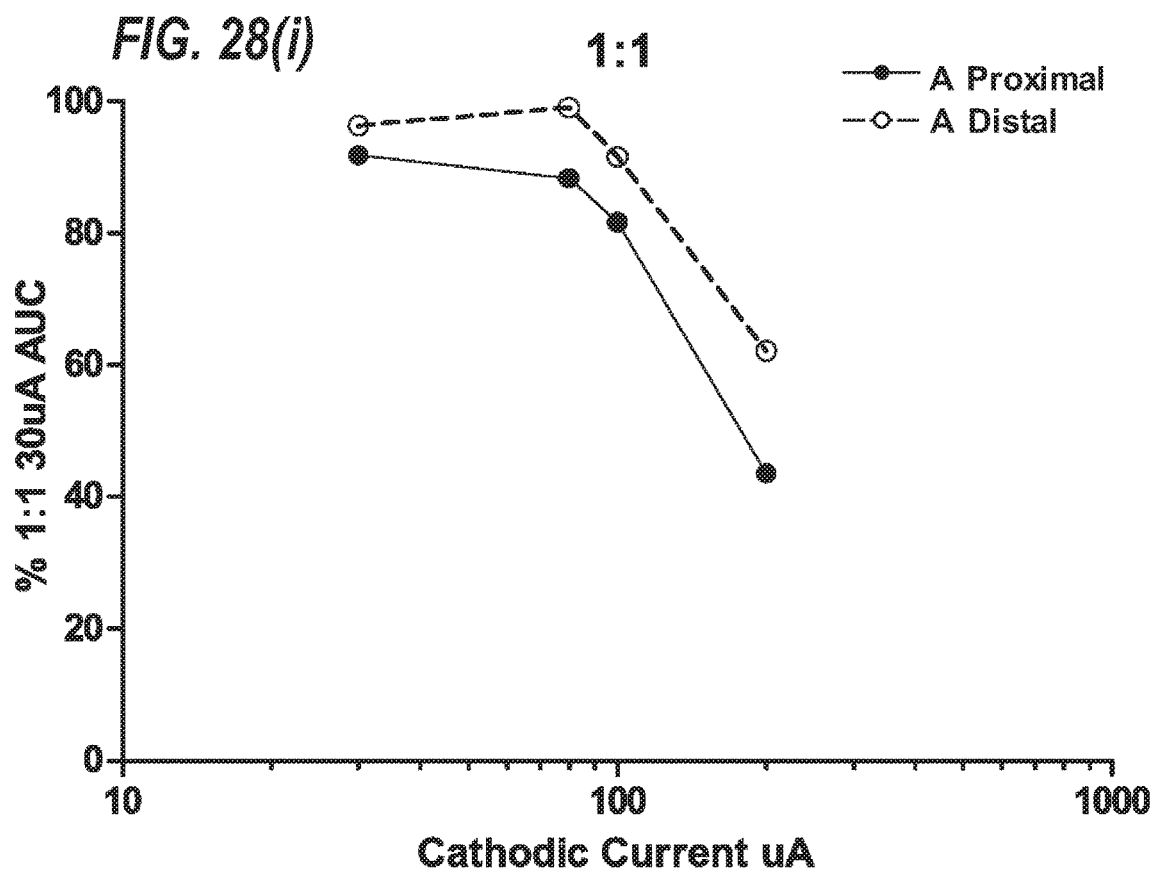
FIG. 28 illustrates action potential propagation when the electrode configuration of described with reference to FIG. 22 is stimulated in a tripolar manner with a quasitrapezoidal pulse utilizing two current sources.
Figure 28:
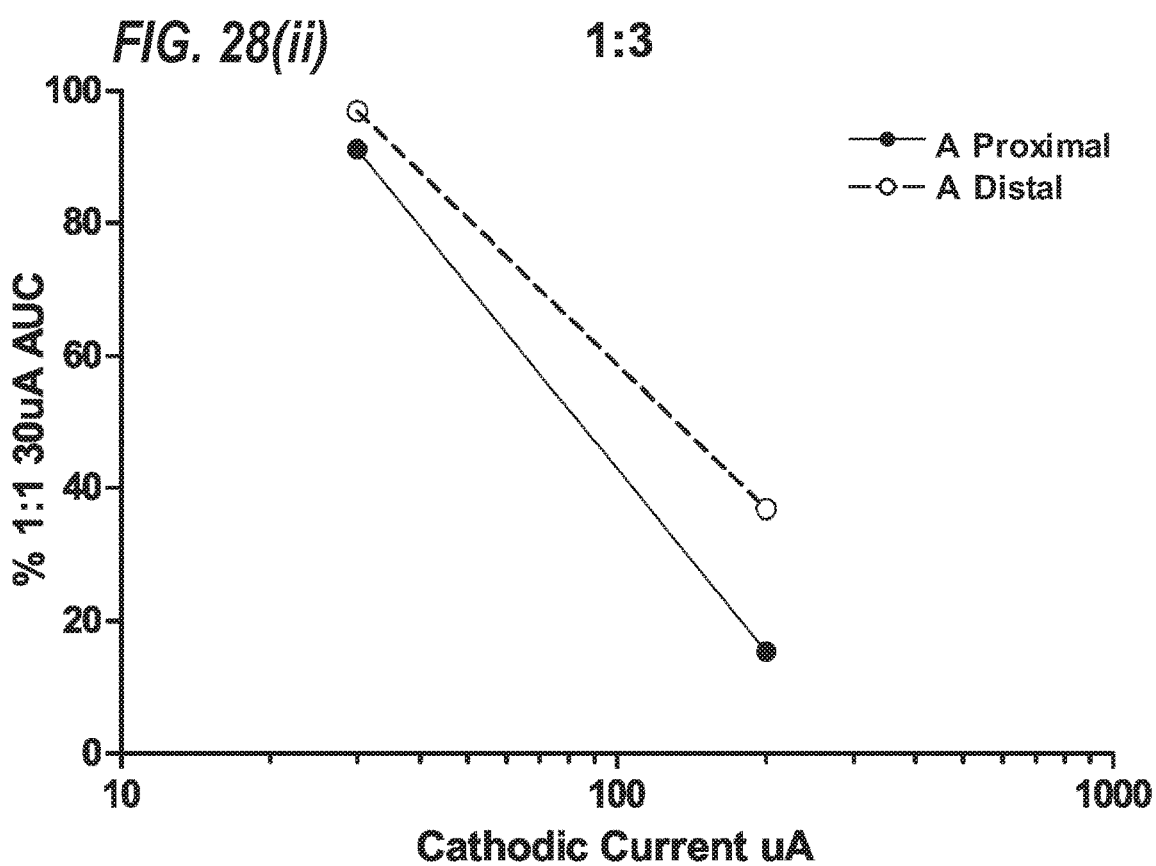
Figure 28:
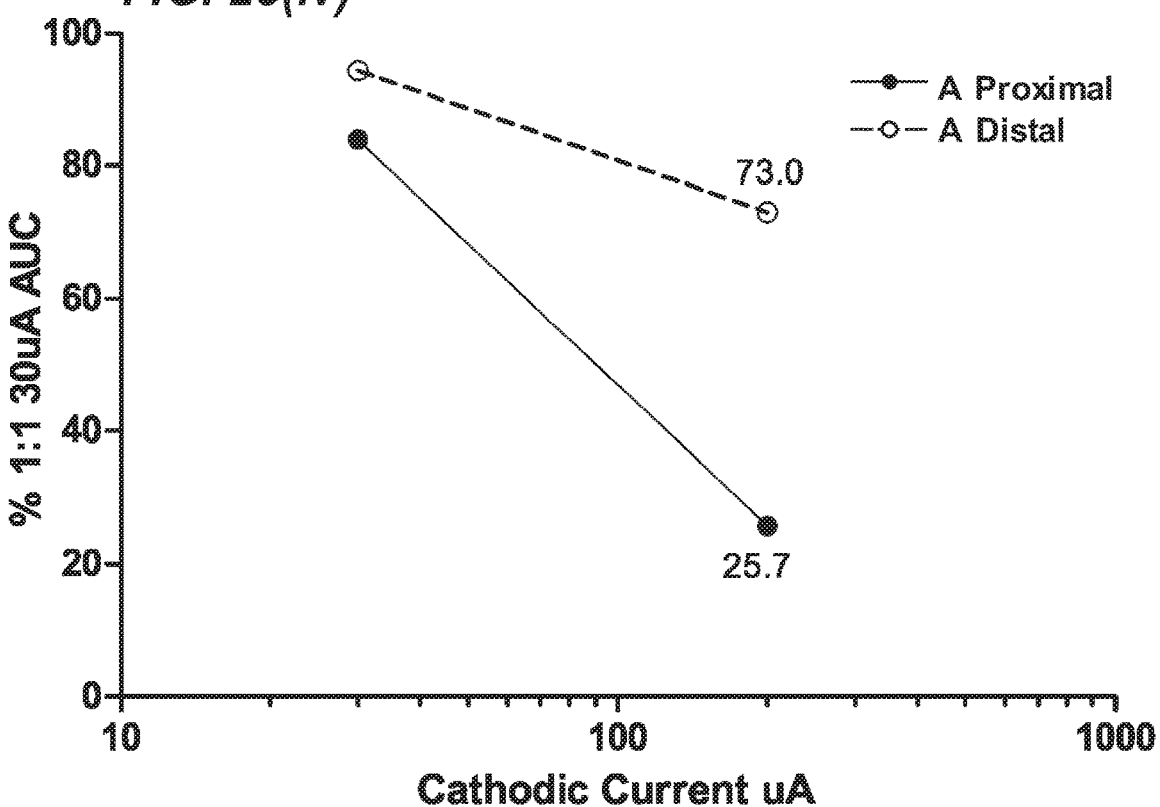
Figure 28V:
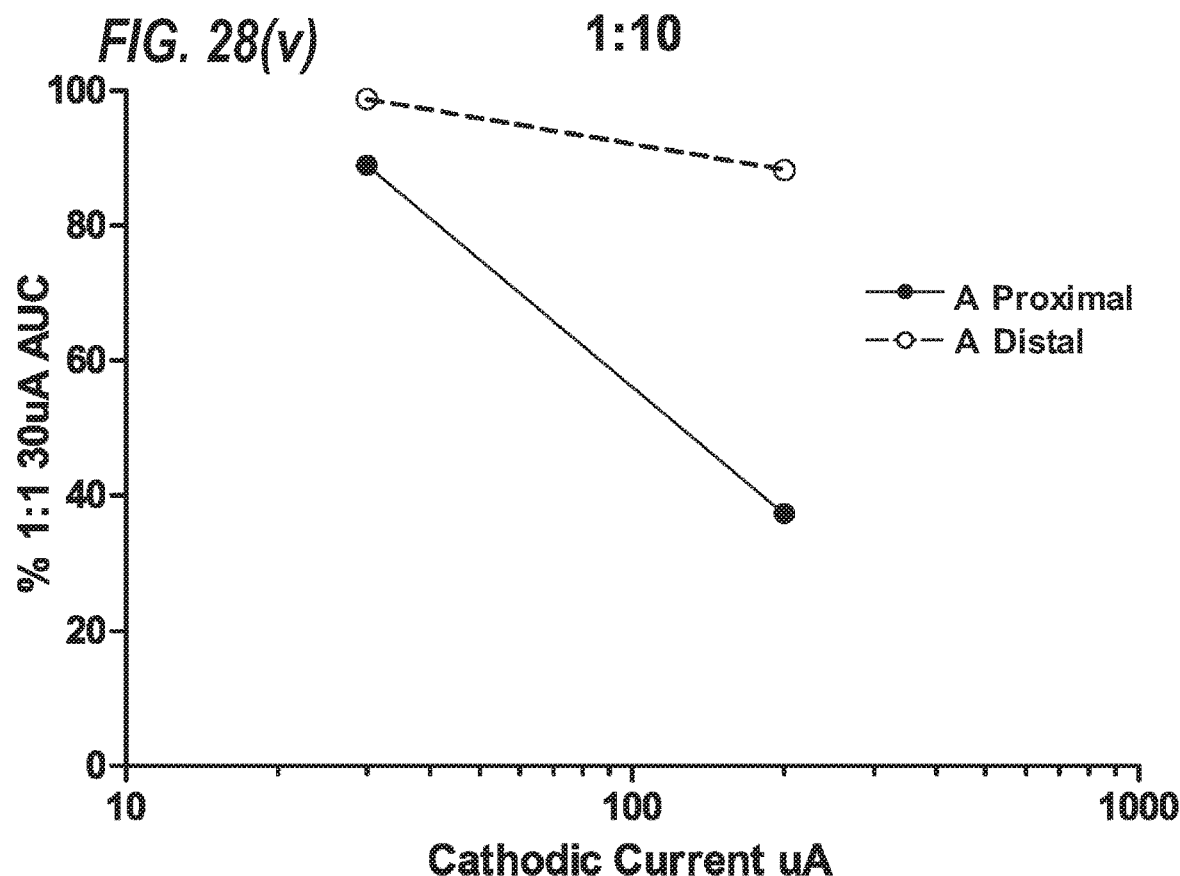
Figure 28:
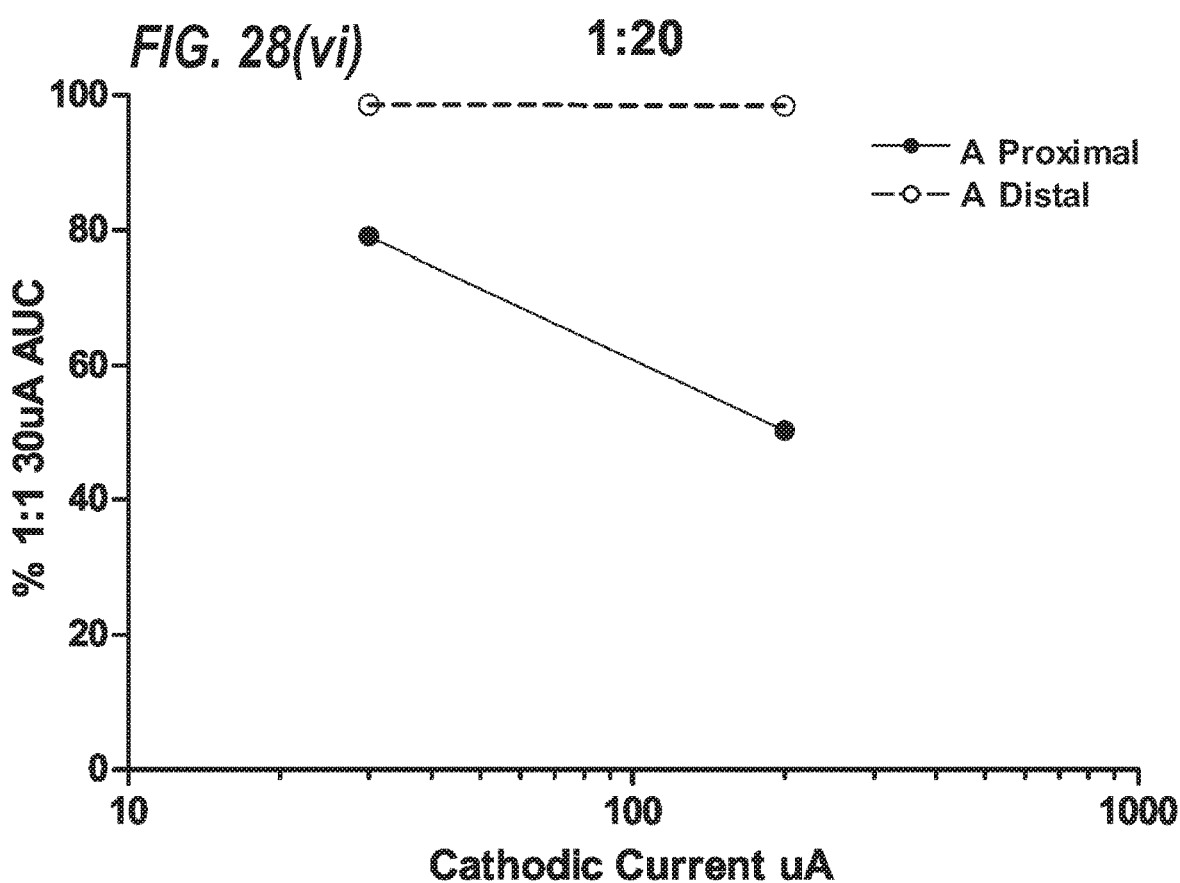

Experimental Results (FIG. 28)

The charts illustrated in FIG. 28 show the results of using tripolar quasitrapezoidal stimulation (0.4 msec plateau phase, >200 us decay) of a guinea pig vagus using cuff design #1 with a dual current stimulator configuration. These results are for stimulation of a triplet of electrodes (i.e. electrodes A, B and C); however, these results can be extended to multiple triplets of electrodes formed by the three rings of electrode arrays.

In this example, two current sources are utilized to differentially control the arresting anode charge density (i.e. 'active control was applied). The plateau width and decay time constants for both waveforms were matched and only amplitude varied. The reported cathodic amplitude is the sum of both stimulator amplitudes.

The amplitude ratios between the escape and arrest anode varied from 1:1 (50% of total current on arresting electrode) to 1:20 (95% of total current on the arresting anode) and 0:1 (bipolar, 100% of current on arresting anode) served as a comparator. The effect of varying the escape (distal facing) to arresting (proximal facing) anode current ratios are shown for A fibers having a conduction velocity of ~>10 m/s (red circles).

The percentage of maximal AUC for proximal propagation (solid circles compared to the percentage of maximal AUC for distal propagation (open circles) are shown for varying escape/arrest anode current ratios . . . . A preference for distal compared to proximal eCAP propagation (as illustrated by the blue squares) at 200 uA is shown for all configurations. A preference for directionality was maximized with 85% of current on the arresting anode (1:6.7).

Figure 29A:
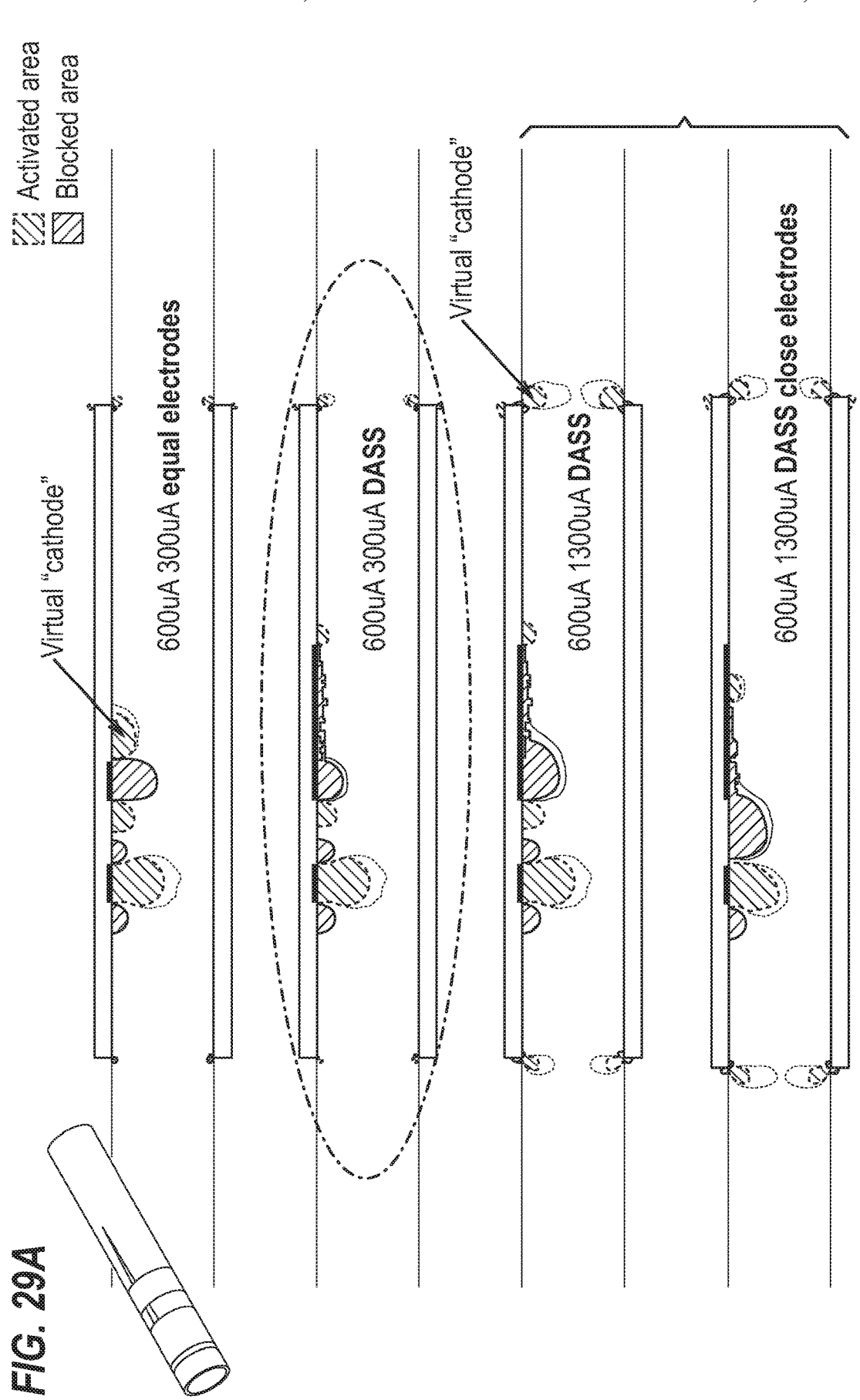
FIGS. 29A-B illustrate a cuff doped with conductive particles.
Figure 29B:
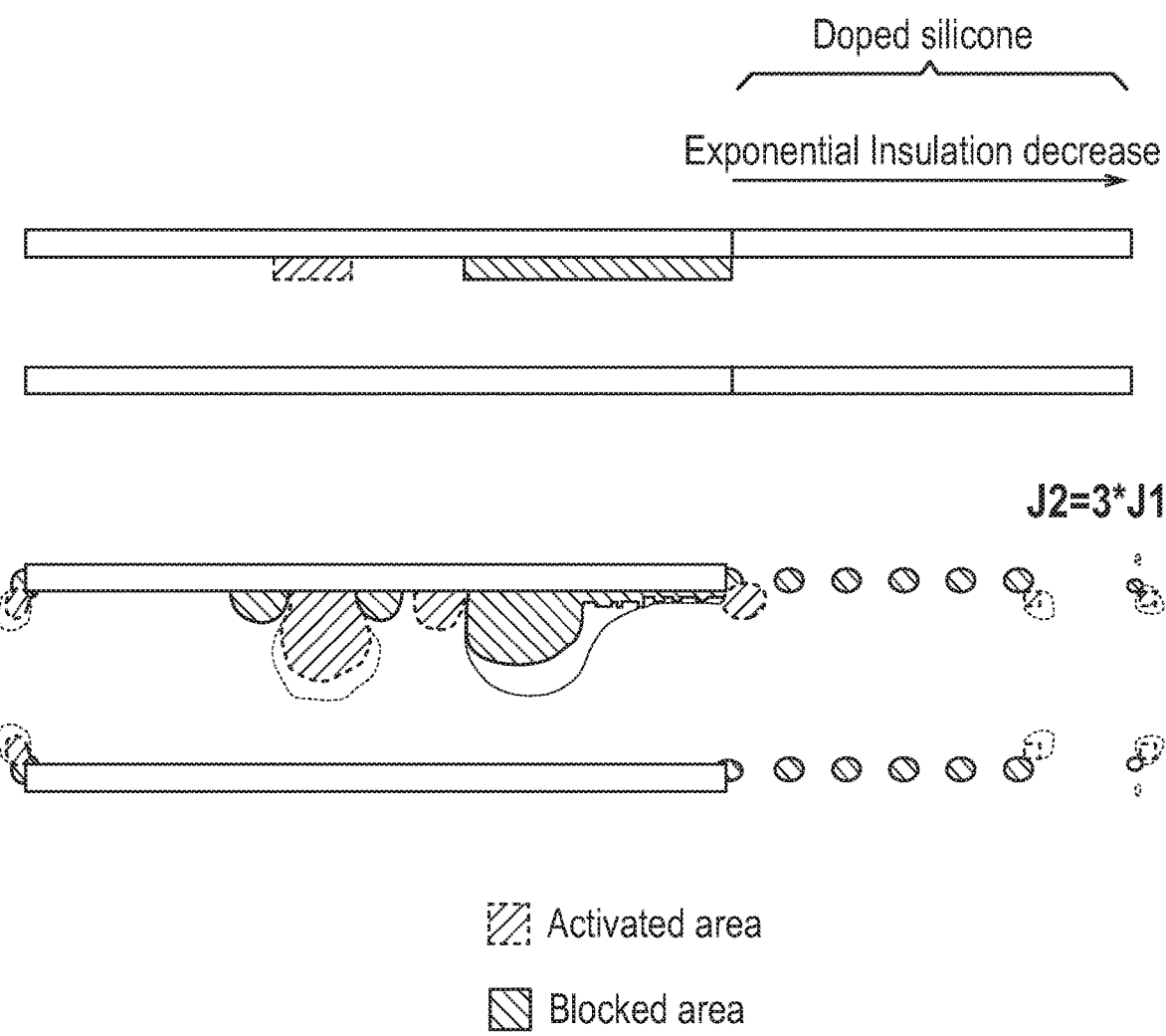

Doped Silicon Cuff End with Conductive Particles (FIGS. 29A and 29B)

It was described above that one aspect of the disclosure is to reduce virtual cathode which may be created around the anode when trying to block action potential, where such reduction of virtual cathode is achieved by providing impedance matching between the anode and the surrounding tissue.

By providing impedance matching between the anode and the surrounding tissue (which surrounds the anode itself or the cuff on which the anode is positioned), it is possible to reduce virtual cathode and thereby apply higher currents to stimulate higher threshold nerves with directional selectivity in a reliable manner.

In one embodiment, such impedance matching is achieved by gradually increasing the resistance of the cuff along the length of the cuff in the direction away from the cathode. In other words, the resistance of the cuff is gradually reduced from the edge of the cuff which contacts the tissue to the edge of the anode (more specifically the edge which is further away from the cathode). An example embodiment is illustrated in FIG. 31B.

In more detail, FIGS. 31A-B illustrate an example electrode configuration in which the cuff upon which the electrodes are mounted has conductive particles included within it. The cuff may comprise silicon, and this silicon material can be doped with conductive particles. This assists in mitigating against virtual cathodes at the ends of the cuff. The silicon cuff may be doped with conductive particles towards an end or towards both of its ends.

Referring to FIG. 29A, two current sources (J1, J2) are applied to the electrodes as described with reference to FIGS. 15, 16 and 18; J1=600 uA while J2 is varied. Increasing J2 has the desirable effect as increasing the blocking area (shown in blue) but the undesirable appearance of virtual cathodes forming at the edges of the cuff (shown in red). To mitigate this effect, as illustrated in FIG. 29B, the silicone between the anode and the right edge of the cuff can be loaded with conductive particles to form an impedance matching layer. This impedance match layer is made to ideally decay exponentially in conductivity to improve the effectiveness of eliminating the virtual cathode from the arresting anode side.

It will be appreciated by those skilled in the art that the various methods of establishing directionality and the various methods of mitigating virtual cathode described above can be used in any combination to achieve directionality whilst mitigating virtual cathode, such that even higher threshold nerves can be activated with reliable directional selectivity.

The invention claimed is:

1. A nerve interface device comprising:
at least one cuff portion having an assembled position in which the at least one cuff portion forms at least part of a passageway for receiving a nerve along a longitudinal axis passing through the passageway; and
a first ring of electrodes and a second ring of electrodes mounted on the at least one cuff portion, each of the first ring of electrodes and the second ring of electrodes comprising a plurality of electrodes, and wherein each electrode in the first ring of electrodes has a corresponding longitudinally-aligned electrode in the second ring of electrodes so as to form a plurality of pairs of electrodes spaced apart from each other along the longitudinal axis;
and wherein the at least one cuff portion comprises a spatially asymmetric configuration about a central axis perpendicular to the longitudinal axis to provide a passive imbalance and impedance mismatch along the longitudinal axis of the nerve interface device.

2. The nerve interface device of claim 1, wherein each electrode in the first ring of electrodes is an anode electrode and each electrode in the second ring of electrodes is a cathode electrode.

3. The nerve interface device of claim 2, wherein each anode electrode comprises a plurality of electrode portions, and further wherein one of the plurality of electrode portions has a different surface area than the others of the plurality of electrode portions.

4. The nerve interface device of claim 3, wherein a first one of the plurality of electrode portions that is closer to a corresponding cathode electrode than a second one of the plurality of electrodes portions has a larger surface area than a second one of the plurality of electrode portions.

5. The nerve interface device of claim 3, wherein the plurality of electrode portions comprises:
a first electrode portion, a second electrode portion and a third electrode portion;
wherein the first electrode portion is closer to a corresponding cathode than the second electrode portion or the third electrode portions portion; and
wherein the second electrode portion is closer to a corresponding cathode than the third electrode portion.

6. The nerve interface device of claim 5, wherein the first electrode portion has a larger surface area than the second electrode portion.

7. The nerve interface device of claim 6, wherein the second electrode portion has a larger surface area than the third electrode portion.

8. The nerve interface device of claim 3, wherein each one of the plurality of electrode portions are electrically connected to one another so as to form a unitary electrode.

9. The nerve interface device of claim 3, wherein each one of the plurality of electrode portions is stimulated with a different current.

10. The nerve interface device of claim 3, wherein the plurality of electrode portions comprises:
a first electrode portion, a second electrode portion, a third electrode portion and a fourth electrode portion;
wherein there is a gap between each one of the first electrode portion, the second electrode portion, the third electrode portion, and the fourth electrode portion;
wherein the first electrode portion is closer to a corresponding cathode than the second electrode portion, the third electrode portion and the fourth electrode portion;
wherein the second electrode portion is closer to a corresponding cathode than the third electrode portion and the fourth electrode portion;
wherein the third electrode portion is closer to a corresponding cathode than the fourth electrode portion;
wherein an impedance of the first electrode portion is lower than an impedance of the second electrode portion, the third electrode portion and the fourth electrode portion;
wherein an impedance of the second electrode portion is lower than an impedance of the third electrode portion and the fourth electrode portion: and
wherein an impedance of the third electrode portion is lower than an impedance of the fourth electrode portion.

11. The nerve interface device of claim 2, wherein each anode electrode has a triangular shape.

12. The nerve interface device of claim 2, wherein each anode electrode is connected to a first current source and each cathode electrode is connected to a second current source, and further wherein the first current source delivers a different current than the second current source.

13. The nerve interface device of claim 1, wherein at least one of a first electrode or a second electrode in a first pair of electrodes comprises a gradient in impedance along the longitudinal axis.

14. The nerve interface device of claim 13, wherein the impedance increases along a length of the at least one of the first electrode or the second electrode parallel to the longitudinal axis in the direction away from the other of the at least one of the first electrode or the second electrode within the at least one of the plurality of pairs of electrodes.

15. The nerve interface device of claim 14, wherein an end cuff portion comprises a gradient in impedance along the longitudinal axis.

16. The nerve interface device of claim 15, wherein the impedance increases along the end cuff portion parallel to the longitudinal axis in the direction away from the other of the at least one of the first electrode or the second electrode within the at least one of the plurality of pairs of electrodes.

17. The nerve interface device of claim 1, wherein a surface area of each cathode electrode is larger than the surface area of the corresponding anode electrode in a first pair of electrodes.

18. The nerve interface device of claim 1, wherein the asymmetric configuration comprises:
   a first insulation portion positioned towards a proximal end of the at least one cuff portion and a second insulation portion positioned towards a distal end of the at least one cuff portion;
   wherein the first insulation portion and the second insulation portion are arranged to contact the nerve in the assembled position; and
   wherein a size of the first insulation portion arranged to contact the nerve is different from a size of the second insulation portion arranged to contact the nerve.

19. The nerve interface device of claim 1, wherein the asymmetric configuration comprises:
   a first central off set between the central axis and a first electrode of the first pair of electrodes, and a second central offset between the central axis and a second electrode of the first pair of electrodes; wherein the first central offset is different from the second central offset.

20. The nerve interface device of claim 1, wherein the asymmetric configuration comprises:
   a first radial off set between the longitudinal axis and a first electrode of the first pair of electrodes, and a second radial offset between the longitudinal axis and a second electrode of the first pair of electrodes;
   wherein the first radial offset is different from the second radial offset.

21. The nerve interface device of claim 1, wherein the asymmetric configuration comprises:
   a first electrode and a second electrode in the first pair of electrodes mounted on opposing sides of the central axis;
   wherein the first electrode is different from the second electrode.

22. The nerve interface device of claim 1, wherein the asymmetric configuration comprises:
   a first electrode and a second electrode in the first pair of electrodes mounted on opposing sides of the central axis;
   wherein the first electrode is configured to have a first surface area in contact with the nerve in the assembled position, and the second electrode is configured to have a second surface area in contact with the nerve in the assembled position;
   wherein the first surface area is different from the second surface area.

* * * * *